US008173371B2

(12) United States Patent
Liu et al.

(10) Patent No.: US 8,173,371 B2
(45) Date of Patent: May 8, 2012

(54) SERIAL COUPLING OF NUCLEIC ACID METABOLISM AND EXTENSION FOR NUCLEIC ACID AMPLIFICATION

(75) Inventors: Qiang Liu, Arcadia, CA (US); Steve S. Sommer, Duarte, CA (US)

(73) Assignee: City of Hope, Duarte, CA (US)

(*) Notice: Subject to any disclaimer, the term of this patent is extended or adjusted under 35 U.S.C. 154(b) by 0 days.

(21) Appl. No.: 12/956,656

(22) Filed: Nov. 30, 2010

(65) Prior Publication Data

US 2011/0124051 A1 May 26, 2011

Related U.S. Application Data

(60) Continuation of application No. 12/612,162, filed on Nov. 4, 2009, now Pat. No. 7,919,253, which is a continuation of application No. 12/402,206, filed on Mar. 11, 2009, now Pat. No. 7,914,995, which is a continuation of application No. 11/772,622, filed on Jul. 2, 2007, now Pat. No. 7,504,221, which is a continuation of application No. 10/798,844, filed on Mar. 12, 2004, now Pat. No. 7,238,480, which is a continuation of application No. 10/434,369, filed on May 9, 2003, now Pat. No. 7,033,763, which is a continuation-in-part of application No. 10/269,879, filed on Oct. 15, 2002, now Pat. No. 7,105,298, which is a division of application No. 09/789,556, filed on Feb. 22, 2001, now Pat. No. 6,534,269.

(60) Provisional application No. 60/184,315, filed on Feb. 23, 2000, provisional application No. 60/187,035, filed on Mar. 6, 2000, provisional application No. 60/237,180, filed on Oct. 3, 2000, provisional application No. 60/379,092, filed on May 10, 2002.

(51) Int. Cl.
*C12Q 1/68* (2006.01)
*C12P 19/34* (2006.01)

(52) U.S. Cl. ............... 435/6.12; 435/91.1; 435/91.2
(58) Field of Classification Search ............ 435/6.1, 435/6.12, 91.1, 91.2
See application file for complete search history.

(56) References Cited

U.S. PATENT DOCUMENTS

| | | | |
|---|---|---|---|
| 5,302,509 A | 4/1994 | Cheeseman |
| 5,792,607 A | 8/1998 | Backman et al. |
| 5,804,375 A | 9/1998 | Gelfand et al. |
| 5,824,518 A | 10/1998 | Kacian et al. |
| 6,159,693 A | 12/2000 | Shultz et al. |
| 6,200,757 B1 | 3/2001 | Kurn et al. |
| 6,235,480 B1 | 5/2001 | Shultz et al. |
| 6,268,146 B1 | 7/2001 | Shultz et al. |
| 6,270,973 B1 | 8/2001 | Lewis et al. |
| 6,270,974 B1 | 8/2001 | Shultz et al. |
| 6,277,578 B1 | 8/2001 | Shultz et al. |
| 6,312,902 B1 | 11/2001 | Shultz et al. |
| 6,335,162 B1 | 1/2002 | Shultz et al. |
| 6,379,898 B2 | 4/2002 | Shultz et al. |
| 6,391,551 B1 | 5/2002 | Shultz et al. |
| 6,509,157 B1 | 1/2003 | Martinez |
| 6,534,269 B2 | 3/2003 | Liu et al. |
| 6,653,078 B2 | 11/2003 | Lewis et al. |
| 2001/0014451 A1 | 8/2001 | Shultz et al. |
| 2001/0031470 A1 | 10/2001 | Shultz et al. |
| 2003/0049624 A1 | 3/2003 | Shultz et al. |
| 2003/0077621 A1 | 4/2003 | Shultz et al. |
| 2003/0162199 A1 | 8/2003 | Bonner |
| 2003/0194699 A1 | 10/2003 | Lewis et al. |
| 2003/0203358 A1 | 10/2003 | Shultz et al. |

FOREIGN PATENT DOCUMENTS

| | | |
|---|---|---|
| EP | 0892058 A2 | 1/1999 |
| EP | 0892058 A3 | 1/1999 |
| WO | 0162952 A1 | 8/2001 |
| WO | 0162975 A2 | 8/2001 |

OTHER PUBLICATIONS

Bi, W. and Stambrook, P.J., "Detection of known mutation by proof-reading PCR," Nucleic Acids Res, 1998, 26:3073-3075.
Meyer, P.R. et al., "Unblocking of chain-terminated primer by HIV-1 reverse transcriptase through a nucleotide-dependent mechanism," Proc Natl Acad Sci USA, 1998, 95:13471-13476.
Liu, Q. et al., "Pyrophosphorolysis-Activated Polymerization (PAP): Application to Allele-Specific Amplification," Biotechniques 29:1072-1083, 2000.
Sommer, S.S., et al., "PCR Amplification of Specific Alles (PASA) is a General Method for Rapidly Detecting Known Single-Base Changes," biotechniques 12(1):82-87, 1992.
Tabor, S., et al., "DNA Sequence Analysis with a Modified Bacteriophage T7 DNA Polymerase," The Journal of Biological Chemistry 265(14):8322-8328, May 15, 1990.
Liu, Q. et al., "Overlapping PCR for Bidirectional PCR Amplification of Specific Alleles: A Rapid One-Tube Method for Simultaneously Differentiating Homozygotes and Heterozygotes," Genome Research, vol. 7, pp. 389-398, 1997.

(Continued)

Primary Examiner — Kenneth R. Horlick
(74) Attorney, Agent, or Firm — Rothwell, Figg, Ernst & Manbeck P.C.

(57) ABSTRACT

A novel method of pyrophosphorolysis activated polymerization (PAP) has been developed. In PAP, pyrophosphorolysis and polymerization by DNA polymerase are coupled serially for each amplification by using an activatable oligonucleotide P* that has a non-extendible 3'-deoxynucleotide at its 3' terminus. PAP can be applied for exponential amplification or for linear amplification. PAP can be applied to amplification of a rare allele in admixture with one or more wild-type alleles by using an activatable oligonucleotide P* that is an exact match at its 3' end for the rare allele but has a mismatch at or near its 3' terminus for the wild-type allele. PAP is inhibited by a mismatch in the 3' specific sequence as far as 16 nucleotides away from the 3' terminus. PAP can greatly increase the specificity of detection of an extremely rare mutant allele in the presence of the wild-type allele. Specificity results from both pyrophosphorolysis and polymerization since significant nonspecific amplification requires the combination of mismatch pyrophosphorolysis and misincorporation by the DNA polymerase, an extremely rare event. Using genetically engineered DNA polymerases greatly improves the efficiency of PAP.

5 Claims, 33 Drawing Sheets

OTHER PUBLICATIONS

Komura, J., et al., "Terminal transferase-dependent PCR: a versatile and sensitive method for in vivo footprinting and detection of DNA adducts," Nucleic Acids Research, 1998, vol. 26, No. 7, pp. 1807-1811, © 1996 Oxford University Press.

Meyer, P.R. et al., "A Mechanism of AZT Resistance: An Increase in Nucleotide-Dependent Primer Unblocking by Mutant HIV-1 Reverse Transcriptase," Molecular Cell, vol. 4, pp. 35-43, Jul. 1999.

Austermann, S. et al., "Inhibition of Human Immunodeficiency Virus Type 1 Reverse Transcriptase by 3'-Blocked Oligonucleotide Primers," Biochemical Pharmacology, vol. 43, No. 12, pp. 2581-2589, 1992.

Non-Final Office Action dated Jan. 26, 2010, U.S. Appl. No. 12/402,206, filed Mar. 11, 2009, 17 pages; Response to Office Action dated Jun. 28, 2010, 8 pages.

Ronaghi, M. et al., "Real-Time DNA Sequencing Using Detection of Pyrophosphate Release," Analytical Biochemistry 242, pp. 84-89 (1996), No. 0432, 6 pages.

"Gene Identification by Arrested Primer Extension," Biotechniques, Informa Healthcare, US, vol. 14, No. 6, Jun. 1, 1993, pp. 948-952, XP000377149, 5 pages.

European Office Action dated Jan. 13, 2012, Application No. 10 183 576.7-1212, Ref. HB/G24981EP-D1, City of Hope, 7 pages.

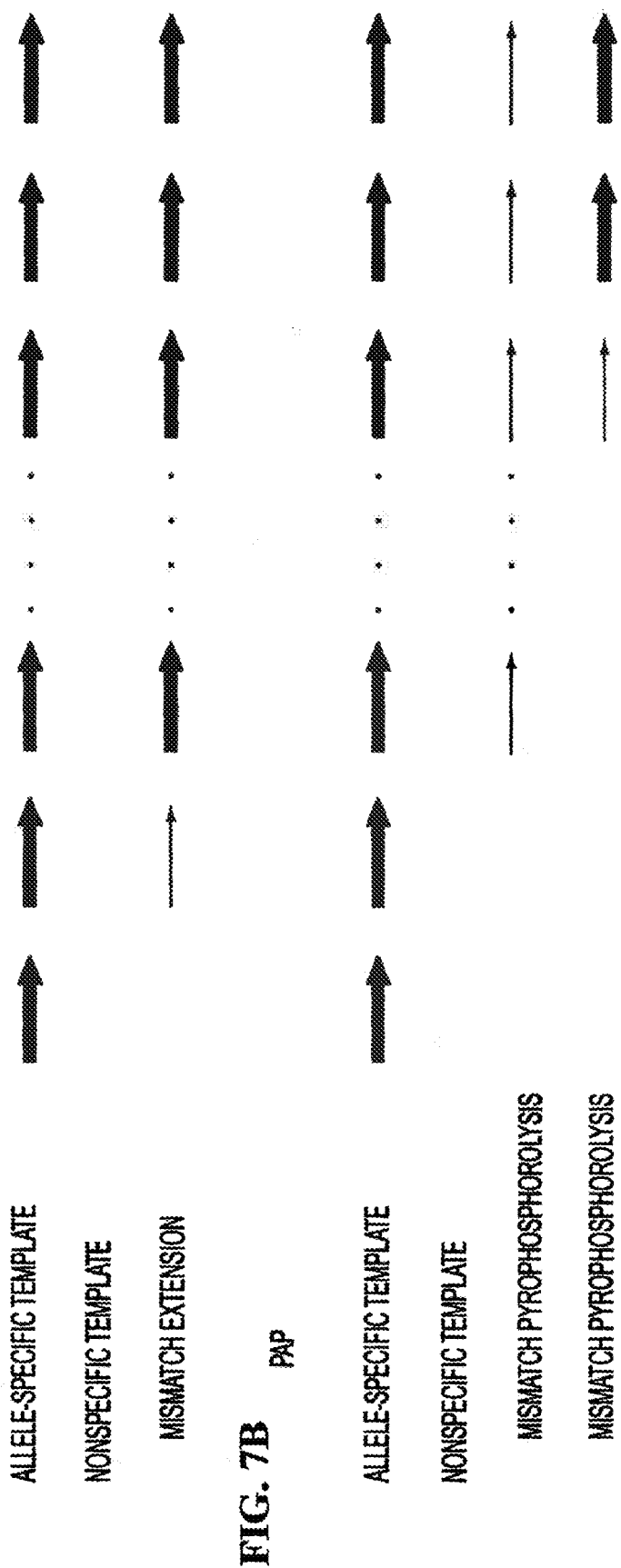
FIG. 7A  PASA
ALLELE-SPECIFIC TEMPLATE
NONSPECIFIC TEMPLATE
MISMATCH EXTENSION
FIG. 7B  PAP
ALLELE-SPECIFIC TEMPLATE
NONSPECIFIC TEMPLATE
MISMATCH PYROPHOSPHOROLYSIS
MISMATCH PYROPHOSPHOROLYSIS AND MISINCORPORATION

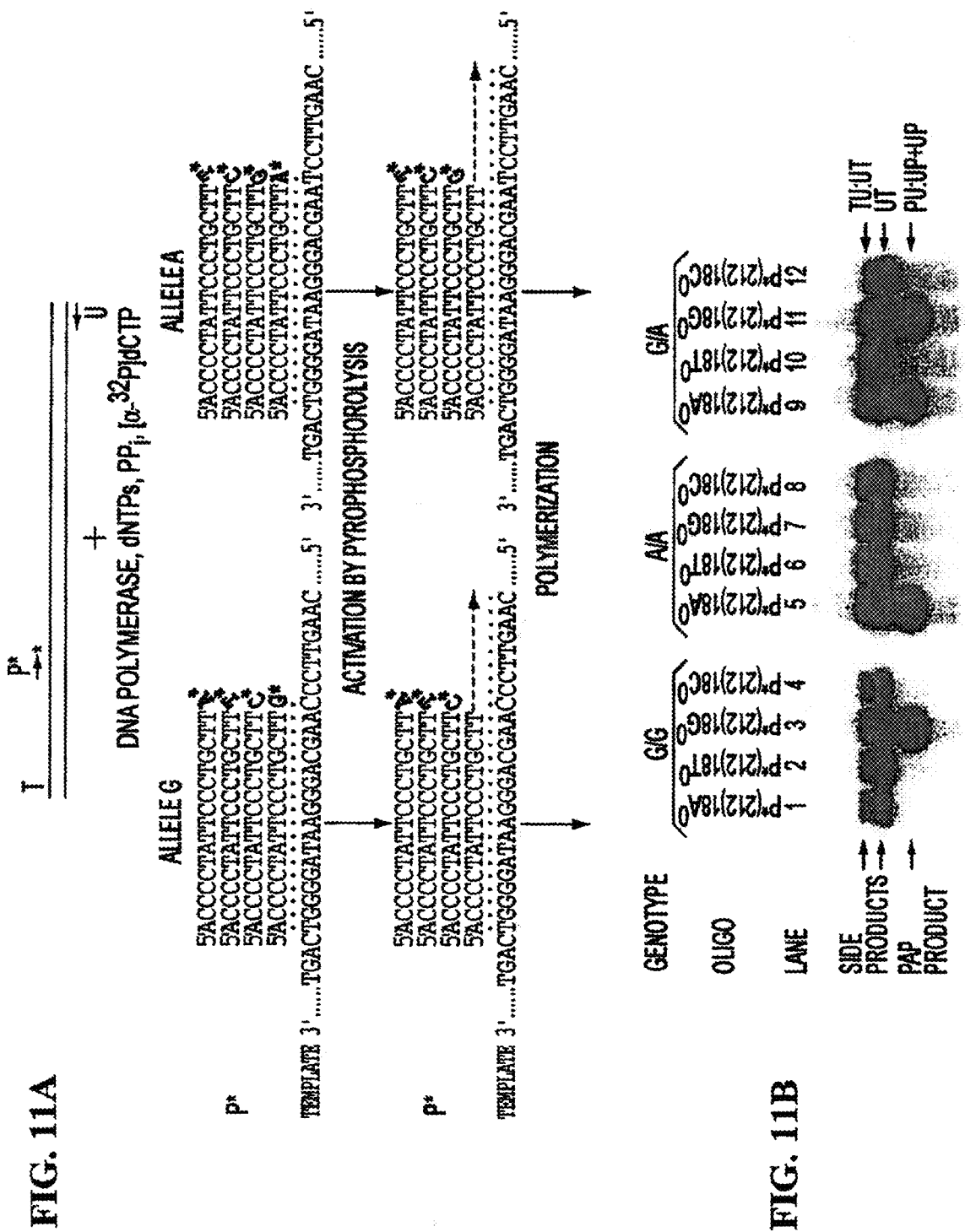

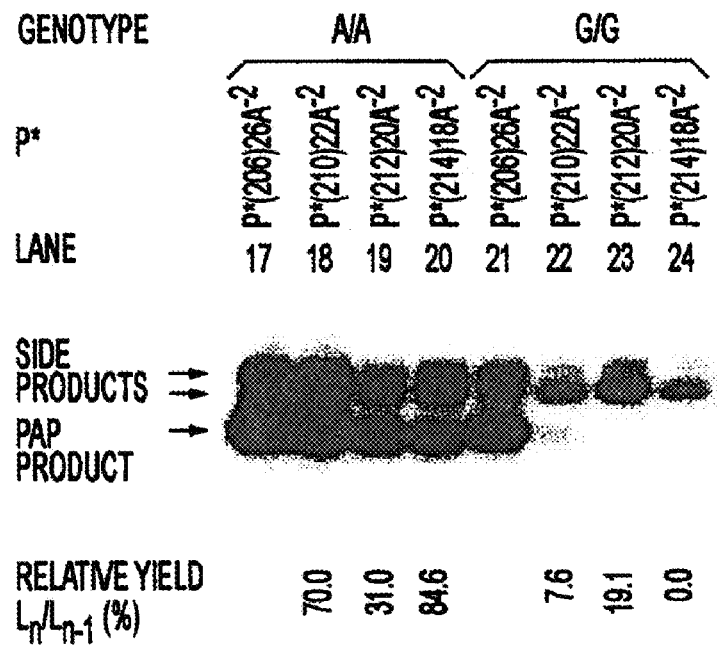
FIG. 12C
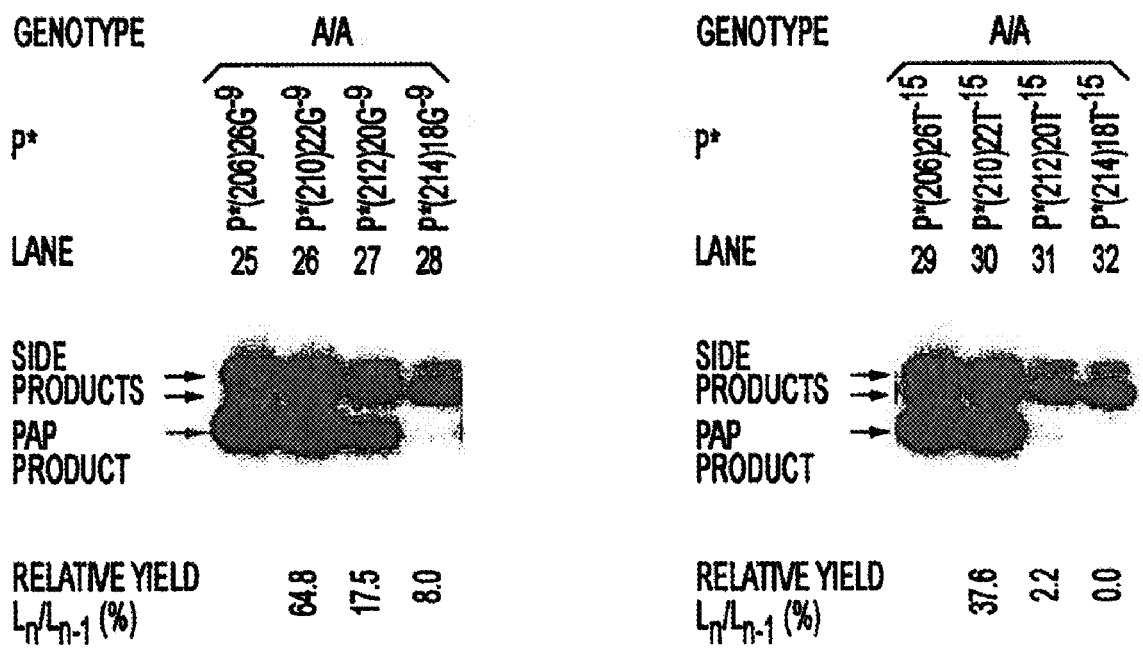
FIG. 12D  FIG. 12E

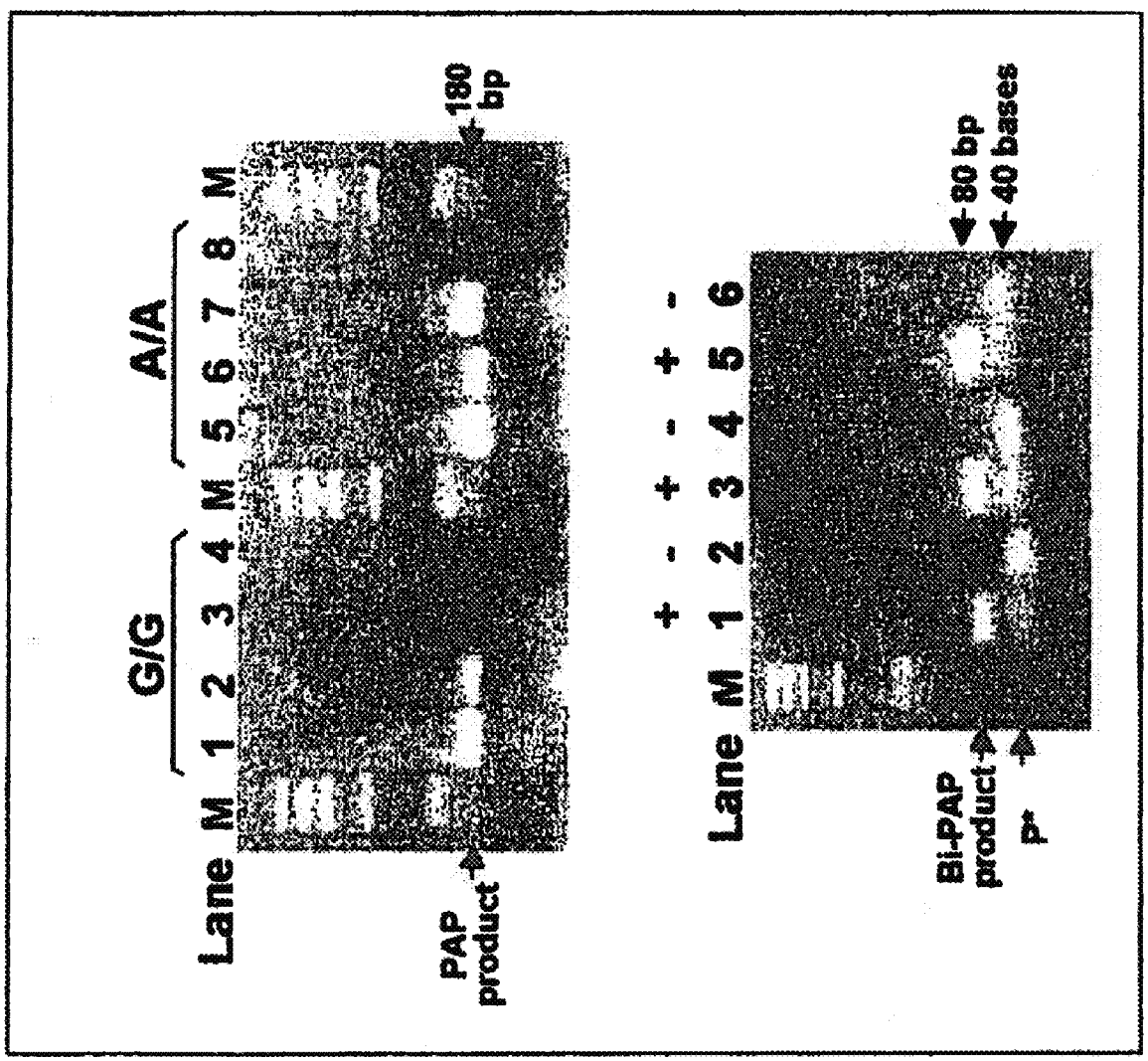

| Template : P* Match Product | | | Template : P* Match Product | | |
|---|---|---|---|---|---|
| WT:Mut | No | No | Mut:Mut | Yes | Yes |

P*      5'...TGGCACAT*
T       3'..CGCACCGTGTTGTTGACCGCC..5'
P*      5'..GCGTGGCACAACAACTGGGCG..3'
                    *AGTTGACC...5'

5'...TGGCACAT*
                    *AGTTGACC...5'

5'...TGGCACAT*
3'..CGCACCGTGTAGTTGACCGCC..5'
5'..GCGTGGCACATCAACTGGGGG..3'
                   *AGTTGACCG..5'

⬇ Bi-PAP

P     5'...TGGCACAT*CAACTGG...>
        <...ACCGTGTAGTTGACC...5'

FIG. 20A

Wildtype  5'.GCGTGGCACAACAACTGGCG.3'
Template  3'.CGCACCGTGTTGTTGACCGCC.5'   *Match*

WT    5'...TGGCACAA*
                           *TGTTGACC...5'    Yes

Mut   5'...TGGCACAT*
                           *AGTTGACC...5'    No
P*

Mut   5'...TGGCACAG*
                           *CGTTGACC...5'    No

Mut   5'...TGGCACAC*
                           *GGTTGACC...5'    No

⬇ PAP

*Product*

WT    5'...TGGCACAACAACTGG...>
                 <...ACCGTGTTGTTGACC...5'    +

Mut   5'...TGGCACAT*
                           *AGTTGACC...5'    −
P*

Mut   5'...TGGCACAG*
                           *CGTTGACC...5'    −

Mut   5'...TGGCACAC*
                           *GGTTGACC...5'    −

Assembly of positive signals by one base overlapping

5'...TGGCACAA*
         *TGTTGACC...5'

5'...GGCACAAC*
         *GTTGACCG...5'

5'...GCACAACA*
         *TTGACCGC...5'

5'...CACAACAA*
         *TGACCGCC...5'

Reconstruction of the unknown sequence

5'......ACAA......3'
3'......TGTT......5'

SEQUENCE LISTING

```
<160> NUMBER OF SEQ ID NOS: 72

<210> SEQ ID NO 1
<211> LENGTH: 24
<212> TYPE: DNA
<213> ORGANISM: Artificial
<220> FEATURE:
<223> OTHER INFORMATION: Amplification primer

<400> SEQUENCE: 1
gacctgcagc aagggagtca gaag                                          24

<210> SEQ ID NO 2
<211> LENGTH: 24
<212> TYPE: DNA
<213> ORGANISM: Artificial
<220> FEATURE:
<223> OTHER INFORMATION: Amplification primer

<400> SEQUENCE: 2
tcataccgga aagggctgga gata                                          24

<210> SEQ ID NO 3
<211> LENGTH: 33
<212> TYPE: DNA
<213> ORGANISM: Homo sapiens

<400> SEQUENCE: 3
aatctgactg acccctattc cctgcttrgg aac                                33

<210> SEQ ID NO 4
<211> LENGTH: 21
```

-continued

```
<212> TYPE: DNA
<213> ORGANISM: Artificial
<220> FEATURE:
<223> OTHER INFORMATION: Oligonucleotide

<400> SEQUENCE: 4
actgacccct attccctgct t                                                 21

<210> SEQ ID NO 5
<211> LENGTH: 22
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (22)..(22)
<223> OTHER INFORMATION: dideoxynucleotide

<400> SEQUENCE: 5
actgacccct attccctgct tg                                                22

<210> SEQ ID NO 6
<211> LENGTH: 23
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (23)..(23)
<223> OTHER INFORMATION: dideoxynucleotide

<400> SEQUENCE: 6
actgacccct attccctgct tgg                                               23

<210> SEQ ID NO 7
<211> LENGTH: 24
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (24)..(24)
<223> OTHER INFORMATION: dideoxynucleotide

<400> SEQUENCE: 7
actgacccct attccctgct tggg                                              24

<210> SEQ ID NO 8
<211> LENGTH: 25
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (25)..(25)
<223> OTHER INFORMATION: dideoxynucleotide

<400> SEQUENCE: 8
actgacccct attccctgct tgggg                                             25

<210> SEQ ID NO 9
<211> LENGTH: 26
<212> TYPE: DNA
<213> ORGANISM: Artificial
<220> FEATURE:
<223> OTHER INFORMATION: Oligonucleotide
```

```
<220> FEATURE:
<221> NAME/KEY: misc_feature
<222> LOCATION: (26)..(26)
<223> OTHER INFORMATION: dideoxynucleotide

<400> SEQUENCE: 9
tctgactgac ccctattccc tgcttg                                              26

<210> SEQ ID NO 10
<211> LENGTH: 24
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (24)..(24)
<223> OTHER INFORMATION: dideoxynucleotide

<400> SEQUENCE: 10
tgactgaccc ctattccctg ctta                                                24

<210> SEQ ID NO 11
<211> LENGTH: 24
<212> TYPE: DNA
<213> ORGANISM: Artificial
<220> FEATURE:
<223> OTHER INFORMATION: Oligonucleotide

<400> SEQUENCE: 11
tcataccgga aagggctgga gata                                                24

<210> SEQ ID NO 12
<211> LENGTH: 26
<212> TYPE: DNA
<213> ORGANISM: Artificial
<220> FEATURE:
<223> OTHER INFORMATION: Oligonucleotide

<400> SEQUENCE: 12
taggaacttg gggggtgtca gagccc                                              26

<210> SEQ ID NO 13
<211> LENGTH: 26
<212> TYPE: DNA
<213> ORGANISM: Artificial
<220> FEATURE:
<223> OTHER INFORMATION: Oligonucleotide

<400> SEQUENCE: 13
tctgactgac ccctattccc tgcttg                                              26

<210> SEQ ID NO 14
<211> LENGTH: 22
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (22)..(22)
<223> OTHER INFORMATION: dideoxynucleotide

<400> SEQUENCE: 14
actgacccct attccctgct tg                                                  22

<210> SEQ ID NO 15
<211> LENGTH: 20
```

```
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (20)..(20)
<223> OTHER INFORMATION: dideoxynucleotide

<400> SEQUENCE: 15
tgacccctat tccctgcttg                                          20

<210> SEQ ID NO 16
<211> LENGTH: 18
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (18)..(18)
<223> OTHER INFORMATION: dideoxynucleotide

<400> SEQUENCE: 16
acccctattc cctgcttg                                            18

<210> SEQ ID NO 17
<211> LENGTH: 26
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (26)..(26)
<223> OTHER INFORMATION: dideoxynucleotide

<400> SEQUENCE: 17
ctattccctg cttgggaact tgaggg                                   26

<210> SEQ ID NO 18
<211> LENGTH: 22
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (22)..(22)
<223> OTHER INFORMATION: dideoxynucleotide

<400> SEQUENCE: 18
tccctgcttg ggaacttgag gg                                       22

<210> SEQ ID NO 19
<211> LENGTH: 20
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (20)..(20)
<223> OTHER INFORMATION: dideoxynucleotide

<400> SEQUENCE: 19
cctgcttggg aacttgaggg                                          20

<210> SEQ ID NO 20
<211> LENGTH: 18
```

```
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (18)..(18)
<223> OTHER INFORMATION: dideoxynucleotide

<400> SEQUENCE: 20
tgcttgggaa cttgaggg                                              18

<210> SEQ ID NO 21
<211> LENGTH: 26
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (26)..(26)
<223> OTHER INFORMATION: dideoxynucleotide

<400> SEQUENCE: 21
tgactgaccc ctattccctg cttagg                                     26

<210> SEQ ID NO 22
<211> LENGTH: 22
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (22)..(22)
<223> OTHER INFORMATION: dideoxynucleotide

<400> SEQUENCE: 22
tgacccctat ccctgctta gg                                          22

<210> SEQ ID NO 23
<211> LENGTH: 20
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (20)..(20)
<223> OTHER INFORMATION: dideoxynucleotide

<400> SEQUENCE: 23
acccctattc cctgcttagg                                            20

<210> SEQ ID NO 24
<211> LENGTH: 18
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (18)..(18)
<223> OTHER INFORMATION: dideoxynucleotide

<400> SEQUENCE: 24
ccctattccc tgcttagg                                              18

<210> SEQ ID NO 25
<211> LENGTH: 26
```

```
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (26)..(26)
<223> OTHER INFORMATION: dideoxynucleotide

<400> SEQUENCE: 25
tgactgaccc ctattcgctg cttagg                                          26

<210> SEQ ID NO 26
<211> LENGTH: 22
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (22)..(22)
<223> OTHER INFORMATION: dideoxynucleotide

<400> SEQUENCE: 26
tgacccctat tcgctgctta gg                                              22

<210> SEQ ID NO 27
<211> LENGTH: 20
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (20)..(20)
<223> OTHER INFORMATION: dideoxynucleotide

<400> SEQUENCE: 27
acccctattc gctgcttagg                                                 20

<210> SEQ ID NO 28
<211> LENGTH: 18
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (18)..(18)
<223> OTHER INFORMATION: dideoxynucleotide

<400> SEQUENCE: 28
ccctattcgc tgcttagg                                                   18

<210> SEQ ID NO 29
<211> LENGTH: 26
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (26)..(26)
<223> OTHER INFORMATION: dideoxynucleotide

<400> SEQUENCE: 29
tgactgaccc ttattccctg cttagg                                          26

<210> SEQ ID NO 30
<211> LENGTH: 22
```

```
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (22)..(22)
<223> OTHER INFORMATION: dideoxynucleotide

<400> SEQUENCE: 30
tgacccttat tccctgctta gg                                              22

<210> SEQ ID NO 31
<211> LENGTH: 20
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (20)..(20)
<223> OTHER INFORMATION: dideoxynucleotide

<400> SEQUENCE: 31
acccttattc cctgcttagg                                                 20

<210> SEQ ID NO 32
<211> LENGTH: 18
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (18)..(18)
<223> OTHER INFORMATION: dideoxynucleotide

<400> SEQUENCE: 32
ccttattccc tgcttagg                                                   18

<210> SEQ ID NO 33
<211> LENGTH: 40
<212> TYPE: DNA
<213> ORGANISM: Homo sapiens

<400> SEQUENCE: 33
gactgacccc tattccctgc ttrggaactt gagggtgtc                            40

<210> SEQ ID NO 34
<211> LENGTH: 18
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (18)..(18)
<223> OTHER INFORMATION: dideoxynucleotide

<400> SEQUENCE: 34
acccctattc cctgctta                                                   18

<210> SEQ ID NO 35
<211> LENGTH: 18
<212> TYPE: DNA
<213> ORGANISM: Artificial
<220> FEATURE:
<223> OTHER INFORMATION: Oligonucleotide
<220> FEATURE:
<221> NAME/KEY: misc_feature
```

```
<222> LOCATION: (18)..(18)
<223> OTHER INFORMATION: dideoxynucleotide

<400> SEQUENCE: 35
attccctgct tgggaact                                                18

<210> SEQ ID NO 36
<211> LENGTH: 18
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (18)..(18)
<223> OTHER INFORMATION: dideoxynucleotide

<400> SEQUENCE: 36
ccctgcttgg gaacttga                                                18

<210> SEQ ID NO 37
<211> LENGTH: 18
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (18)..(18)
<223> OTHER INFORMATION: dideoxynucleotide

<400> SEQUENCE: 37
tgcttgggaa cttgaggg                                                18

<210> SEQ ID NO 38
<211> LENGTH: 18
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (18)..(18)
<223> OTHER INFORMATION: dideoxynucleotide

<400> SEQUENCE: 38
acccctattc cctgattg                                                18

<210> SEQ ID NO 39
<211> LENGTH: 18
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (18)..(18)
<223> OTHER INFORMATION: dideoxynucleotide

<400> SEQUENCE: 39
acccctattc cgtgcttg                                                18

<210> SEQ ID NO 40
<211> LENGTH: 18
<212> TYPE: DNA
<213> ORGANISM: Artificial
<220> FEATURE:
<223> OTHER INFORMATION: Oligonucleotide
<220> FEATURE:
<221> NAME/KEY: misc_feature
```

```
<222> LOCATION: (18)..(18)
<223> OTHER INFORMATION: dideoxynucleotide

<400> SEQUENCE: 40
acccctatcc cctgcttg                                                18

<210> SEQ ID NO 41
<211> LENGTH: 18
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (18)..(18)
<223> OTHER INFORMATION: dideoxynucleotide

<400> SEQUENCE: 41
accccgattc cctgcttg                                                18

<210> SEQ ID NO 42
<211> LENGTH: 18
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (18)..(18)
<223> OTHER INFORMATION: dideoxynucleotide

<400> SEQUENCE: 42
actcctattc cctgcttg                                                18

<210> SEQ ID NO 43
<211> LENGTH: 25
<212> TYPE: DNA
<213> ORGANISM: Homo sapiens

<400> SEQUENCE: 43
tctgactgac ccctattccc tgctt                                        25

<210> SEQ ID NO 44
<211> LENGTH: 24
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (24)..(24)
<223> OTHER INFORMATION: dideoxynucleotide

<400> SEQUENCE: 44
tgactgaccc ctattccctg ctta                                         24

<210> SEQ ID NO 45
<211> LENGTH: 26
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (26)..(26)
<223> OTHER INFORMATION: dideoxynucleotide

<400> SEQUENCE: 45
tctgactgac ccctattccc tgcttg                                       26
```

```
<210> SEQ ID NO 46
<211> LENGTH: 24
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (24)..(24)
<223> OTHER INFORMATION: dideoxynucleotide

<400> SEQUENCE: 46
actgacccct attccctgct tggg                                              24

<210> SEQ ID NO 47
<211> LENGTH: 26
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (26)..(26)
<223> OTHER INFORMATION: dideoxynucleotide

<400> SEQUENCE: 47
taggaacttg ggggggtgtca gagccc                                           26

<210> SEQ ID NO 48
<211> LENGTH: 24
<212> TYPE: DNA
<213> ORGANISM: Artificial
<220> FEATURE:
<223> OTHER INFORMATION: Oligonucleotide

<400> SEQUENCE: 48
acggcagcac agaccagcgt gttc                                              24

<210> SEQ ID NO 49
<211> LENGTH: 24
<212> TYPE: DNA
<213> ORGANISM: Artificial
<220> FEATURE:
<223> OTHER INFORMATION: Oligonucleotide

<400> SEQUENCE: 49
ttgccactca agcggtcctc tcat                                              24

<210> SEQ ID NO 50
<211> LENGTH: 24
<212> TYPE: DNA
<213> ORGANISM: Artificial
<220> FEATURE:
<223> OTHER INFORMATION: Oligonucleotide

<400> SEQUENCE: 50
gaagcaatct ggctgtgcaa agtg                                              24

<210> SEQ ID NO 51
<211> LENGTH: 26
<212> TYPE: DNA
<213> ORGANISM: Artificial
<220> FEATURE:
<223> OTHER INFORMATION: Oligonucleotide

<400> SEQUENCE: 51
tctgactgac ccctattccc tgctta                                            26
```

<210> SEQ ID NO 52
<211> LENGTH: 26
<212> TYPE: DNA
<213> ORGANISM: Artificial
<220> FEATURE:
<223> OTHER INFORMATION: Oligonucleotide

<400> SEQUENCE: 52
tctgactgac ccctattccc tgcttg						26

<210> SEQ ID NO 53
<211> LENGTH: 26
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (26)..(26)
<223> OTHER INFORMATION: dideoxynucleotide

<400> SEQUENCE: 53
tctgactgac ccctattccc tgctta						26

<210> SEQ ID NO 54
<211> LENGTH: 26
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (26)..(26)
<223> OTHER INFORMATION: dideoxynucleotide

<400> SEQUENCE: 54
tctgactgac ccctattccc tgcttg						26

<210> SEQ ID NO 55
<211> LENGTH: 20
<212> TYPE: DNA
<213> ORGANISM: Homo sapiens

<400> SEQUENCE: 55
cgagaagttt ttgaaaacac						20

<210> SEQ ID NO 56
<211> LENGTH: 20
<212> TYPE: DNA
<213> ORGANISM: Homo sapiens

<400> SEQUENCE: 56
gaacatacag agcaaaagcg						20

<210> SEQ ID NO 57
<211> LENGTH: 30
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (30)..(30)
<223> OTHER INFORMATION: acyclonucleotide

<400> SEQUENCE: 57
cgaagcctgt aaagcggcgg tgcacaatcg						30

<210> SEQ ID NO 58
<211> LENGTH: 25
<212> TYPE: DNA
<213> ORGANISM: Artificial
<220> FEATURE:
<223> OTHER INFORMATION: Oligonucleotide

<400> SEQUENCE: 58
actgttgatg ggtgtctggt cagag                                    25

<210> SEQ ID NO 59
<211> LENGTH: 30
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (30)..(30)
<223> OTHER INFORMATION: acyclonucleotide

<400> SEQUENCE: 59
tgatcagccc actgacgcgt tgcgcgagac                               30

<210> SEQ ID NO 60
<211> LENGTH: 21
<212> TYPE: DNA
<213> ORGANISM: Artificial
<220> FEATURE:
<223> OTHER INFORMATION: Oligonucleotide

<400> SEQUENCE: 60
acaactggcg ggcaaacagt c                                        21

<210> SEQ ID NO 61
<211> LENGTH: 40
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (40)..(40)
<223> OTHER INFORMATION: dideoxynucleotide

<400> SEQUENCE: 61
gatggcggag ctgaattaca ttcccaaccg cgtggcacat                    40

<210> SEQ ID NO 62
<211> LENGTH: 40
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (40)..(40)
<223> OTHER INFORMATION: dideoxynucleotide

<400> SEQUENCE: 62
ggcaacgcca atcagcaacg actgtttgcc cgccagttga                    40

<210> SEQ ID NO 63
<211> LENGTH: 40
<212> TYPE: DNA
<213> ORGANISM: Artificial
<220> FEATURE:
<223> OTHER INFORMATION: Oligonucleotide

```
<220> FEATURE:
<221> NAME/KEY: misc_feature
<222> LOCATION: (40)..(40)
<223> OTHER INFORMATION: dideoxynucleotide

<400> SEQUENCE: 63
gaagcggcgt cgaagcctgt aaagcggcgg tgcacaatcg                              40

<210> SEQ ID NO 64
<211> LENGTH: 42
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (42)..(42)
<223> OTHER INFORMATION: dideoxynucleotide

<400> SEQUENCE: 64
gcggatagtt aatgatcagc ccactgacgc gttgcgcgag ac                           42

<210> SEQ ID NO 65
<211> LENGTH: 40
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (40)..(40)
<223> OTHER INFORMATION: dideoxynucleotide

<400> SEQUENCE: 65
gaagcggcgt cgaagcctgt aaagcggcgg tgcacaatcc                              40

<210> SEQ ID NO 66
<211> LENGTH: 42
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (42)..(42)
<223> OTHER INFORMATION: dideoxynucleotide

<400> SEQUENCE: 66
gcggatagtt aatgatcagc ccactgacgc gttgcgcgag ag                           42

<210> SEQ ID NO 67
<211> LENGTH: 40
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (40)..(40)
<223> OTHER INFORMATION: dideoxynucleotide

<400> SEQUENCE: 67
gaagcggcct cgaagcctgt aaagcggcgg tgcacaatct                              40

<210> SEQ ID NO 68
<211> LENGTH: 42
<212> TYPE: DNA
<213> ORGANISM: Artificial
<220> FEATURE:
<223> OTHER INFORMATION: Oligonucleotide
```

```
<220> FEATURE:
<221> NAME/KEY: misc_feature
<222> LOCATION: (42)..(42)
<223> OTHER INFORMATION: dideoxynucleotide

<400> SEQUENCE: 68
gcggatagtt aatgatcagc ccactgacgc gttgcgcgag aa                              42

<210> SEQ ID NO 69
<211> LENGTH: 40
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (40)..(40)
<223> OTHER INFORMATION: dideoxynucleotide

<400> SEQUENCE: 69
gatggcggag ctgaattaca ttcccaaccg cgtggcacaa                                 40

<210> SEQ ID NO 70
<211> LENGTH: 40
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (40)..(40)
<223> OTHER INFORMATION: dideoxynucleotide

<400> SEQUENCE: 70
ggcaacgcca atcagcaacg actgtttgcc cgcctattgt                                 40

<210> SEQ ID NO 71
<211> LENGTH: 40
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (40)..(40)
<223> OTHER INFORMATION: dideoxynucleotide

<400> SEQUENCE: 71
tacattccca accgcgtggc acaacaactg gcgggcaaac                                 40

<210> SEQ ID NO 72
<211> LENGTH: 40
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (40)..(40)
<223> OTHER INFORMATION: dideoxynucleotide

<400> SEQUENCE: 72
gggccagact ggaggtggca acgccaatca gcaacgactg                                 40
```

SERIAL COUPLING OF NUCLEIC ACID METABOLISM AND EXTENSION FOR NUCLEIC ACID AMPLIFICATION

CROSS-REFERENCE TO RELATED APPLICATIONS

The present application is a continuation of U.S. patent application Ser. No. 12/612,162 filed 4 Nov. 2009, now U.S. Pat. No. 7,919,253, which in turn is a continuation of U.S. patent application Ser. No. 12/402,206 filed 11 Mar. 2009, now U.S. Pat. No. 7,914,995 which in turn is a continuation of U.S. patent application Ser. No. 11/772,622 filed 2 Jul. 2007, now U.S. Pat. No. 7,504,221, which in turn is a continuation of U.S. patent application Ser. No. 10/798,844 filed 12 Mar. 2004, now U.S. Pat. No. 7,238,480, which in turn is a continuation of U.S. patent application Ser. No. 10/434,369 filed 9 May 2003, now U.S. Pat. No. 7,033,763, which in turn is a continuation-in-part of U.S. patent application Ser. No. 10/269,879 filed on 15 Oct. 2002, now U.S. Pat. No. 7,105,298, which in turn is a division of U.S. patent application Ser. No. 09/789,556 filed on 22 Feb. 2001, now U.S. Pat. No. 6,534,269. application Ser. No. 09/789,556 is further related to and claims priority under 35 USC §119(e) to U.S. provisional patent application Ser. Nos. 60/184,315 filed on 23 Feb. 2000, 60/187,035 filed on 6 Mar. 2000 and 60/237,180 filed on 3 Oct. 2000. Application Ser. No. 10/434,369 is further related to and claims priority under 35 USC §119(e) to U.S. provisional patent application Ser. No. 60/379,092 filed on 10 May 2002. Each of these applications is incorporated herein by reference.

SEQUENCE SUBMISSION

The present application is being filed along with a Sequence Listing in electronic format. The Sequence Listing is entitled 1954_545_Sequence_Listing.txt, was created on 29 Nov. 2010 and is 17 kb in size. The information in the electronic format of the Sequence Listing is part of the present application and is incorporated herein by reference in its entirety.

BACKGROUND OF THE INVENTION

This invention relates to nucleic acid polymerization and amplification. In particular, it relates to a novel and general method for nucleic acid amplification, in which pyrophosphorolysis and polymerization are serially-coupled. The method has been adapted for allele-specific amplification and can greatly increase the specificity to detect an extremely rare allele in the presence of wild-type alleles. We refer to the method as pyrophosphorolysis activated polymerization (PAP).

The publications and other materials used herein to illuminate the background of the invention or provide additional details respecting the practice, are incorporated by reference, and for convenience are respectively grouped in the appended Bibliography.

Multiple methods for detecting mutations present in less than 10% of cells (i.e. rare alleles) have been developed, including PCR amplification of specific alleles (PASA), peptide nucleic acid (PNA) clamping blocker PCR, allele-specific competitive blocker PCR, mismatch amplification mutation assay (MAMA), restriction fragment-length polymorphism (RFLP)/PCR (Parsons and Heflich, 1997) and QE-PCR (Ronai and Minamoto, 1997). These methods: i) amplify the rare allele selectively, ii) destroy the abundant wild-type allele, or iii) spatially separate the rare allele from the wild-type allele. The specificity achievable under typical research/clinical conditions is $10^{-3}$ (Parsons and Heflich, 1997), although a few publications reported higher specificity of detection (Pourzand and Cerutti, 1993; Knoll et al., 1996). These methods either do not generally achieve the higher specificity or are not suitable for routine analysis.

A robust method of detecting one mutant allele in $10^4$-$10^9$ wild-type alleles would be advantageous for many applications including detecting minimal residual disease (recurrence after remission or rare remaining cancer cells in lymph nodes and other neighboring tissues) and measurement of mutation load (the frequency and pattern of somatic mutations present in normal tissues). Individuals with a high mutation load may be at increased risk for cancer due to either environmental exposure or endogenous defects in any of hundreds of genes necessary to maintain the integrity of the genome. For those individuals found to have a high mutation load, clues to etiology can be obtained by defining the mutation pattern.

There are many DNA sequencing methods and their variants, such as the Sanger sequencing using dideoxy termination and denaturing gel electrophoresis (Sanger et al., 1977), Maxam-Gilbert sequencing using chemical cleavage and denaturing gel electrophoresis (Maxam and Gilbert, 1977), gyro-sequencing detecting pyrophosphate ($PP_i$) released during the DNA polymerase reaction (Ronaghi et al., 1998), and sequencing by hybridization (SBH) using oligonucleotides (Lysov et al., 1988; Bains and Smith, 1988; Drmanac et al., 1989; Khrapko et al., 1989; Pevzner et al., 1989; Southern et al., 1992).

There are multiple gel-based methods for scanning for unknown mutations including single stranded conformation polymorphism (SSCP) and the SSCP-hybrid methods of dideoxy fingerprinting (ddF), restriction endonuclease fingerprinting (REF), and Detection Of Virtually All Mutations-SSCP (DOVAM-S), denaturing gradient gel electrophoresis (DGGE), denaturing HPLC (dHPLC) chemical or enzymatic cleavage (Sarkar et al., 1992; Liu and Sommer, 1995; Liu et al., 1999; Myers et al., 1985; Cotton et al., 1988; Liu et al., 1999; Buzin et al., 2000; Spiegelman et al., 2000). DOVAM-S and chemical cleavage reactions have been shown in blinded analyses to identify essentially all mutations (Buzin et al., 2000). dHPLC, which is based on reverse phase chromatography, also may identify essentially all mutations under appropriate conditions (O'Donovan et al., 1998; Oefner and Underhill, 1998; Spiegelman et al., 2000). Efforts are under way to develop general scanning methods with higher throughput.

Sequencing by hybridization (SBH) is being adapted to scanning or resequencing for unknown mutations on microarrays (Southern, 1996). This continues to be a promising area of intense study. However it is not possible as yet to detect most microinsertions and deletions with this approach and the signal to noise ratio for single base changes precludes detection of 5-10% of single nucleotide changes (Hacia, 1999). Alternative approaches warrant exploration.

It is becoming increasingly apparent that in vivo chromatin structure is crucial for mammalian gene regulation and development. Stable changes in chromatin structure often involve changes in methylation and/or changes in histone acetylation. Somatically heritable changes in chromatin structure are commonly called epigenetic changes (Russo and Riggs, 1996) and it is now clear that epigenetic "mistakes" or epimutations are frequently an important contributing factor to the development of cancer (Jones and Laird, 1999).

One of the few methods for assaying in vivo chromatin structure, and the only method with resolution at the single nucleotide level, is ligation-mediated PCR (LM-PCR) (Mueller and Wold, 1989; Pfeifer et al., 1989) and its variant of terminal transferase-mediated PCR (TD-PCR) (Komura and Riggs, 1998). Many aspects of chromatin structure can be determined by LM-PCR, such as the location of methylated cytosine residues, bound transcription factors, or positioned nucleosomes. It is readily apparent that LM-PCR works better with some primer sets than with others. Thus, it is desired to develop a more robust method of measuring chromatin structure.

Thus, it is an object of the present invention to develop alternative methods for amplification of DNA, for sequencing DNA and for analysis of chromatin structure. This object is accomplished by the use of the novel pyrophosphorolysis activated polymerization (PAP) as described herein. PAP has the potential to enhance dramatically the specificity of the amplification of specific alleles, for resequencing DNA and for chromatin structure analysis.

SUMMARY OF THE INVENTION

The invention is a pyrophosphorolysis activated polymerization (PAP) method of synthesizing a desired nucleic acid strand on a nucleic acid template strand. The method comprises the following steps carried out serially.

(a) Annealing to the template strand a complementary activatable oligonucleotide P*. This activatable oligonucleotide has a non-extendible 3' terminus that is activatable by pyrophosphorolysis (hereinafter referred to as a non-extendible 3' terminus or a 3' non-extendible end or a non-extendible 3' end). The non-extendible 3' terminus (or end) is a nucleotide or nucleotide analog which has the capacity to form a Watson-Crick base pair with a complementary nucleotide and which lacks a 3' OH capable of being extended by a nucleic acid polymerase. In one embodiment, the non-extendible 3' terminus may be a non-extendible 3' deoxynucleotide, such as a dideoxynucleotide. In a second embodiment, the non-extendible 3' terminus may be a chemically modified nucleotide lacking the 3' hydroxyl group, such as an acyclonucleotide. Acyclonucleotides substitute a 2-hydroxyethoxymethyl group for the 2'-deoxyribofuranosyl sugar normally present in dNMPs. In other embodiments, the non-extendible 3' terminus may be other blockers as described herein. In one embodiment, the activatable oligonucleotide P* has no nucleotides at or near its 3' terminus that mismatch the corresponding nucleotides on the template strand. In a second embodiment, the activatable oligonucleotide P* has a mismatch at or within 16 nucleotides of its 3' terminus with respect to a corresponding nucleotide on the template strand. The terminal 3'-deoxynucleotide is hybridized to the template strand when the oligonucleotide P* is annealed.

(b) Pyrophosphorolyzing the annealed activatable oligonucleotide P* with pyrophosphate and an enzyme that has pyrophosphorolysis activity. This activates the oligonucleotide P* by removal of the hybridized non-extendible 3' terminus.

(c) Polymerizing by extending the activated oligonucleotide P* on the template strand in presence of four nucleoside triphosphates of their analogs and a nucleic acid polymerase to synthesize the desired nucleic acid strand.

The PAP method can be applied to amplify a desired nucleic acid strand by the following additional steps.

(d) Separating the desired nucleic acid strand of step (c) from the template strand, and (e) Repeating steps (a)-(d) until a desired level of amplification of the desired nucleic acid strand is achieved.

In a preferred aspect, the PAP method as described above is applied to allele-specific amplification (PAP-A). In this application, the nucleic acid template strand is a sense or antisense strand of one allele and is present in admixture with the corresponding (sense or antisense) nucleic acid strand of the second allele (the allelic strand). The activatable oligonucleotide P* has at least one nucleotide or analog at or near its 3' terminus, e.g., within 16 nucleotides of the 3' terminus, that mismatches the corresponding nucleotide of the allelic strand. Because of the mismatch, in step (a) of the PAP method the non-extendible 3' terminus of oligonucleotide P* is not substantially hybridized to the allelelic strand. In step (b) the pyrophosphorolysis does not substantially remove the non-hybridized non-extendible 3' terminus from the activatable oligonucleotide P* annealed to the allelic strand. In step (c) the oligonucleotide P* is not substantially extended by polymerization on the allelic strand. As a result, the desired nucleic acid strand synthesized on the template strand is amplified preferentially over any nucleic acid strand synthesized on the allelelic strand.

In a second preferred aspect, the PAP-A method described above can be performed bidirectionally (Bi-PAP-A). Bidirectional-PAP (Bi-PAP) is a novel design that preferably uses two opposing pyrophosphorolysis activatable oligonucleotides (P*) with one nucleotide overlap at their 3' termini. Thus, in Bi-PAP, PAP-A is performed with a pair of opposing activatable oligonucleotide P*s. Both the downstream and upstream P*s are specific for the nucleotide of interest at the 3' termini (e.g., an A:T base pair). In the initial round of amplification from genomic DNA, segments of undefined size are generated. In subsequent rounds, a segment equal to the combined lengths of the oligonucleotides minus one is amplified exponentially. Nonspecific amplification occurs at lower frequencies because this design eliminates misincorporation error from an unblocked upstream. The P*s may be 30-60 nucleotides for most efficient amplification.

The PAP method can be used to amplify either RNA or DNA. When used to amplify DNA, the activatable oligonucleotide P* may be a 2'-deoxyoligonucleotide, the non-extendible 3' terminus may be, e.g., a 2',3'-dideoxynucleotide or an acyclonucleotide or other blockers as described herein, the four nucleoside triphosphates are 2'-deoxynucleoside triphosphates or their analogs, and the nucleic acid polymerase is a DNA polymerase. The DNA polymerase used in step (c) can also be the enzyme having pyrophosphorolysis activity used in step (b). Preferred DNA polymerases having pyrophosphorolysis activity are thermostable Tfl, Taq, and genetically engineered DNA polymerases, such as AmpliTaqFs and ThermoSequenase™. These genetically engineered DNA polymerases have the mutation F667Y or an equivalent mutation in their active sites. The use of genetically engineered DNA polymerases, such as AmpliTaqFs and ThermoSequenase™, greatly improves the efficiency of PAP. These Family I DNA polymerases can be used when the activatable oligonucleotide P* is a 3' dideoxynucleotide or an acyclonucleotide. When the activatable oligonucleotide P* is an acyclonucleotide, Family II archaeon DNA polymerases can also be used. Examples of such polymerases include, but are not limited to, Vent (exo-) and Pfu (exo-). These polymerases efficiently amplify 3' acyclonucleotide blocked P*. Two or more polymerases can also be used in one reaction. If the template is RNA, the nucleic acid polymerase may be RNA polymerase, reverse transcriptase, or their variants. The activatable oligonucleotide P* may be a ribonucleotide or a 2'-deoxynucleotide. The non-extendible 3' terminus may be a 3' deoxyribonucleotide or an acyclonucleotide. The four nucleoside triphosphates may be ribonucleoside triphosphates, 2' deoxynucleoside triphosphates or their analogs. For convenience, the description that follows uses DNA as the template. However, RNA is also included, such as described for the present aspect.

Amplification by the PAP method can be linear or exponential. Linear amplification is obtained when the activatable oligonucleotide P* is the only complementary oligonucleotide used. Exponential amplification is obtained when a second opposing oligonucleotide, which may be a P*, is present that is complementary to the desired nucleic acid strand. The activatable oligonucleotide P* and the second oligonucleotide flank the region that is targeted for amplification. In step (a) the second oligonucleotide anneals to the separated desired nucleic acid strand product of step (d). In step (c) polymerization extends the second oligonucleotide on the desired nucleic acid strand to synthesize a copy of the nucleic acid template strand. In step (d) the synthesized nucleic acid template strand is separated from the desired nucleic acid strand. Steps (a) through (d) are repeated until the desired level exponential amplification has been achieved.

In the PAP method, a mismatch between the activatable oligonucleotide P* and the template strand results in no substantial amplification, if the mismatch occurs in the 3' specific subsequence of P* at the 3' terminus of P* or within 16 nucleotides of the 3' terminus of P*. This lack of amplification for such mismatches in the 3' specific subsequence of P* provides four billion different and specific oligonucleotides with one base substitution resolution.

In a preferred aspect, the PAP method is used for exponential amplification of a rare, mutant allele in a mixture containing one or more wild-type alleles. Strands of the alleles are separated to provide single-stranded nucleic acid, and then the following steps are carried out serially.

(a) Annealing to the sense or antisense strands of each allele a complementary activatable 2'-deoxyoligonucleotide P* that has a non-extendible 3' terminus. The non-extendible 3' terminus may be, e.g., a non-extendible 2',3'-dideoxynucleotide or an acyclonucleotide. P* has no 2'-deoxynucleotides at or near its 3' terminus that mismatch the corresponding 2'-deoxynucleotides on the mutant strand, but has at least one 2'-deoxynucleotide at or near its 3' terminus that mismatches the corresponding 2'-deoxynucleotide on the wild-type stand. Consequently, the non-extendible 3' terminus is hybridized to the mutant strand but not to the wild-type strand when the oligonucleotide P* is annealed. Simultaneously, a second 2'-deoxyoligonucleotide that is complementary to the anti-parallel strands of each allele is annealed to the anti-parallel strands. The activatable 2'-deoxyoligonucleotide P* and the second 2'-deoxyoligonucleotide flank the region of the gene to be amplified.

(b) Pyrophosphorolyzing the activatable 2'-deoxyoligonucleotide P* that is annealed to a mutant strand with pyrophosphate and an enzyme that has pyrophosphorolysis activity. This activates the 2'-deoxyoligonucleotide P* that is annealed to the mutant strand by removal of the hybridized non-extendible 3' terminus. It does not substantially activate the 2'-deoxyoligonucleotide P* when it is annealed to the mutant strand because the non-hybridized non-extendible 3' terminus is not substantially removed by the pyrophosphorolysis.

(c) Polymerizing by extending the activated oligonucleotide P* on the mutant strand in presence of four nucleoside triphosphates or their analogs and a DNA polymerase and extending the second 2'-deoxyoligonucleotide on both mutant and wild-type anti-parallel strands.

(d) Separating the extension products of step (c);

(e) Repeating steps (a)-(d) until the desired level of amplification of the mutant allele has been achieved.

The activatable 2'-deoxyoligonucleotide P* is annealed to the antisense strands of the alleles and the second 2'-deoxyoligonucleotide is annealed to the sense strands, or vice versa.

Steps (a) to (c) of PAP can be conducted sequentially as two or more temperature stages on a thermocycler, or they can be conducted as one temperature stage on a thermocycler.

Nucleoside triphosphates and 2'-deoxynucleoside triphosphates or their chemically modified versions may be used as substrates for multiple-nucleotide extension by PAP, i.e., when one nucleotide is incorporated the extending strand can be further extended. 2',3'-dideoxynucleoside triphosphates, their chemically modified versions, acyclonucleotides or other blocked nucleotides which are terminators for further extension may be used for single-nucleotide extension. 2',3'-dideoxynucleoside triphosphates may be labeled with radioactivity or dye for differentiation from the 3' terminal dideoxynucleotide, if present, of oligonucleotide P*. Mixtures of nucleoside triphosphates or 2'-deoxynucleotide triphosphates or their analogs, and 2',3'-dideoxynucleoside triphosphates or their analogs may also be used.

PAP can be used in a novel method of DNA sequence determination. In PAP, pyrophosphorolysis and polymerization by DNA polymerase are coupled serially by using P*, an oligonucleotide containing a non-extendible 3' terminus. The non-extendible 3' terminus may be, e.g., a non-extendible 3'-deoxynucleotide or an acyclonucleotide. This principle is based on the specificity of PAP and in turn on the base pairing specificity of the 3' specific subsequence. This property of the 3' specific subsequence can be applied to scan or resequence for unknown sequence variants, to determine de novo DNA sequence, to compare two DNA sequences, and to monitor gene expression profiling in large scale. A P* array is possible in these methods. That is, each of the P*s can be immobilized at an individual dot or a solid support, thus allowing all the PAP reactions to be processed in parallel.

Thus in one aspect, the PAP method is used for scanning or resequencing unknown sequence variants within a predetermined sequence by carrying out the following steps serially.

(a) Mixing under hybridization conditions a template strand of the nucleic acid with multiple sets of four activatable oligonucleotides P* which are sufficiently complementary to the template strand to hybridize therewith. Within each set the oligonucleotides P* differ, from each other in having a different non-extendible 3' terminus, so that the non-extendible 3' terminus is hybridized to the template strand if the template strand is complementary to the non-extendible 3' terminus. The number of sets corresponds to the number of nucleotides in the sequence. The non-extendible 3' terminus may be, e.g., a non-extendible 3'-deoxynucleotide or an acyclonucleotide.

(b) Treating the resulting duplexed P*s with pyrophosphate and an enzyme that has pyrophosphorolysis activity to activate by pyrophosphorolysis only those oligonucleotides P* which have a non-extendible 3' terminus that is hybridized to the template strand.

(c) Polymerizing by extending the activated oligonucleotides P* on the template strand in presence of four nucleoside triphosphates or their analogs and a nucleic acid polymerase.

(d) Separating the nucleic acid strands synthesized in step (c) from the template strand.

(e) Repeating steps (a)-(d) until a desired level of amplification is achieved, and (f) Arranging the nucleic acid sequence in order by analyzing overlaps of oligonucleotides P* that produced amplifications.

In a second aspect, the PAP method is used for determining de novo the sequence of a nucleic acid by carrying out the following steps serially.

(a) Mixing under hybridization conditions a template strand of the nucleic acid with multiple activatable oligonucleotides P*. All of the oligonucleotides P* have the same number n of nucleotides as the template and constitute collectively all possible sequences having n nucleotides. All of the oligonucleotides P* have a non-extendible 3' terminus. The non-extendible 3' terminus may be, e.g., a non-extendible 3'-deoxynucleotide or an acyclonucleotide. Any oligonucleotides P* that are sufficiently complementary will hybridize to the template strand. The non-extendible 3' terminus will hybridize to the template strand only if the template strand is complementary at the position corresponding to the 3' terminus.

(b) Treating the resulting duplexed P*s with pyrophosphate and an enzyme that has pyrophosphorolysis activity to activate only those hybridized oligonucleotides P* which have a non-extendible 3' terminus that is hybridized to the template strand, by pyrophosphorolysis of those hybridized non-extendible 3' termini.

(c) Polymerizing by extending the activated oligonucleotides P* on the template strand in presence of four nucleoside triphosphates or their analogs and a nucleic acid polymerase.

(d) Separating the nucleic acid strands synthesized in step (c) from the template strand.

(e) Repeating steps (a)-(d) until a desired level of amplification has been achieved, and (f) Determining the sequence of oligonucleotides P* that produced amplifications, then arranging the nucleic acid sequence in order by analyzing overlaps of these oligonucleotides.

PAP can also be used to study chromatin structure analogously to ligation-mediated PCR (LM-PCR) by carrying out the following steps serially. LM-PAP has been used for the determination of primary nucleotide sequence, cytosine methylation patterns, DNA lesion formation and repair and in vivo protein-DNA footprints (Dai et al., 2000; Mueller and Wold, 1989; Pfeifer et al., 1989; Pfeifer et al., 1999; Becker and Grossman, 1993). Ligation-mediated PAP (LM-PAP) involves cleavage, primer extension, linker ligation and PAP that can be applied for analysis of in vivo chromatin structure, such as, methylated state of chromosomes, and for other nucleic acid analysis as for LM-PCR.

The nature of LM-PAP is that the template is synthesized before PAP, such as by ligation reaction or by extension using terminal transferase. PAP may be any type of PAP: with only one P*, with two opposing oligonucleotides where at least one is P*, Bi-PAP, matched PAP, mismatched PAP, and so on. Thus, at its simplest, LM-PAP is the application of PAP to a presynthesized template. LM-PAP may be performed by steps (i), (ii), (iii), (iv) and (v), by steps (i), (ii), (iii) and (vi), by steps (ii), (iii), (iv) and (v) or by steps (ii), (iii) and (vi), where the steps are as follows.

(i) The cleavage occurs chemically, enzymatically or naturally to "breakdown" nucleic acid strands. The nucleic acid usually is genomic DNA that may have lesions or nicks produced in vivo.

(ii) The oligonucleotide P1 is gene-specific and its extension includes: 1) annealing to the template strand a substantially complementary oligonucleotide; 2) extending the oligonucleotide on the template strand in the presence of nucleoside triphosphates or their analogs and a nucleic acid polymerase, the extension "runs off" at the cleavage site on the template strand. Steps 1) and 2) may be repeated.

The primer extension may be replaced by a P* extension, in which the above PAP is performed with only one activatable oligonucleotide P*.

(iii) The linker ligation step includes ligation of a linker to the 3' terminus of the synthesized nucleic acid strand. The linker ligation step may be replaced by a terminal transferase extension that is non-template dependent polymerization and an extra nucleic acid sequence is added to the 3' terminus of the synthesized nucleic acid strand.

(iv) PCR is performed with a second gene-specific oligonucleotide (P2) together with an oligonucleotide specific for the linker or the added sequence by terminal transferase.

(v) A third gene-specific P* (P3) is used to detect the PCR generated fragments. PAP method is applied with only one activatable oligonucleotide P*. The extension of the activated oligonucleotide P* "runs off" at the end of the template strand generated in IV. The PAP method may be applied in an allele-specific manner. The activatable oligonucleotide P* may contain one or more nucleotides that are not complementary to the template strand. The uncomplimentary nucleotide(s) of P* may locate at the 3' terminus of P*.

(vi) Instead of steps (iv) and (v), PAP method can be applied with two opposing oligonucleotides of which at least one is the activatable oligonucleotide P*. The activatable oligonucleotide P*(P3) is gene-specific. The second oligonucleotide is specific for the linker or the added sequence by terminal transferase. The second oligonucleotide may be another activatable oligonucleotide P* or a regular oligonucleotide. The PAP method may be applied in an allele-specific manner. The activatable oligonucleotide P* (P3) may contain one or more nucleotides that are not complementary to the template strand. The uncomplimentary nucleotide(s) of P* may locate at the 3' terminus of P* (P3).

The third gene-specific oligonucleotide (P3) is then usually used to label and allow visualization of the PCR generated fragments. P3 is labeled at the 5' terminus with $^{32}P$ or, more recently, with near infrared fluorochromes such as IRD 700 or IRD 800 (Li-Cor Inc.) (Dai et al., 2000).

PAP can be used to detect a target nucleic acid. In one embodiment this method involves the following steps:

(a) adding to a nucleic acid containing sample an oligonucleotide P*, wherein the oligonucleotide P* has a non-extendible 3' terminus, wherein the 3' terminal residue of oligonucleotide P* is removable by pyrophosphorolysis, and wherein the oligonucleotide P* anneals to a substantially complementary strand of the target nucleic acid present in the sample;

(b) removing the 3' non-extendible terminus of the oligonucleotide P* annealed to the substantially complementary strand of the target nucleic acid by pyrophosphorolysis to unblock the oligonucleotide P* to produce an unblocked oligonucleotide; and (c) detecting the presence of the target nucleic acid, wherein the sequence of the target nucleic acid is substantially complementary to the sequence of the oligonucleotide P*.

The method of the first embodiment may further include before the detection step the step: (b1) extending the unblocked oligonucleotide using a nucleic acid polymerase to produce an extended oligonucleotide. The method may also include the addition of a second oligonucleotide which may or may not have a 3' non-extendible terminus. The second oligonucleotide may anneal to the substantially complementary strand of the target nucleic acid or it may anneal to the complement of the substantially complementary strand of the target nucleic acid.

In a second embodiment for detecting a nucleic acid the method involves the following steps:

(a) adding to a nucleic acid containing sample two oligonucleotide P*s, wherein each oligonucleotide P* has a non-extendable 3' terminus, wherein the 3' terminal residue of each oligonucleotide P* is removable by pyrophosphorolysis, wherein one oligonucleotide P* overlaps with the other oligonucleotide P* by at least one nucleotide at their respective 3' ends, and wherein one oligonucleotide P* anneals to a substantially complementary strand of the target nucleic acid present in the sample and the other oligonucleotide P* anneals to a complement of the substantially complementary strand of the target nucleic acid;

(b) removing the 3' non-extendable terminus of the oligonucleotide P*s annealed to the target nucleic acid by pyrophosphorolysis to unblock the oligonucleotide P*s to produce unblocked oligonucleotides; and (c) detecting the presence of the target nucleic acid, wherein the sequence of the target nucleic acid is substantially complementary to the sequence of the oligonucleotide P*s.

The method of the second embodiment may further include before the detection step the step: (b1) extending the unblocked oligonucleotide using a nucleic acid polymerase to produce an extended oligonucleotide.

In one embodiment, the detection of the nucleic acid in step (c) is performed by detecting the unblocking of oligonucleotide P*. In one aspect, the unblocking is detected by loss of a label contained in the 3' terminal residue of oligonucleotide P*. In a second aspect, the unblocking is detected by detecting the presence of a 3' OH on the 3' terminal residue that is capable of extension or ligation. In this aspect, the detection is determined by extending the unblocked oligonucleotide or by ligating the unblocked oligonucleotide to an oligonucleotide. In a second embodiment, the detection of the nucleic acid in step (c) is performed by detecting the extended oligonucleotide. In one aspect, the extended oligonucleotide is detected by the presence of a label in the extended oligonucleotide. The label is part of a nucleotide or nucleotide analog used in the extension step. In a second aspect, the extended oligonucleotide is detected by gel electrophoresis. In a third aspect, the extended oligonucleotide is detected by the binding or incorporation of a dye or spectral material.

The P* oligonucleotides are selected to be "substantially" complementary" to the different strands of each specific sequence to be amplified. Therefore, the P* oligonucleotide sequence need not reflect the exact sequence of the template. For example, a non-complementary nucleotide segment may be attached to the 5'-end of the P* oligonucleotide, with the remainder of the P* oligonucleotide sequence being complementary to the strand. Alternatively, non-complementary bases or longer sequences can be interspersed into the P* oligonucleotide, provided that the P* oligonucleotide sequence has sufficient complementarity with the sequence of the strand to be amplified to hybridize therewith and form a template for synthesis of the extension product of the other P* oligonucleotide. The ability to detect nucleic acid sequences which are substantially complementary to oligonucleotide P* is particularly useful for the detection of multiple mutations, such as seen in high viral load, where the detection of the presence of the virus is important and not necessarily the exact nucleic acid sequence of the virus. This method is also capable of detecting nucleic acids that are completely complementary.

The present invention also includes other modifications of PAP.

The activatable oligonucleotide P* may contain blocked nucleotides at other positions in addition to the 3' terminus.

The introduction of internal blocking nucleotides results in an interface between amplification and PAP which would permit PAP to amplify in a non-exponential manner (e.g., quadratic or geometric) with higher fidelity, i.e., errors made by the polymerase would not be propagatable.

The activatable oligonucleotide P* may contain modified nucleotides that are extendible as well as the 3' blocked nucleotide. Thus, anywhere 5' to the 3' terminus, there may be either blocking or non-blocking modified nucleotides.

A polymerase that pyrophosphorolyzes the mismatched primer rather than the matched primer could be used to detect rare mutations in which the P* that mismatched at the 3' terminus is activated and extended.

The detection of a rare mutation is based on no mismatch anywhere along the length of the oligonucleotide because a mismatch inhibits the activation of P*s.

Activation may occur by another mechanism, such as a 3' exonuclease. The 3' exonuclease may have specificity for the matched primer or the mismatched primer so that it discriminates as to whether there is a mismatch at the 3' end. The 3' exonuclease can be used either way. If it prefers a mismatch, it can be used as described above, but its ability to detect uncommon mutations would depend on some specificity for activation, although that specificity may come partly from internal mismatches.

The extension reaction can be performed by a DNA polymerase, an RNA polymerase or a reverse transcriptase, the template may be a DNA or an RNA, and the oligonucleotide P* may be a DNA, an RNA, or a DNA/RNA heteromer.

Pyrophosphorolysis and the extension can be performed by different polymerases. For example, the P* may include a penultimate modified oligonucleotide that could not be extended by pyrophosphorolyzing polymerase but could be extended by another polymerase. One example is a 3' dideoxy that could be pyrophosphorolyzed by a DNA polymerase, but the presence of a ribonucleotide in the penultimate position would require extension by an RNA polymerase.

PAP can be generalized as an inactive oligonucleotide that is activated by a nucleic acid metabolizing enzyme, such as helicases, topoisomerases, telomerases, RNase H or restriction enzymes.

Methylases would detect the presence or absence of a methyl group in genomic DNA. Methylases could be coupled with truncating amplification which forces the polymerase back to the template.

A P* in which the 3' end is a dideoxy and penultimate few nucleotides are ribose can be used as a tool for differentially making a protein product derived from a specific mutation that was desired, or for making a protein product whose expression is linked to the presence of a particular sequence. Pyrophosphorolysis would activate the P* if there was a precise match to the mutation at the 3' end. The activated oligonucleotide is then a substrate for the generation of RNA by an RNA polymerase. The RNA could then be translated in vitro to produce the protein product.

PAP (PAP, Bi-PAP, matched or mismatched PAP, simplex PAP, multiplex PAP and others) can be used for quantification. The yield of the amplification products is quantitatively associated with the amount of input template. The association may be proportional or otherwise.

In PAP, product may accumulate linearly, exponentially or otherwise.

BRIEF DESCRIPTION OF THE FIGURES

FIGS. 7A and 7B are diagrams illustrating enhanced specificity of PAP relative to PASA.

FIG. 11A is a schematic illustrating enhancement of PAP efficiency.

FIG. 11B is an autoradiogram of PAP from the G/G, A/A and G/A genotypes of the human dopamine receptor gene.

FIGS. 12A-12E are autoradiograms showing the results of electrophoresis of samples obtained in Example 2 below.

FIG. 16A shows allele-specific LM-PAP versus allele-specific LM-PCR for the dopamine $D_1$ receptor gene. FIG. 16B shows LM-PAP for the pgk gene.

FIGS. 17A-17B show PAP amplification directly from human (FIG. 17A) and mouse (FIG. 17B) genomic DNA using PAP and Bi-PAP, respectively.

FIG. 18A: Model: A duplexed DNA template of the lacI gene is shown. The mutated template contains a G at the nucleotide position 369, while the wild-type template contains a T at the nucleotide position 369 of the lacI gene. P*=pyrophosphorolysis activatable oligonucleotide. The P* has an acycloNMP or a ddNMP at the 3' terminus. The P* is specific to the mutated template but mismatches to the wild-type template at the 3' terminus (Table 6). O=oligodeoxynucleotide. PAP was performed with P*1 and O1, P*2 and O2, or P*1 and P*2, respectively. FIG. 18B: PAP with 30 mer P*s: The P*s are specific for the mutated template but mismatch the wild-type template at their 3' terminus. In lanes 1-8 are 3' terminal acyclonucleotide blocked P*s. In lanes 9-16 are 3' terminal dideoxynucleotide blocked P*s for comparison. In lanes 1-4 and 9-12, the mutated template is used. In lanes 5-8 and 13-16, the wild-type template is used. The PAP product and P* are indicated with their sizes. Lane M is 120 ng of φX174-PUC19/HaeIII DNA marker. FIG. 18C: PAP with 35-mer P*s: The experiment is the same as in FIG. 18B except with 35-mer P*s that are 3' co-terminal with the 30-mer P*s and five nucleotides longer at their 5' termini. FIG. 18D: PAP with Vent (exo-) polymerase. The experiment is the same as in FIG. 18B except that Vent (exo-) was used. FIG. 18E: PAP with Pfu (exo-) polymerase. The experiment is the same as in FIG. 18B except that Pfu (exo-) was used.

FIGS. 20A-20B show Bi-PAP amplification. FIG. 20A: Schematic of Bi-PAP to detection a rare mutation. The mutation-specific assay with two mutated P* for nucleotide 190 is shown. The downstream and upstream P*s contain a dideoxy T and a dideoxy A at their 3' termini, respectively. They are specific for the T:A allele at nucleotide 190 (on the right), but are mismatched to the A:T wild-type allele at their 3' termini (on the left). The P*s are 40 nucleotides long and overlap at their 3' termini by one nucleotide. On the left, no substantial product is generated from the wild-type template because of the mismatch. On the right, the mutated product is generated efficiently from the mutated template. FIG. 20B: Bi-PAP amplification directly from λ DNA. Each of the wild-type and mutation-specific Bi-PAP assays at nucleotide 190 was used to amplify a 79-bp segment of the lacI gene from λ DNAs. For the wild-type assay in lanes 1-3, the two wild-type P*s have 3' terminal ddA and ddT, respectively. For the mutation-specific assay in lanes 4-6 and lanes 7-9, the two mutated P*s are with ddT and ddA at their 3' termini, respectively. In lanes 1, 4 and 7, 2000 copies of the wild-type template were added to each reaction. In lanes 2, 5 and 8, 2000 copies of the mutated template were added to each reaction. In lanes 3, 6 and 9, no template was added. In lanes 7-9, 200 ng of human genomic DNA was added as carrier. The product and P* are indicated. Lane M is 120 ng of φX174-PUC19/HaeIII DNA marker.

FIG. 21A: The mutation-specific Bi-PAP assay for A190T. In Experiment I, the copies of the wild-type λ DNA are indicated in lanes 1-5. Lane 6 is a negative control with no DNA. In Experiment II, the copies of the mutated λ DNA are indicated in lane 7-11. Lane 11 (0.2 copy) is a negative control to support the dilution accuracy of copy number. Lane 12 is a negative control with no DNA. In Experiment III, the copies of the mutated λ DNA in the presence of $2\times10^9$ copies of the wild-type λ DNA are indicated in lane 13-17. Lane 18 is a negative control with only the wild-type λ DNA. In Experiment IV, the copies of the mutated λ DNA in the presence of 100 ng of human genomic DNA are indicated in lanes 19-23. Lane 24 is negative control only with the human genomic DNA. Lane "C WT" is the wild-type product control in which the wild-type P*s were used to amplify 2000 copies of the wild-type λ DNA. Lane "C Mut" is the mutated product control in which the mutated P*s were used to amplify 2000 copies of the mutated λ DNA. The wild-type and mutated products with unique mobilities are indicated. FIG. 21B: The mutation-specific Bi-PAP assay for T369G. FIG. 21C: The mutation-specific Bi-PAP assay for T369C.

FIGS. 23A-23B show a schematic of Bi-PAP resequencing. FIG. 23A: Detection of the wild-type sequence. This is a close look at the microarray. The P*s are designed according to the wild-type sequence. On the position of nucleotide A, four Bi-PAPs are synthesized with four pairs of P*s. The four downstream P*s have identical sequence, except that at the 3' terminus either ddAMP, ddTMP, ddGMP or ddCMP, corresponds to the wild-type sequence and the three possible single base substitutions. The four corresponding upstream P*s have identical sequence, except that at the 3' terminus either ddTMP, ddAMP, ddCMP or ddGMP. Each pair of P*s have one nucleotide overlap at their 3' termini. On the next nucleotide C, another four pairs of P*s are synthesized (not shown). If the wild-type sample is added, only the wild-type Bi-PAPs generates the specific product that is labeled by fluorescence. In this way, to scan a 1 kb region, you need 8000 P*s. FIG. 23B: Detection of an A to T mutation. On the mutated nucleotide T, the mutation-specific Bi-PAP generates the mutated product. On the next nucleotide G, no product of Bi-PAP is generated because each pair of P* contains one or two mismatches (not shown).

Figure 24B:
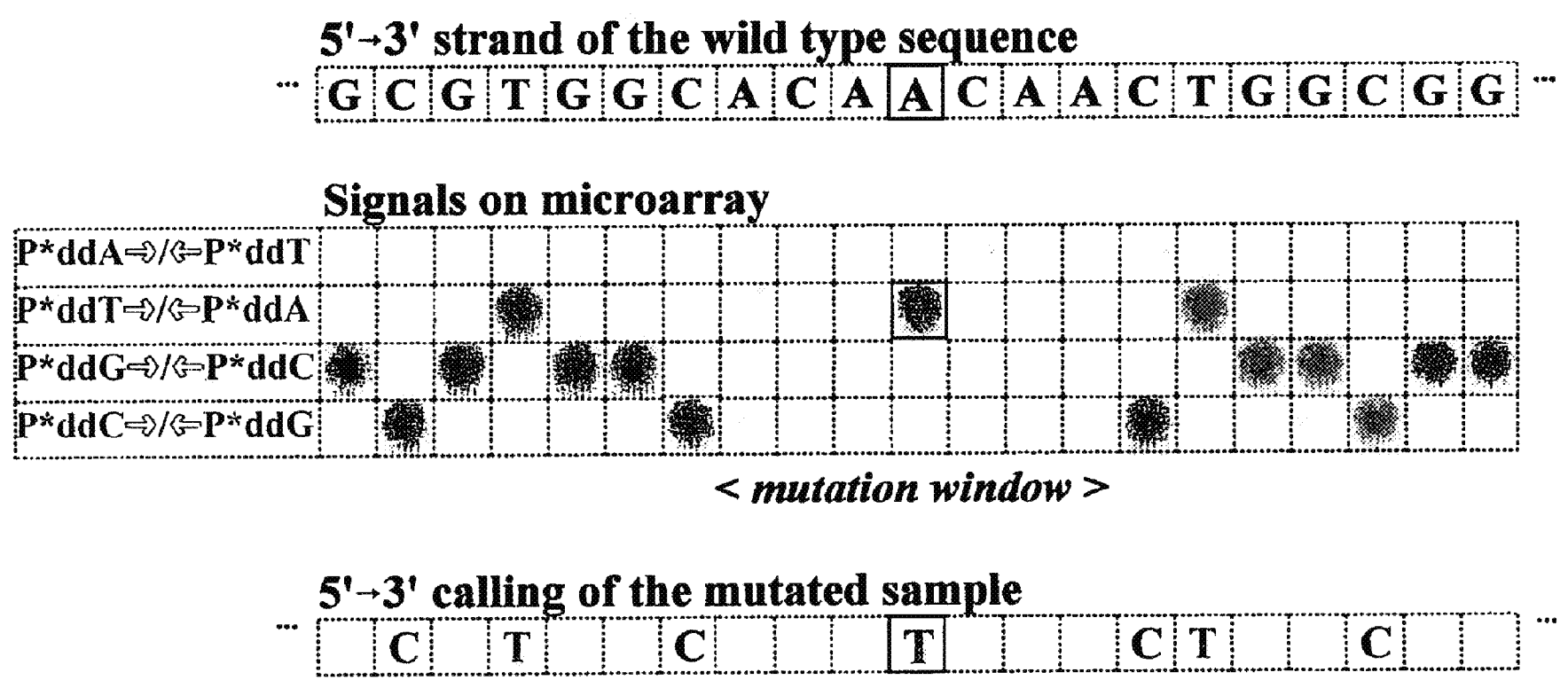

FIGS. 24A-24B show Bi-PAP resequencing microarray. FIG. 24A: Detection of the wild-type sequence. Four pairs of P*s are designed for each nucleotide position according to the wild-type sequence. Each pair of P*s are downstream and upstream directed, and have one overlap and complementary nucleotide at their 3' termini. The wild-type P* pair are specifically amplified on each nucleotide position. If all of the wild-type P* pairs specifically amplified, the wild-type sequence can be determined. FIG. 24B: Detection of the A to T mutation. With the mutated template, the mutation-specific Bi-PAP is amplified. There is a window of no Bi-PAP signals centered by the mutation-specific Bi-PAP and three successive nucleotides on each side. The paired specific subsequence is supposed to be seven nucleotides long. Any unknown single-base substitution can be determined, even if it is a heterozygous mutation. Also, small deletions and insertions can be detected and localized.

FIG. 26A: Eighteen genomic DNA samples of the lacI$^+$ transgenic mice were chosen. 2 μg genomic DNA of each sample was amplified with the assay B to detect the T369G mutation two times. Samples 1-10 are from livers of 25-month old mice. Samples 11-14 are from hearts (samples 11, 13 and 14) and adipose (sample 12) of 6-month old mice. Samples 15-18 are from brains of 10-day old mice. P=positive control that amplified the mutated λ DNA, N=negative control with no DNA, +=amplified product, −=no product. FIG. 26B: The assay B was performed. In lanes 11-12, 13-16 and 17-20, 2 μg, 0.5 μg and 0.125 μg of the lacI$^+$ mouse genomic DNA of sample 12 were used in each reaction, respectively. Lanes 1-10 are controls; the copy number of the mutated λ DNA per reaction was reconstructed by two-fold serial dilutions. In lanes 1-10 and 13-20, each reaction also contained 1 μg of the lacI$^-$ mouse genomic DNA carrier. ss=single-stranded, ds=double-stranded. FIG. 26C: The assay B was performed. In lanes 11-14, 2 μg of the lacI$^+$ mouse genomic DNA of sample 3 was used in each reaction. In lanes 15-18, 2 μg of the lacI$^+$ mouse genomic DNA of sample 9 was used in each reaction. Lanes 1-10 are controls; the copy number of the mutated λ DNA per reaction is indicated. Each control reaction also contained 1 μg of the lacI$^-$ mouse genomic DNA carrier.

DETAILED DESCRIPTION OF THE INVENTION

The following terminology is used herein.

Pyrophosphorolysis: removal of the 3' nucleotide from a nucleotide strand chain by DNA polymerase in the presence of pyrophosphate ($PP_i$) to generate the nucleotide triphosphate. This is the reverse of the polymerization reaction.

PAP: Pyrophosphorolysis activated polymerization. PAP can use one P* or can use two opposing oligonucleotides in which at least one is P*.

P*: an oligonucleotide with a non-extendible 3' terminus (or end) that is activatable by pyrophosphorolysis.

Figure 1:
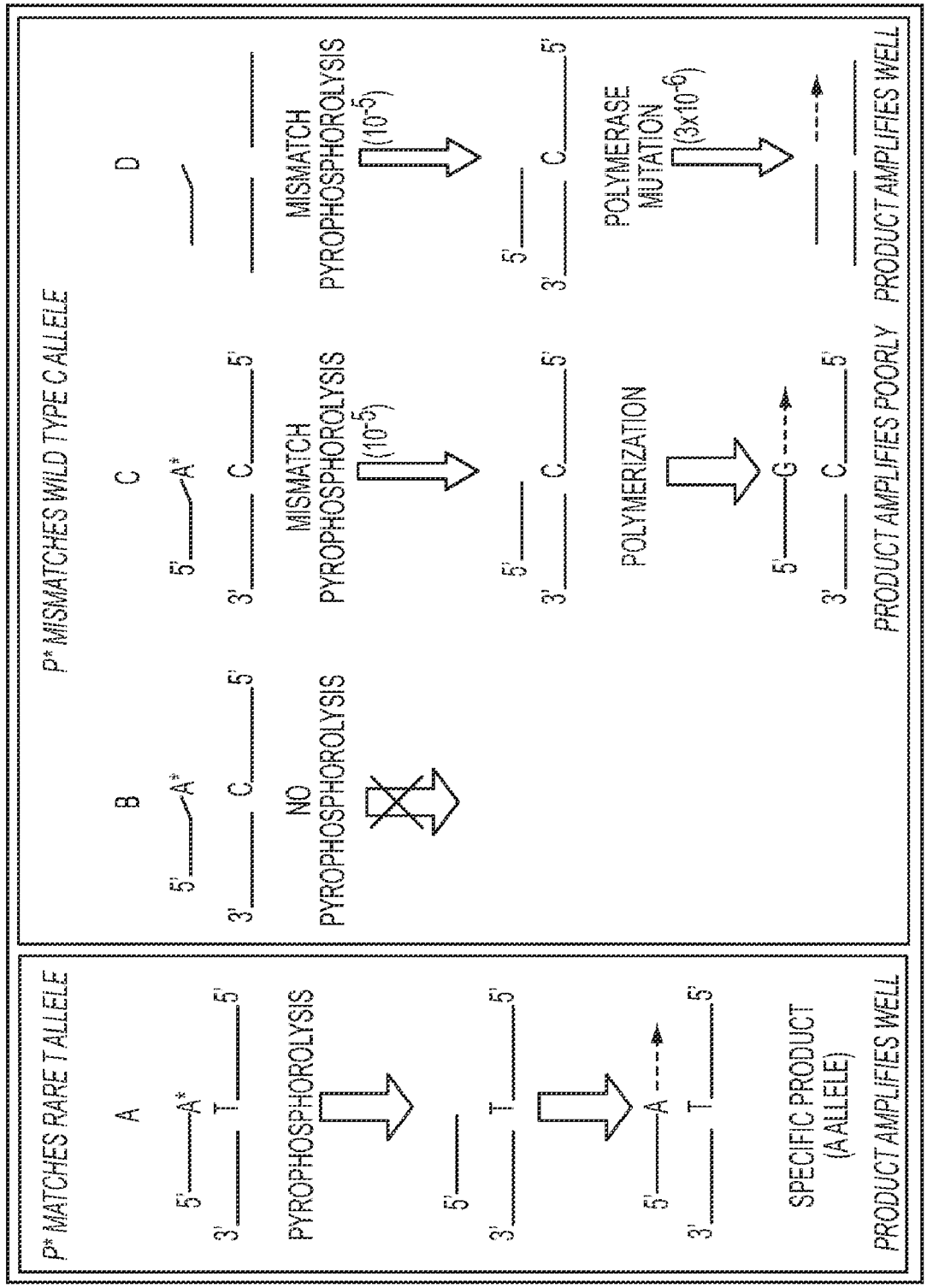
FIG. 1 shows a schematic of the detection of a rare mutation by allele-specific PAP (PAP-A).

PAP-A: PAP-based allele-specific amplification that can be used for detection of rare mutations (FIG. 1).

Bi-PAP-A: PAP-A performed with a pair of opposing P*, i.e., bidirectional (FIG. 2) with at least one nucleotide overlap at their 3' termini.

Figure 3:
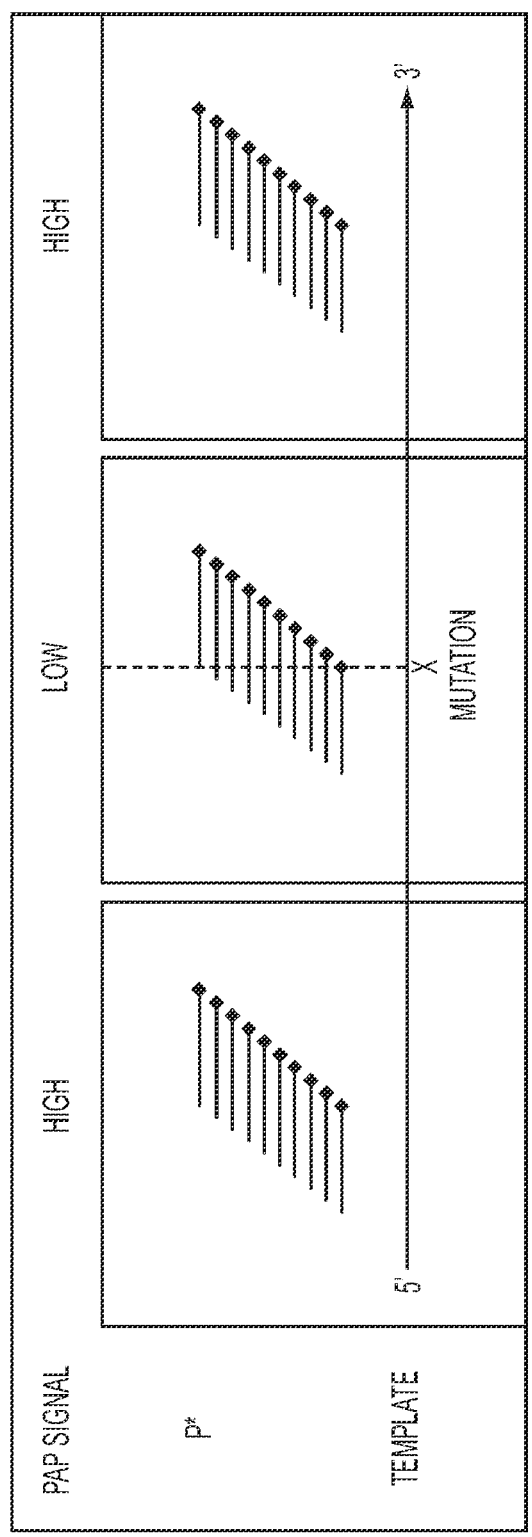
FIG. 3 shows a schematic of PAP-based resequencing (PAP-R) performed on a microarray with programmable photochemical oligonucleotide.
Figure 4:
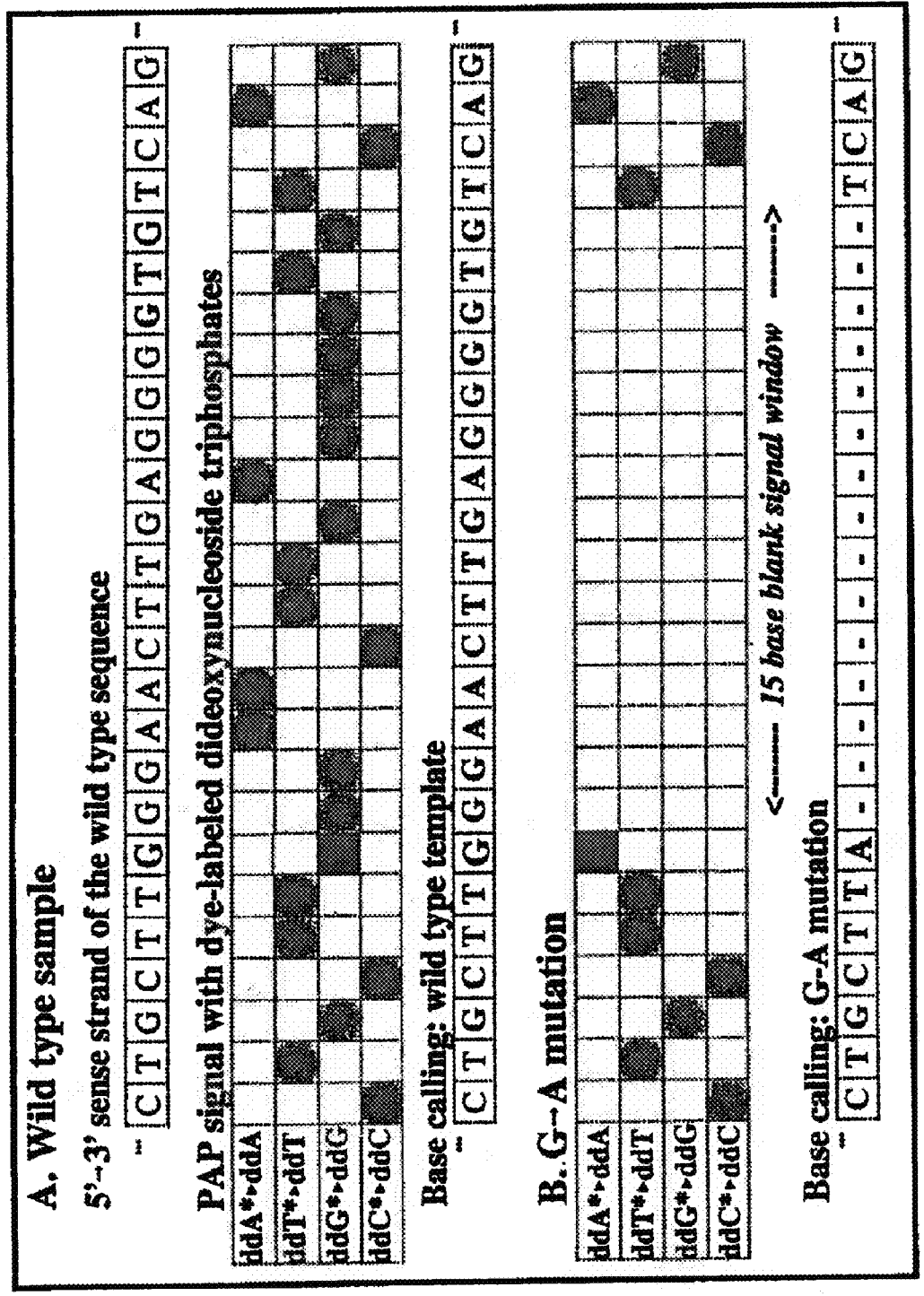
FIG. 4 shows a schematic of microarray-based resequencing to detect a G to A mutation.

PAP-R: PAP-based resequencing for detection of unknown mutations within a known sequence (FIGS. 3 and 4).

LM-PAP: ligation-mediated PAP. The nature of LM-PAP is that the template is synthesized before PAP, such as by ligation reaction or by extension using terminal transferase.

Figure 5:
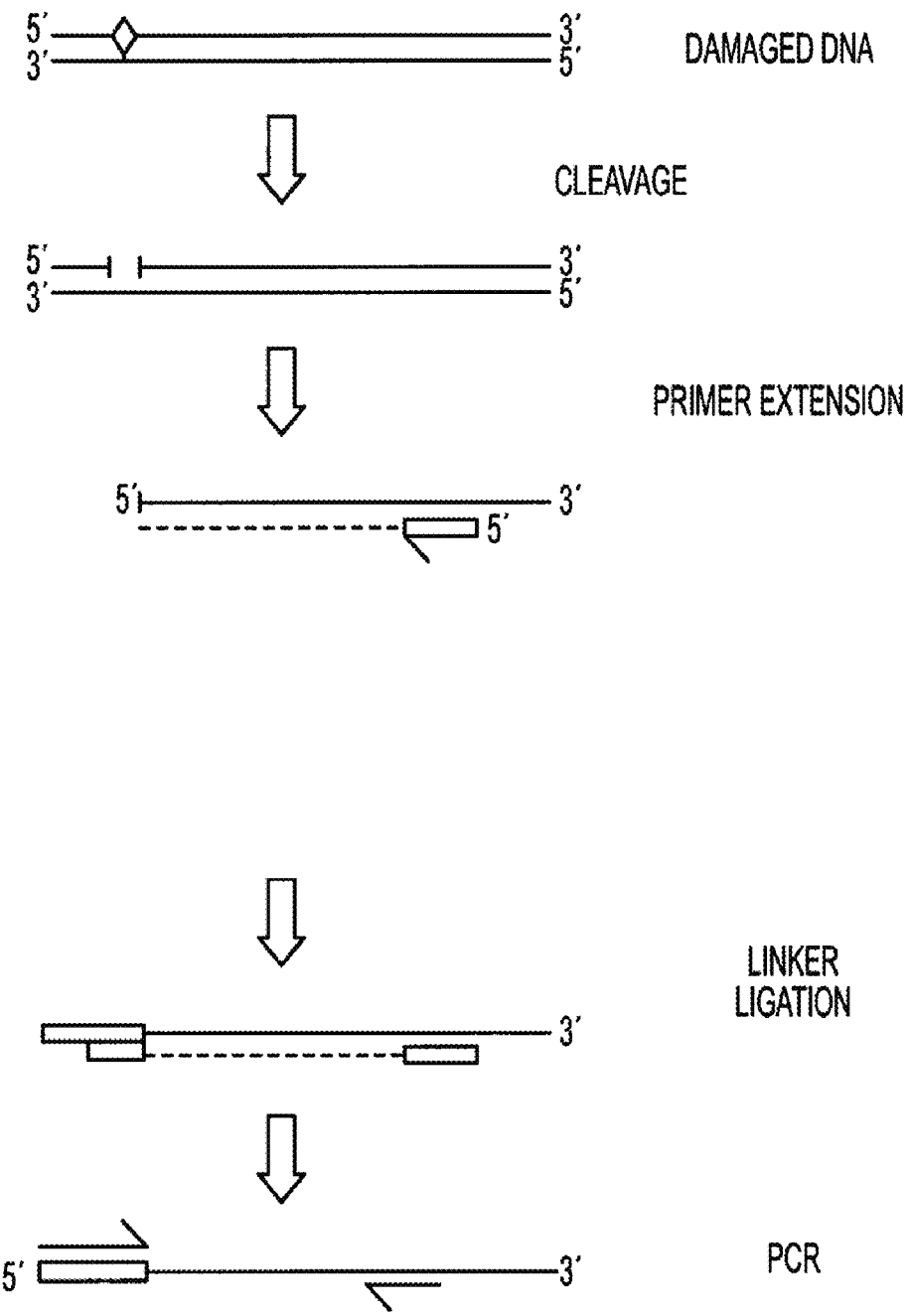
FIG. 5 shows a schematic of ligation-mediated PCR (LM-PCR).

LM-PCR: ligation-mediated PCR (FIG. 5).

$G^v$ or $A^v$ alleles: alleles of the common polymorphism of the dopamine $D_1$ receptor gene that was used as a model system herein (also referred to herein as $G^0$ or $A^0$ alleles).

Linear PAP: PAP with only one P* for linear product accumulation.

Exponential PAP: PAP with two opposing oligonucleotides for exponential product accumulation, and at least one is P*.

Noise rate (%): the relative yield of the mismatched product to the matched product. A specific signal for PAP is defined as a noise rate of less than 10%.

PASA: PCR amplification of specific alleles (also known as allele-specific PCR or ARMS).

Resequencing: scanning for unknown mutations and determining the precise sequence changes within a known sequence. Resequencing is distinguished from de novo sequencing.

Mutation load: the frequency and pattern of somatic mutations within a tissue.

Minimal residual disease: e.g., rare remaining cancer cells in lymph nodes and other neighboring tissues or early recurrence after remission.

Non-extendible 3' terminus (or end): a nucleotide or nucleotide analog at the 3' terminus (or end) of oligonucleotide P* that is non-extendible but that is activatable by pyrophosphorolysis. Examples of non-extendible 3' termini (or ends) include, but are not limited to, a 2'3'-dideoxynucleotide, an acyclonucleotide, 3'-deoxyadenosine (cordycepin), 3'-azido-3'-deoxythymidine (AZT), 2',3'-dideoxyinosine (ddI), 2',3'-dideoxy-3'-thiacytidine (3TC) and 2',3'-didehydro-2',3'-dideoxythymidine (d4T).

Simplex PAP: one PAP (PAP, Bi-PAP, matched or mismatched PAP, and others) in one reaction tube or on a solid support.

Multiplex PAP: more than one PAP (PAP, Bi-PAP, matched or mismatched PAP, and others) in one reaction tube or on a solid support, e.g., microarray.

Matched PAP: PAP having a match between P* and its template.

Mismatched PAP: PAP having a mismatch between P* and its template.

Nested PAP: PAP using two or more pairs of P* in which one pair is located inside a second pair on a template nucleic acid.

Hotstart PAP: PAP in which an essential reaction component is withheld until denaturation temperatures are approached (Charo et al., 1992; Kellogg et al., 1994; Mullis, 1991; D'Aquila et al., 1991). Essential reaction components can be withheld by, e.g., a neutralizing antibody bound to the polymerase, sequestering a component, such as the polymers or $MgCl_2$ in wax, chemically modifying the polymerase to prevent activation until high temperature incubation or separating components by wax.

Truncated Amplification: an amplification method which amplifies non-exponentially, e.g., in a quadratic or geometric manner, with over two chimeric oligonucleotides and produces truncated terminal products that are no more than three rounds of replication from the original template. (Liu et al., 2002).

Reactive 3' OH: is a 3' OH that is capable of being extended by a nucleic acid polymerase or ligated to an oligonucleotide.

DNA polymerases, which are critical to nucleic acid amplification, catalyze some or all of the following reactions: i) polymerization of deoxynucleotide triphosphates or their analogs; ii) pyrophosphorolysis of duplexed DNA in the presence of pyrophosphate (PP), $[dNMP]_n+x[PPi] \ldots [dNMP]_{n-x}+x[dNTP]$; iii) 3'-5' exonuclease activity (which does not require PPi), and iv) 5'-3' exonuclease activity (Duetcher and Kornberg, 1969; Kornberg and Baker, 1992). For Taq and Tfl DNA polymerases, polymerization and 5'-3' exonuclease activity have been reported (Chien et al., 1976; Kaledin et al., 1981; Longley et al., 1990). For T7 Sequenase™ and Thermo Sequenase™ DNA polymerases, pyrophosphorolysis can lead to the degradation of specific dideoxynucleotide-terminated segments in Sanger sequencing reaction (Tabor and Richardson, 1990; Vander Horn et al., 1997).

Pyrophosphorolysis is generally of very minor significance because $PP_i$ is degraded by pyrophosphatase under normal physiological conditions. However, in the presence of high in vitro concentrations of $PP_i$, pyrophosphorolysis can be substantial. For oligonucleotides with a 3' terminal dideoxy nucleotide, only pyrophosphorolysis is possible. Once the dideoxy nucleotide is removed, the activated oligonucleotide can be extended by polymerization.

Pyrophosphorolysis activated polymerization (PAP) offers a novel approach for retrieving a diversity of information from nucleic acids. The exceptional specificity of PAP derives from the serial coupling of two reactions. PAP involves the activation by pyrophosphorolysis of a 3' terminal blocked oligonucleotide (P*) followed by extension of the activated oligonucleotide by DNA polymerization. Operationally, PAP involves the use of an activatable oligonucleotide (P*) in place of a normal oligonucleotide that can be directly extended. Examples of P* include an inactive dideoxy terminated oligonucleotide P* or an inactive chemically modified nucleotide lacking a 3' hydroxyl group, such as an acyclonucleotide, or having a non-extendible nucleotide terminated oligonucleotide P*. Acycloclonucleotides (acycloNTPs) in which the sugar ring is absent are known to act as chain terminators in DNA sequencing (Sanger et al., 1977; Trainor, 1996; Gardner and Jack, 2002). The activation of P* is inhibited by mismatches throughout the length of the oligonucleotide. Mismatches even two nucleotides from the 5' terminus inhibit PAP amplification.

Activation of a P* by pyrophosphorolysis offers extraordinary specificity throughout the length of P*. The enhanced specificity can be used to detect rare known mutations, to elucidate unknown mutations by resequencing, to determine unknown sequence by de novo sequencing, to measure gene expression levels, to compare two sequences, and to increase the specificity of in vivo analysis of chromatin structure. Microarray-based programmable photochemical oligonucleotide synthesis and PAP are synergistic technologies. Thus, the enhanced specificity can be used for rapid, microarray-based resequencing, de novo sequencing, gene expression profiling and SNP detection.

A number of methods for enzymatic nucleic acid amplification in vitro have been developed and can be adapted to detect known sequence variants. These include polymerase chain reaction (PCR) (Saiki et al., 1985; Saiki et al., 1988), ligase chain reaction (LCR) (Landegren, 1998; Barany, 1991) and rolling circle amplification (RCA) (Baner et al., 1998; Lizardi et al., 1998). Herein, we describe pyrophosphorolysis activated polymerization (PAP), an approach that has the potential to enhance dramatically the specificity of PCR allele-specific amplification (Sommer et al., 1989). PAP differs from corrections with PCR in multiple ways: i) the P* oligonucleotide is blocked at the 3' terminus and must be activated by pyrophosphorolysis, ii) pyrophosphorolysis and polymerization are serially coupled for each amplification, iii) PAP may be performed with one P* for linear amplification or with two oligonucleotides for exponential amplification, iv) $PP_i$ is necessary for the amplification, v) significant nonspecific amplification would require the serial coupling of errors of both mismatch pyrophosphorolysis and misincorporation.

The enhanced specificity of PAP relative to PASA is provided by serially coupling pyrophosphorolysis and polymerization. Significant nonspecific amplification requires mismatch pyrophosphorolysis and misincorporation by DNA polymerase, an extremely rare event. For example as described herein, DNA polymerase was utilized to detect the G allele at nucleotide 229 of the $D_1$ dopamine receptor gene. P* was synthesized either with ddA, ddT, ddG or ddC at the 3' terminus. The 3' terminal dideoxynucleotide inhibits direct extension by polymerization, but can be removed by pyrophosphorolysis in the presence of pyrophosphate ($PP_i$) when the P* is specifically hybridized with the complementary strand of the G allele. The activated oligonucleotide can be extended by polymerization in the 5'-3' direction.

Evidence is presented that pyrophosphorolysis followed by polymerization can be used to increase the specificity of PASA. Significant nonspecific amplification with PAP requires the serial coupling of the two types of errors, i.e., mismatched pyrophosphorolysis and misincorporation (FIG. 1). The rate of mismatched pyrophosphorolysis is expressed as the relative rates of removal of a 3' mismatch deoxynucleotide relative to the correct 3' deoxynucleotide. The rate of mismatch pyrophosphorolysis is less than $10^{-5}$ for T7 DNA polymerase (Kornberg and Baker, 1992; Wong et al., 1991). The misincorporation rate to create a substitution mutation by polymerization, expressed as the incorporation rate of an incorrect versus a correct dNMP, was reported to be $10^{-5}$ for T7 DNA polymerase and to be $10^{-4}$ for E. coli DNA polymerase I (Kornberg and Baker, 1992; Wong et al., 1991; Bebenek et al., 1990). Similar results were reported for Taq DNA polymerase, 3'-5' exonuclease-deficient mutants of T7 DNA polymerase and E. coli DNA polymerase I (Kornberg and Baker, 1992; Wong et al., 1991; Bebenek et al., 1990; Eckert and Kunkel, 1990).

PAP is a method of synthesizing a desired nucleic acid strand on a nucleotide acid template strand. In PAP, pyrophosphorolysis and polymerization are serially coupled for nucleic acid amplification using pyrophosphorolysis activatable oligonucleotides (P*). P* is an oligonucleotide that is composed of N nucleotides or their analogs and has a non-extendible nucleotide or its analog at the 3' terminus, such as 3',5' dideoxynucleotide. When substantially hybridized on its template strand, P* could not be extended directly from the 3' terminal nucleotide or its analog by DNA polymerase, the 3' terminal nucleotide or its analog of the P* can be removed by pyrophosphorolysis and then the activated oligonucleotide (<N) can be extended on the template.

The method comprises the following steps carried out serially.

(a) Annealing to the template strand a substantially complementary activatable oligonucleotide P*. This activatable oligonucleotide P* has a non-extendible nucleotide or its analog at the 3' terminus.

(b) Pyrophosphorolyzing the annealed activatable oligonucleotide P* with pyrophosphate and an enzyme that has pyrophosphorolysis activity. This activates oligonucleotide P* by removal of the 3' terminal non-extendible nucleotide or its analog.

(c) Polymerizing by extending the activated oligonucleotide P* on the template strand in the presence of nucleoside triphosphates or their analogs and a nucleic acid polymerase to synthesize the desired nucleic acid strand.

The PAP method can be applied to amplify a desired nucleic acid strand by the following additional steps.

(d) Separating the desired nucleic acid strand of step (c) from the template strand, and (e) Repeating steps (a)-(d) until a desired level of amplification of the desired nucleic acid strand is achieved.

The above PAP method can be applied to allele-specific amplification. The activatable oligonucleotide P* has one or more nucleotides that are not complementary to the template strand. The uncomplimentary nucleotide(s) of P* may locate at the 3' terminus of P*. The above step of (a), (b) or (c) could not occur substantially. As the result, the desired nucleic acid strand is synthesized substantially less.

The above PAP method can be applied with only one activatable oligonucleotide P*. (e) Repeating steps (a)-(d), a desired level of amplification of the desired nucleic acid strand may be achieved linearly. The targeted nucleic acid region outside the annealing region may be of different sizes or of different sequence contexts, so the synthesized nucleic acid strands are of different sizes or of different sequence contexts.

The above PAP method can be applied with two opposing oligonucleotides of which at least one is the activatable oligonucleotide P*. The activatable oligonucleotide P* and the second oligonucleotide are targeted for amplification of a nucleic acid region. Steps (a)-(c) occur to the activatable oligonucleotide P*. The second oligonucleotide is substantially complementary to the other template strand. If the second oligonucleotide is another activatable oligonucleotide P*, steps (a)-(c) occur. If the second oligonucleotide is a regular extendible oligonucleotide, steps (a) and (c) occur: (modified a) annealing to its template strand, followed by (modified c) polymerizing by extending the oligonucleotide on its template strand in the presence of nucleoside triphosphates or their analogs and a nucleic acid polymerase to synthesize the desired nucleic acid strand. (e) Repeating steps (a)-(d), or steps (a), (c) and (d), a desired level of amplification of the desired nucleic acid strand may be achieved, e.g., exponentially. The targeted nucleic acid region between the two annealing regions of the two opposing oligonucleotides may be of different sizes or of different sequence contexts, so the synthesized nucleic acid strands are of different sizes or of different sequence contexts.

LM-PAP involves cleavage, primer extension, linker ligation and PAP that can be applied for analysis of in vivo chromatin structure, such as, methylated state of chromosomes.

LM-PAP may be performed by steps (i), (ii), (iii), (iv) and (v), by steps (i), (ii), (iii) and (vi), by steps (ii), (iii), (iv) and (v) or by steps (ii), (iii) and (vi), where the steps are as follows.

(i) The cleavage occurs chemically, enzymatically or naturally to "breakdown" nucleic acid strands. The nucleic acid usually is genomic DNA that may have lesions or nicks produced in vivo.

(ii) The primer of P1 is gene-specific and its extension includes: 1) annealing to the template strand a substantially complementary primer; 2) extending the primer on the template strand in the presence of nucleoside triphosphates or their analogs and a nucleic acid polymerase, the extension "runs off" at the cleavage site on the template strand. Steps 1) and 2) may be repeated.

The primer extension may be replaced by a P* extension (The above PAP with only one activatable oligonucleotide P*).

(iii) The linker ligation step includes ligation of a linker to the 3' terminus of the synthesized nucleic acid strand. The linker ligation step may be replaced by a terminal transferase extension that is non-template dependent polymerization and an extra nucleic acid sequence is added to the 3' terminus of the synthesized nucleic acid strand.

(iv) PCR is performed with a second gene-specific primer (P2) together with a primer specific for the linker or the added sequence by terminal transferase.

(v) A third gene-specific P* (P3) is used to detect the PCR generated fragments. PAP method is applied with only one activatable oligonucleotide P*. The extension of the activated oligonucleotide P* "runs off" at the end of the template strand generated in step (iv). The PAP method may be applied in allele-specific manners. The activatable oligonucleotide P* may contain one or more nucleotides that are not complementary to the template strand. The uncomplimentary nucleotide(s) of P* may locate at the 3' terminus of P*.

(vi) Instead of steps (iv) and (v), PAP method can be applied with two opposing oligonucleotides of which at least one is the activatable oligonucleotide P*. The activatable oligonucleotide P*(P3) is gene-specific. The second oligonucleotide is specific for the linker or the added sequence by terminal transferase. The second oligonucleotide may be another activatable oligonucleotide P* or a regular primer. The PAP method may be applied in allele-specific manners. The activatable oligonucleotide P* (P3) may contain one or more nucleotides that are not complementary to the template strand. The uncomplimentary nucleotide(s) of P* may locate at the 3' terminus of P* (P3).

FIG. 1 shows detection of a rare mutation by allele-specific PAP (PAP-A). PAP-A can detect a rare allele with extremely high specificity because an allele-specific oligonucleotide with a 3' dideoxy terminus (P*) permits the serial coupling of pyrophosphorolysis and polymerization. For example, if an allele-specific oligonucleotide has a 3' dideoxy terminus (P*) that matches a rare "T" allele, activation occurs by pyrophosphorolytic removal of the dideoxy nucleotide and is followed by polymerization (Situation A). Activation by pyrophosphorolysis does not normally occur with a mismatch at the 3' terminus as with the wild-type "C" allele (Situation B). Rarely, pyrophosphorolysis does occur at a mismatch (estimated frequency $10^{-5}$), but the activated oligonucleotide is extended to produce wild-type sequence (Situation C). A product that supports efficient amplification is generated when mismatch pyrophosphorolysis occurs, a polymerase error that inserts A opposite C in template DNA (Situation D). The frequency of mismatch pyrophosphorolysis coupled with the polymerase mutation is estimated at $10^5 \times 3 \times 10^{-6} = 3 \times 10^{-11}$.

PAP has a potential specificity of $3 \times 10^{-11}$. Approaching this potential requires a design that eliminates confounding sources of error. For example, extension errors from non-blocked upstream oligonucleotides can generate a product with the mutation of interest. If the misincorporation rate for TaqFS is about $10^{-5}$ per nucleotide and only one of the three misincorporations generates the mutation of interest, the error rate is about $3.3 \times 10^{-6}$. Polymerases that contain a proofreading function might have an error rate per specific mutation of $3 \times 10^{-7}$. Polymerases or polymerase complexes with lower error rates would improve specificity further.

One approach utilizes linear PAP. Linear PAP-A may be performed for 40 cycles with only P* in the presence of a fluorescent or radiolabeled ddNTP. A labeled terminated product of defined size will be generated when P* is activated. Linear PAP-A has the advantage of utilizing only the original genomic DNA and eliminating error due to misincorporation from extension of an unblocked upstream primer. However, the sensitivity of detection is limited because the level of amplification is not greater than the number of cycles. For a simple genome like lambda phage, a detection specificity of $10^{-6}$ is possible. The specificity of linear PAP-A depends critically on the absence of unblocked, extendible oligonucleotides. To achieve a robust specificity of $10^{-6}$, unblocked extendible oligonucleotides should be present at $10^{-7}$. This may be achieved by treating gel purified P* (about 99.99% pure with our present protocol) with a 3' to 5' exonuclease to degrade unblocked molecules followed by repurification by gel electrophoresis.

Figure 2:
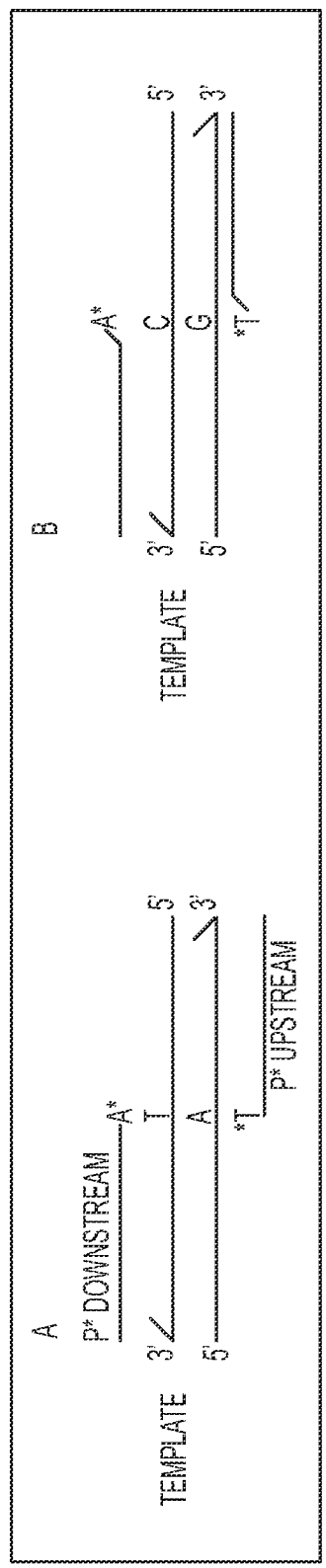
FIG. 2 shows a schematic of bidirectional PAP-A (Bi-PAP-A).

A second approach is bidirectional PAP-A (Bi-PAP-A; FIG. 2). In Bi-PAP-A, both the downstream and upstream oligonucleotides are P*s that are specific for the nucleotide of interest. The P*s overlap at their 3' termini by one nucleotide. This design eliminates extension error from a non-blocked upstream oligonucleotide. This design should not be limited by small amounts of active contaminating oligonucleotide to which the dideoxy terminus has not been added (about 0.01% with our current protocol) because the product generated will be that of a control and will not be a substrate for efficient amplification in subsequent cycles.

Bi-PAP-A generates a product that is the size of a primer dimer. However, it is not a primer dimer in the conventional sense, in that template DNA with a mutation of interest is an intermediate required to generate a product that is an efficient substrate for amplification in subsequent cycles. Bidirectional PAP-A eliminates important bottlenecks to specificity and has the potential to reach a specificity of $10^{-9}$.

As shown in FIG. 2, both the downstream and the upstream P*s are specific for the nucleotide of interest at the 3' termini (an A:T base pair in this example). In the initial round of amplification from genomic DNA, segments of undefined size will be generated. In subsequent rounds, a segment equal to the combined lengths of the oligonucleotide minus one will be amplified exponentially. Nonspecific amplification occurs at lower frequencies because this design eliminates misincorporation error from an unblocked upstream oligonucleotide that can generate the A:T template from a G:C wild-type template with an error rate of $3 \times 10^{-6}$. The P*s may be 30-60 nucleotides for most efficient amplification. Situation A shows that a template with a rare A:T allele will be amplified efficiently. Both the upstream and the downstream P*s are amplified efficiently. Situation B shows that if the DNA template contains the wild-type G:C sequence, neither the downstream nor the upstream P* will be activated substantially.

Rapid resequencing will facilitate elucidation of genes that predispose to cancer and other complex diseases. The specificity of PAP lends itself to resequencing. P*s may be photochemically synthesized on microarrays using flexible digital micromirror arrays.

Microarrays of immobilized DNA or oligonucleotides can be fabricated either by in situ light-directed combinational synthesis or by conventional synthesis (reviewed by Ramsay, 1998; Marshall and Hodgson, 1998). Massively parallel analysis can be performed. Photochemical synthesis of oligonucleotides is a powerful means for combinatorial parallel synthesis of addressable oligonucleotide microarrays (Singh-Gasson et al., 1999; LeProust et al., 2000). This flexible alternative to a large number of photolithographic masks for each chip utilizes a maskless array synthesizer with virtual masks generated on a computer. These virtual masks are relayed to a digital micromirror array. An ultraviolet image of the virtual mask is produced on the active surface of the glass substrate by a 1:1 reflective imaging system. The glass substrate is mounted in a flow cell reaction chamber connected to a DNA synthesizer. Cycles of programmed chemical coupling occur after light exposure. By repeating the procedure with additional virtual masks, it is possible to synthesize oligonucleotide microarrays with any desired sequence. The prototype developed by Singh-Gasson, et al. synthesized oligonucleotide microarrays containing more than 76,000 features measuring 16 square microns.

By combining programmable photochemical oligonucleotide synthesis with digital mirrors and oligonucleotide extension of P*, a high throughput and automated method of resequencing is possible. PAP-R may detect virtually 100% of single base substitutions and other small sequence variants because of its high redundancy; the mismatch spanned by the several overlapping P* oligonucleotides will prevent activation of a cluster of overlapping P*s. One strategy for resequencing is shown in FIGS. 3 and 4. FIG. 3 shows a schematic of PAP-R performed on a microarray with programmable photochemical oligonucleotide: PAP can be used for resequencing to detect unknown mutations. On this microarray, the wild-type template is indicated. The P*s are designed according to the wild-type template. The P*s that overlap with the mutation generate little or no signal indicated as "Low" PAP signal.

FIG. 4 shows an example of solid support-based, e.g., microarray-based, resequencing to detect a G to A mutation. Linear PAP is performed with four different dye-labeled ddNTPs as substrates for single-base extensions. P*s have a specific region of 16 nucleotides within the 3' region of the oligonucleotide. Homozygous or hemizygous DNA template is utilized in the example. Sets of four P*s, with identical sequence except for the four ddNMPs at the 3' terminus, are synthesized for each nucleotide position on the sense strand of the wild-type sequence. The P* with a ddA at the 3' terminus generates a PAP signal at the site of the G-A mutation. The mutation also creates a 15 base "gap" of no PAP signal for the subsequent overlapping 15 sets of P*s. For heterozygous mutation, the P*s with ddA and ddG provide PAP signals. The heterozygous mutation also generates the 15-base "gap" of 50% signal intensity (which is flanked by signals of 100% intensity). For added redundancy with heterozygotes samples, antisense P*s can be utilized (not shown). An unknown single-base substitution can be determined by combination of the two sets of P*s. Small deletions and insertions can be detected and localized.

With 100,000 oligonucleotides per microarray, about 12 kb can be resequenced from downstream and upstream directions. The detection of virtually all mutations requires supplementation of the standard Geniom® instrument software. For wild-type sequence, the signal intensities may vary. Certain oligonucleotides will generate a weaker signal due to secondary structure and other factors. The pattern of signal from wild-type samples should be distinguished reliably from the pattern generated by a given sequence change. The preliminary data suggest that almost all mismatches will inhibit activation dramatically. Because of the redundancy, mutations may be reliably distinguished from the wild-type even if a significant minority of single base mismatches does not inhibit activation substantially.

It is becoming increasingly apparent that in vivo chromatin structure is crucial for mammalian gene regulation and development. Stable changes in chromatin structure often involve changes in methylation and/or changes in histone acetylation. Somatically heritable changes in chromatin structure are commonly called epigenetic changes (Russo and Riggs, 1996) and it is now clear that epigenetic "mistakes" or epimutations are frequently an important contributing factor to the development of cancer (Jones and Laird, 1999).

One of the few methods for assaying in vivo chromatin structure, and the only method with resolution at the single nucleotide level, is ligation-mediated PCR (LM-PCR) (Mueller and Wold, 1989; Pfeifer et al., 1989). LM-PCR has been used to assess chromatin structure, methylation and damaged DNA. FIG. 5 shows a schematic of LM-PCR in which a DNA lesion in the starting DNA is indicated by a small diamond. LM-PCR involves cleavage, primer extension, linker ligation and PCR amplification. LM-PAP is similar to LM-PCR except that activatable oligonucleotide P*s are used.

LM-PCR has proven to be an important technique, now having been used in over 100 published studies (Pfeifer et al., 1999). Many aspects of chromatin structure can be determined by LM-PCR, such as the location of methylated cytosine residues, bound transcription factors, or positioned nucleosomes. Importantly, the structure is determined in cells that are intact and have been minimally perturbed. UV photo-footprinting, for example, is performed by UV irradiating tissue culture cells in a Petri dish, immediately extracting the DNA, and performing LM-PCR to determine the location of thymidine dimers, the formation of which is affected by bound transcription factors.

Allele-specific LM-PAP can be applied to quantitatively determine the level of in vivo methylation. The background of LM-PCR currently limits reliable estimation of the level of methylation. It is generally considered that 0%, 50% and 100% methylation can be determined, but distinguishing finer gradations is not reliable. With a marked reduction in background in LM-PAP, 0%, 20%, 40%, 60%, 80%, and 100% methylation standards may be distinguished reliably. It will be of particular interest to utilize allele-specific LM-PAP to examine the level of methylation in imprinted regions, or in active versus inactive X-chromosomal genes in females. It is anticipated that LM-PAP will decrease the skill and experience needed to examine chromatin structure, thereby facilitating analysis of chromatin structure by more laboratories.

LM-PAP has a diversity of applications. It will be of particular interest to utilize allele-specific PAP to examine differential methylation and chromatin structure in imprinted genes or in active versus inactive X chromosomal genes in females. In addition, the relationship between mutagens, DNA damage, and mutagenesis can be examined.

In PAP, as described above and illustrated herein, pyrophosphorolysis and polymerization by DNA polymerase are coupled serially by using pyrophosphorolysis activatable oligonucleotide. In PAP sequencing, the principle is based on the specificity of PAP and in turn on the base pairing specificity of the 3' specific subsequence. This property of the 3' specific subsequence can be applied to scan for unknown sequence variants, to determine de novo DNA sequence, to compare two DNA sequences and to monitor gene expression profiling.

PAP is highly sensitive to mismatches along the length of P* in PAP with one P* and one opposing unclocked oligonucleotide. The specificity of PAP is also affected by P* length and mismatch. If the allele-specific nucleotide of P* is at the 3' terminus, only the specific allele is amplified and the specificity is not associated with P* length. If the allele-specific nucleotide is not at the 3' terminus of P*, the specificity is associated with P* length. 26 mer P* has a 3' specific subsequence of three-nucleotides within this region any mismatch inhibit the amplification. 18-mer has a 3' specific subsequence of 16 nucleotides.

Bi-PAP is a form of PAP. In Bi-PAP with two opposing P*s, each P* has its own 3' subsequence, i.e., within this region any mismatch inhibit the amplification of Bi-PAP. For example, when the allele-specific nucleotide of the P* pair is at their 3' termini, only the specific allele was amplified, no matter what the lengths of the P*s are 40, 35 or 30 nucleotides. The length of the paired specific subsequence is addition of the P* pair minus one.

The length of the paired specific subsequence may be affected by the sequence context and size of each P*, the type of the 3' terminal non-extendible nucleotide, the template sequence, the DNA polymerase, other components like ions, and cycling conditions. When the template contains repeated sequences or homogenous polymer runs longer than the length of the P* pair, P* may lose specificity for anchoring.

Resequencing is the sequencing of a known region to detect unknown mutations. The property of the paired specific subsequence of Bi-PAP can be applied to scanning for unknown sequence variants or re-sequencing of predetermined sequences in a parallel way.

A Bi-PAP resequencing is shown in FIGS. 22, 23A, 23B, 24A and 24B. Briefly, the wild-type sequence can be determined, and any single base substitution can be determined with the type and position. An unknown small deletion and insertion can be detected and localized. In order to identify a specific type of deletion or insertion, it is possible to add corresponding Bi-PAPs. For fingerprinting, which can provide information regarding mutation position, fewer numbers of Bi-PAPs can be used.

The concept of Bi-PAP de novo DNA sequencing makes use of the complete set of paired specific subsequence of the P* pair to identify the presence of the paired specific subsequence in the de novo sequence.

Figure 25:
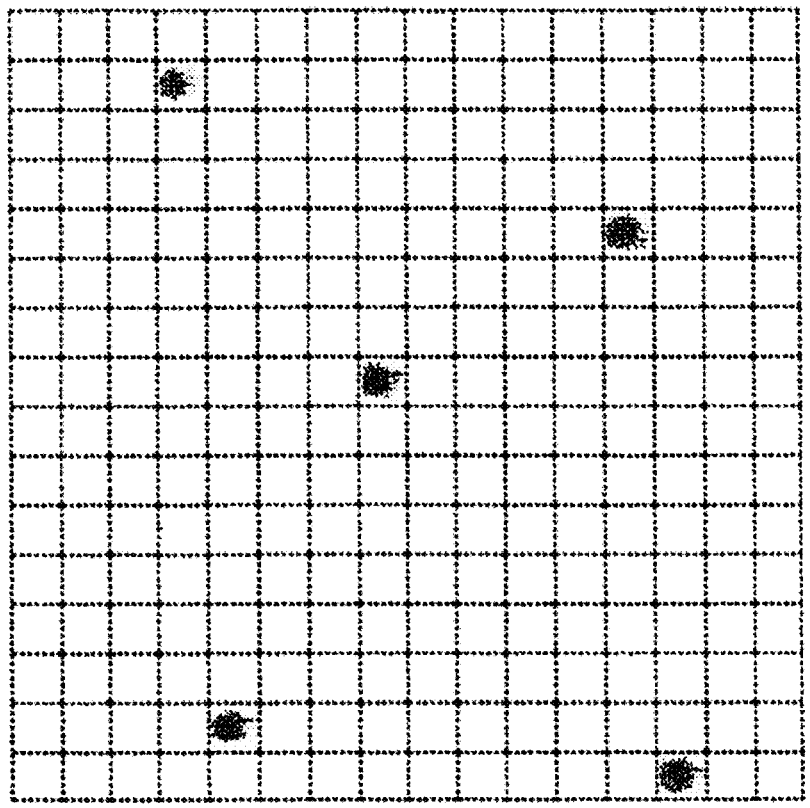
FIG. 25 shows PAP de novo sequencing on microarray. PAP can also be used for de novo DNA sequencing of an unknown region. The paired specific subsequence is supposed to be fifteen nucleotides long. P* pairs of a complete set of the paired specific subsequence are on a microarray with known addresses. After the unknown DNA sample is added, Bi-PAP is performed. All the amplified Bi-PAP products are collected and then the paired specific subsequences of the amplified P* pairs are assembled by one-nucleotide overlapping. Thus, the unknown complementary sequence is reconstructed.

Bi-PAP de novo DNA sequencing on microarray is shown in FIG. 25. Briefly, the procedure first collects all the Bi-PAP amplifications with their P* pairs and then reconstructs the unknown DNA sequence from this collection by ordering the paired specific subsequences.

For comparison of two DNA sequences to see if they are the same or different, there is a simple way to reduce the number of P* pairs by using an incomplete set of the specific subsequences of the P* pair. By arranging them in a particular order, it is possible to identify the chromosomal locations as well as the sequences.

To monitor gene expression profiling, where up to $6 \times 10^4$ to $10^5$ transcripts are expressed and details of the precise sequence are unnecessary, Bi-PAP can be applied. A set of P* pairs which can specifically amplify unique motifs in genes can be designed for Bi-PAP.

This property of the base pairing specificity of Bi-PAP can be applied to scan for unknown sequence variants, to determine de novo DNA sequence, to compare two DNA sequences and to monitor gene expression profiling. A Bi-PAP array is possible. Each pair of two opposing P*s can be immobilized at an individual spot on a solid support, e.g., microarray, thus allowing all the Bi-PAP reactions to be processed in parallel.

For PAP, the activatable oligonucleotide has a non-extendible 3' terminus that is activatable by pyrophosphorolysis (hereinafter referred to as a non-extendible 3' terminus). Any 3' terminal non-extendible oligonucleotide can be used, if it can hybridize with the template strand, the 3' terminal nucleotide can be removed by pyrophosphorolysis, and the activated oligonucleotide can be extended. Examples of non-extendible 3' terminus include, but are not limited to, a non-extendible 3' deoxynucleotide, such as a dideoxynucleotide, or a chemically modified nucleotide lacking the 3' hydroxyl group, such as an acyclonucleotide. Acyclonucleotides substitute a 2-hydroxyethoxymethyl group for the 2'-deoxyribofuranosyl sugar normally present in dNMPs.

Alternative blocking agents may increase the selectivity of pyrophosphoroloysis for a complete match, thereby further enhancing the selectivity of PAP for detecting rare mutations. Finally, alternative blocking agents may be less expensive or more readily automatable, thereby improving the cost-effectiveness of PAP and facilitating PAP microarray-based resequencing.

In addition, P*s not blocked with dideoxynucleotides extends the selection of DNA polymerases which can be used for PAP. As demonstrated herein, Family I polymerases may be used for PAP when the 3' terminal non-extendible oligonucleotide contains a dideoxynucleotide or an acyclonucleotide. Family II polymerases may be used for PAP when the 3' terminal non-extendible oligonucleotide contains an acyclonucleotide.

EXAMPLES

The invention can be understood from the following Examples, which illustrate that PAP can be used to identify a known mutation in a polymorphic site within the human $D_1$ dopamine receptor gene. The effects of the dideoxyoligonucleotide sequences, acyclonucleotide sequences, DNA polymerases, $PP_i$ concentrations, allele-specific templates, pH, and dNTP concentrations were examined. The experiments reported in the Examples were conducted for proof of principle. The following examples are offered by way of illustration and are not intended to limit the invention in any manner. Standard techniques well known in the art or the techniques specifically described therein were utilized.

Example 1

Preparation of Template by PCR

Figure 6A:
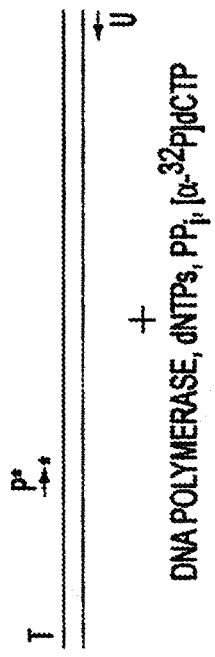
FIGS. 6A and 6B are a schematic illustrating use of PAP to detect the G allele at nucleotide 229 of the $D_1$ dopamine receptor gene. The procedure is described in detail in Example 1 below.

A 640-bp region of the human $D_1$ dopamine receptor gene was amplified by PCR with two primers (T=5' GAC CTG CAG CAA GGG AGT CAG AAG 3' (SEQ ID NO:1) and U=5' TCA TAC CGG AAA GGG CTG GAG ATA 3' (SEQ ID NO:2)) (FIG. 6A). The TU:UT duplexed product spans nucleotides 33 to 672 in GenBank X55760 and the G+C content is 55.3%. A common A to G polymorphism is located at nucleotide 229, resulting in three genotypes of G/G, A/A and G/A (Liu et al., 1995). The PCR mixture contains a volume of 50 µl: 50 mM KCl, 10 mM Tris/HCl, pH 8.3, 1.5 mM $MgCl_2$, 200 µM each of the four dNTPs (Boehringer Mannheim), 0.1 µM of each primer, 2% DMSO, 1 U of Taq DNA polymerase (Boehringer Mannheim) and 250 ng of genomic DNA from G/G homozygote, A/A homozygote or G/A heterozygotes. Cycling conditions included: denaturation at 95° C. for 15 seconds, annealing at 55° C. for 30 seconds, and elongation at 72° C. for one minute, for a total of 35 cycles (Perkin-Elmer GeneAmp PCR system 9600). The PCR product was purified from primers and other small molecules by approximately 10,000-fold by three times of retention on a Centricon® 100 microconcentrator (Amicon). The amount of recovered PCR product was determined by UV absorbance at 260 nm.

Synthesis of P* by Adding a 3'-dideoxynucleotide

The deoxynucleotide oligonucleotide was synthesized by Perseptive Biosystems 8909 Synthesizer (Framinsham) and purified by oligopure cartridges (Hamilton) in the City of Hope DNA/RNA Chemistry Laboratory. The 3' terminal dideoxynucleotide was added by terminal transferase. The mixture contained a total volume of 40 µl: 200 mM potassium cacodylate, 25 mM Tris/HCl (pH 6.6 at 25° C.), 2.5 mM $CoCl_2$, 0.25 mg/ml of BSA, 4000 pM of the oligonucleotide, 2.5 mM 2',3'-ddNTP (the molar ratio of the 3'-OH terminus to ddNTP was 1:25) (Boehringer Mannheim), 125 U of terminal transferase (Boehringer Mannheim). The reaction was incubated at 37° C. for 1 hour and then stopped by adding EDTA at 5 mM final concentration. After desalting by using butanol, the dideoxyoligonucleotide was purified by preparative 7M urea/20% polyacrylamide gel electrophoresis in TBE buffer (90 mM Tris/borate, 1 mM EDTA, pH 8.3) (Maniatis et al., 1982). The amount of the recovered P* was determined by UV absorbance at 260 nm.

Since small amounts of unterminated oligonucleotide would result in non-specificity of pyrophosphorolysis, each dideoxyoligonucleotide was $^{32}$P-labeled at the 5' terminus by T4 polynucleotide kinase and then was electrophoresed through a 7M urea/20% polyacrylamide gel. Only P* products were visible even when the gel was overexposed (data not shown). It is estimated that more than 99.99% of P* contained a dideoxynucleotide at the 3' terminus.

Pyrophosphorolysis Activated Polymerization

A 469-bp region within the TU:UT duplexed template was amplified by PAP with oligonucleotides P* and U, or with only one P* (Table 1 and FIG. 6A). The PU:UP duplexed product corresponds to nucleotides 204 to 672 in GenBank X55760 and the G+C content is 55.6%. Unless stated, the PAP reaction mixture contained a total volume of 25 μl for Tfl DNA polymerase: 75 mM KCl, 20 mM Tris/HCl (pH 7.4), 1.5 mM $MgCl_2$, 40 μM each of the four DNTPs (dATP, dTTP, dGTP and dCTP), 0.2 μM P*, 0.05 μM U oligonucleotide, 300 μM $Na_4PP_i$ (the 20 mM stock solution was adjusted by HCl to pH 8.0), 1 μCi of [$\alpha$-$^{32}$P]-dCTP (3000 Ci/nmole, Amersham), 1 U of Tfl DNA polymerase (Promega) and 2 ng of TU:UT. For Taq DNA polymerase, the reaction mixture was the same except for 50 mM KCl, 10 mM Tris/HCl (pH 7.4), 2.0 mM $MgCl_2$ and 1 U of Taq DNA polymerase (Boehringer Mannheim). The mixtures of PCR and other controls were the same except for the primers added. Cycling conditions included: 94° C. for 15 seconds, 55° C. for one minute, ramping to 72° C. for one minute and 72° C. for two minutes, for a total of 15 cycles.

TABLE 1

Oligonucleotides used in PAP

| Name | Oligonucleotide sequence 5'-3' (SEQ ID NO:) | Purpose |
|---|---|---|
| Template | 5' . . . AATCTGACTGACCCCTATTCCCTGCTT G/A GGAAC . . . 3' (SEQ ID NO: 3) | |
| $D_1$ | ACTGACCCCTATTCCCTGCTT[b] (4) | Control |
| $D_1G*$[a] | ACTGACCCCTATTCCCTGCTTG\*[b] (5) | 3' ddG and G allele specificity co-localized |
| $D_2G*$ | ACTGACCCCTATTCCCTGCTTGG\* (6) | G allele specificity 5' to ddG |
| $D_3G*$ | ACTGACCCCTATTCCCTGCTTGGG\* (7) | G allele specificity 5' to ddG |
| $D_4G*$ | ACTGACCCCTATTCCCTGCTTGGGG\* (8) | 3' ddG mismatches template |
| $D_5G*$ | TCTGACTGACCCCTATTCCCTGCTTG\* (9) | $D_1G*$, with 5' extended bases |
| $D_6A*$ | TGACTGACCCCTATTCCCTGCTTA\* (10) | 3' ddA and A allele-specificity co-localized |
| U | TCATACCGGAAAGGGCTGGAGATA (11) | Upstream oligonucleotide |

| | 3' terminal nucleotide[c] | | Allele-specific nucleotide[d] | | | | Amplification[f] | |
|---|---|---|---|---|---|---|---|---|
| Name | Type | Match | Type | From 3' terminus (bp) | Size (base) | $T_m$ (° C.)[e] | G allele | A allele |
| $D_1$ | dT | Yes | — | +1 | 21 | 64 | Yes | Yes |
| $D_1G*$ | ddG | Yes | G | 0 | 22 | 68 | No | No |
| $D_2G*$ | ddG | Yes | G | −1 | 23 | 72 | No | No |
| $D_3G*$ | ddG | Yes | G | −2 | 24 | 76 | Yes | No |
| $D_4G*$ | ddG | No | G | −3 | 25 | 80 | No | No |
| $D_5A*$ | ddG | Yes | G | 0 | 26 | 80 | Yes | No |
| $D_6A*$ | ddA | Yes | A | 0 | 24 | 72 | No | No |
| U | dA | Yes | — | — | 24 | 72 | Yes | Yes |

[a]$D_1G*$ was produced by adding a G dideoxynucleotide to the 3' terminus of the $D_1$, * = a dideoxynucleotide at the 3' terminus.
[b]The T means the 3' terminus is T deoxynucleotide and G* means the 3' terminus is G dideoxynucleotide. The bold capital G and A are the G and A bases corresponding to G and A alleles, respectively. The first base at the 5' terminus corresponds to nucleotide 208 in GenBank X55760.
[c]The 3' terminal base is a deoxynucleotide or dideoxynucleotide, and creates a match (Yes) or a mismatch (No) with the corresponding base on the complementary strand of the template.
[d]The allele-specific nucleotide is G or A and its distance to the 3' terminus is assigned: 0 = at the 3' terminus, +1 = one base downstream from the 3' terminus, −1 = one base upstream from the 3' terminus, −2 = two bases upstream from the 3' terminus, and −3 = three bases upstream from the 3' terminus.
[e]The $T_m$ for oligonucleotides was estimated to be 4° C. × (G + C) + 2° C. × (T + A) at 1M NaCl (Miyada and Wallace, 1987).
[f]The amplification with U and one P* or with only one P*.

The reaction was electrophoresed through a standard 2% agarose gel. The gel was stained with ethidium bromide for UV photography by a CCD camera (Bio-Rad Gel Doc 1000), dried and subjected to Kodak X-OMAT™ AR film for autoradiography.

Restriction Digestion

Each of the three restriction endonucleases of AciI (5'C▼CGC3'/3'GGC▲G5') EaeI (5'Py▼GGCCPu3'/3'PuCCGG▲Py5') and Eco0109I (5'PuG▼GNCCPy3'/3'PyCCNG▲GPu5') has a restriction site within the PU:UP duplex. The G/G alleles were amplified by PAP with $D_5G^*$ and U; PCR amplification with $D_1$ and U was used as the control. 40 μl of the PAP reaction and 2 μl of the PCR reaction were purified and concentrated with a Centricon® 100 microconcentrator, and the products digested by the restriction endonuclease: 2.5 U of AciI in 1×NE buffer 3; or 3 U of EaeI in 1×NE buffer 1; or 30 U of Eco0109I in NE buffer 4 with BSA (all of the above enzymes and buffers from New England BioLabs). 10 μl of the reaction was incubated at 37° C. for 2 hours. The digestion reaction was electrophoresed through a standard 2% agarose gel as described above.

Principle of PAP

Figure 6B:
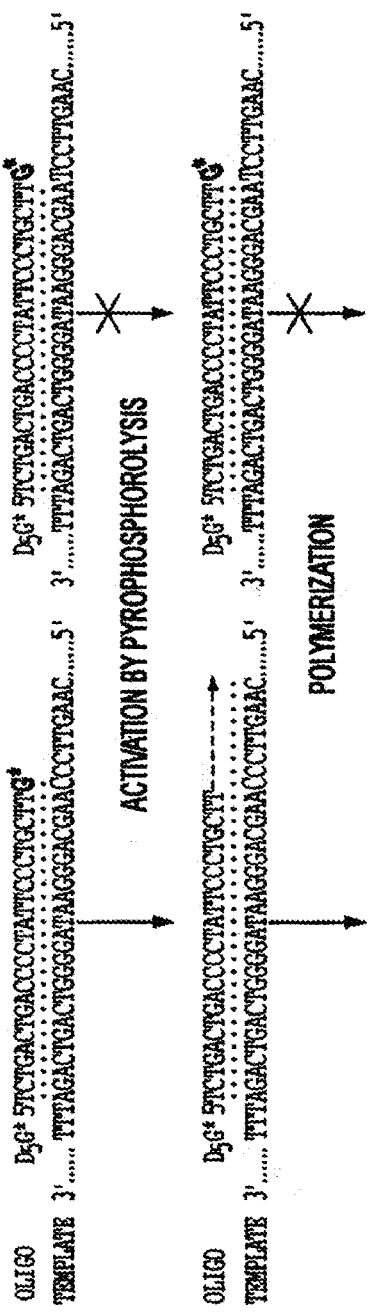
Figure 6C:
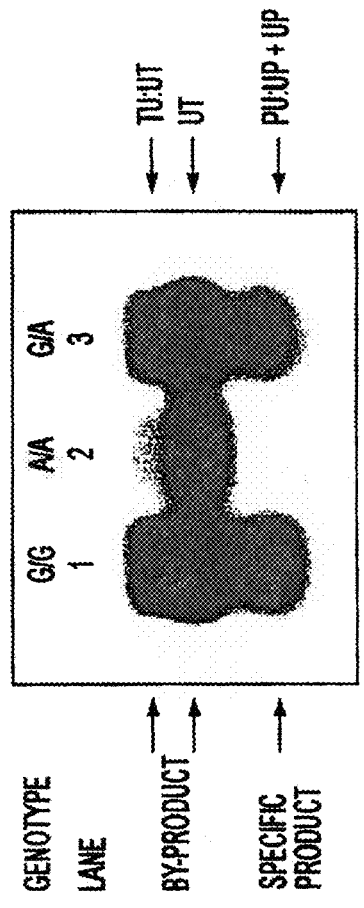
FIG. 6C is an autoradiogram of PAP from the G/G, A/A and G/A genotypes of the human dopamine receptor gene.

Tfl and Taq DNA polymerases were shown to contain pyrophosphorolysis activity. Tfl DNA polymerase was utilized to detect the G allele at nucleotide 229 of the $D_1$ dopamine receptor gene (Liu et al., 1995) (FIG. 6A). P* was synthesized with either ddG or ddA at the 3' terminus (see Table 1). The 3' terminal dideoxynucleotide inhibits direct extension by polymerization, but can be removed by pyrophosphorolysis in the presence of pyrophosphate ($PP_i$) when the P* is specifically hybridized with the complementary strand of the G allele. The degraded oligonucleotide can be extended by polymerization in 5'-3' direction (FIGS. 6B and 6C).

The enhanced specificity of PAP relative to PASA is provided by serially coupling pyrophosphorolysis and polymerization. Significant nonspecific amplification requires mismatch pyrophosphorolysis and misincorporation by DNA polymerase, an extremely rare event (FIG. 7).

Specific Amplification with $D_5G^*$ and $D_3G^*$

Figure 8A:
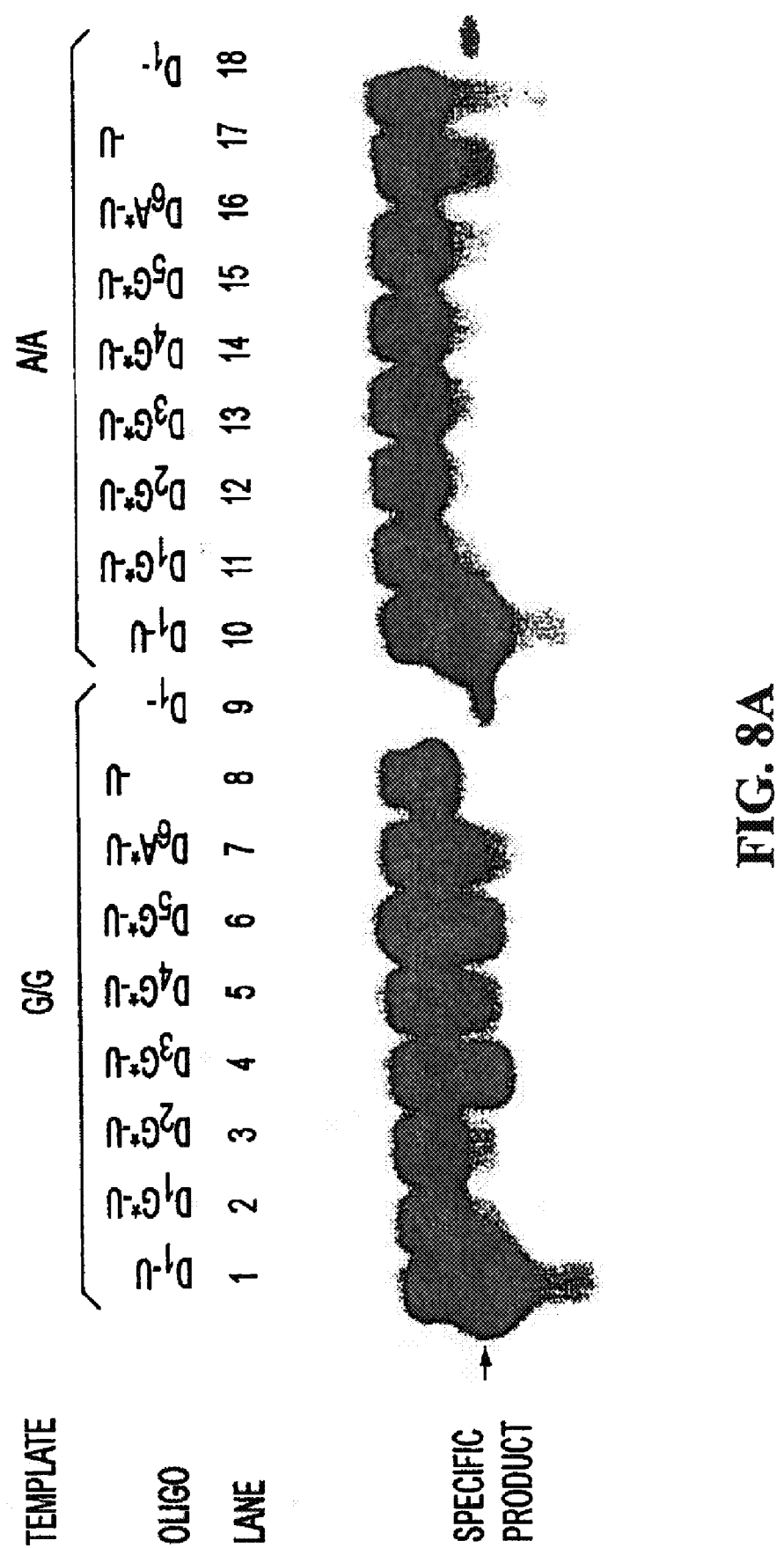
FIGS. 8A and 8B are autoradiograms showing the results of electrophoresis of samples obtained in Example 1 below.
Figure 8B:
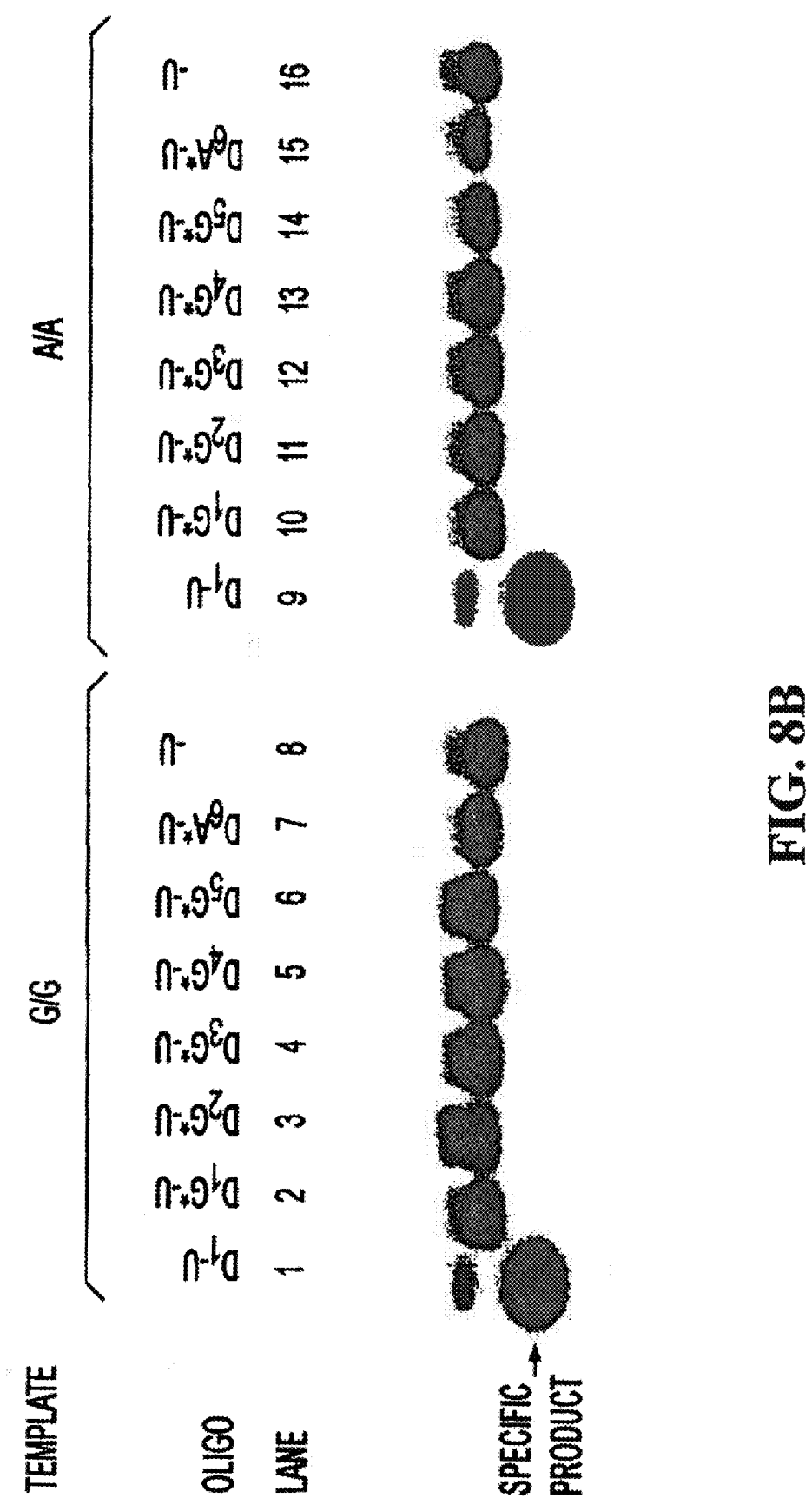

PAP was performed with two oligonucleotides (P* and U), Tfl DNA polymerase and DNA template of the G/G and A/A alleles. Multiple P* were tested (Table 1). $D_5G^*$ (the allele-specific nucleotide and dideoxynucleotide are co-localized to the 3' terminus and $D_3G^*$ (the allele-specific nucleotide is two bases from the 3' terminus) specifically amplified the G allele in the presence of $PP_i$ (FIG. 8A). Without added $PP_i$, no specific product was observed with $D_5G^*$, indicating that added $PP_i$ was an essential component for PAP (FIG. 8B, lanes 6 and 15). Faint products with $D_3G^*$ in lane 4 and with $D_4G^*$ in lane 5 were observed (FIG. 8B) (see below).

Effects of pH, [$PP_i$] and [dNTP] and Enzyme

Each of the above parameters was examined. PAP was most efficient at pH between 7.4 and 7.7, at [$PP_i$] between 200 μM and 400 μM, and at [dNTPs] between 25 μM and 50 μM (Table 2). Taq DNA polymerase can substitute for Tfl with similar efficiencies (Table 2).

TABLE 2

Parameters affecting PAP

| | | PAP efficiency[b] | |
|---|---|---|---|
| Parameter | | $D_5G^*$-U | $D_3G^*$-U |
| pH[a] | 8.1 | – | – |
| | 7.9 | – | – |
| | 7.7 | ++ | +++ |
| | 7.5 | ++ | +++ |
| | 7.4 | ++ | +++ |
| | 7.15 | + | + |
| $PP_i^a$ (μM) | 1000 | – | – |
| | 800 | – | ± |
| | 600 | – | ++ |
| | 400 | ++ | +++ |
| | 200 | ++ | +++ |
| | 0 | – | ± |
| All dNTPs changed[a] (μM) | 200 | – | ± |
| | 100 | – | ± |
| | 50 | ++ | +++ |
| | 25 | ++ | ++++ |
| dGTP changed[a,c] | 100 | ± | ++ |
| | 50 | ± | ++ |
| | 25 | ± | ++ |
| dATP changed[a,c] | 100 | – | + |
| | 50 | – | + |
| | 25 | – | ++ |
| Taq DNA polymerase | G allele and $PP_i$ | ++ | +++ |
| | A allele and $PP_i$ | – | – |
| | G allele and no $PP_i$ | – | ± |

[a]Tfl DNA polymerase was used to amplify the G/G alleles under the conditions in Materials and Methods, except for the factors indicated
[b]The PAP efficiency is indicated as: –, no specific product(s); ±, very weak specific product(s); +, weak specific product(s); ++, moderate specific product(s); +++, strong specific product(s); ++++, very strong specific product(s).
[c]The indicated concentration was changed but the others were kept at 200 μM.

Identity of Specific Products

Figure 9:
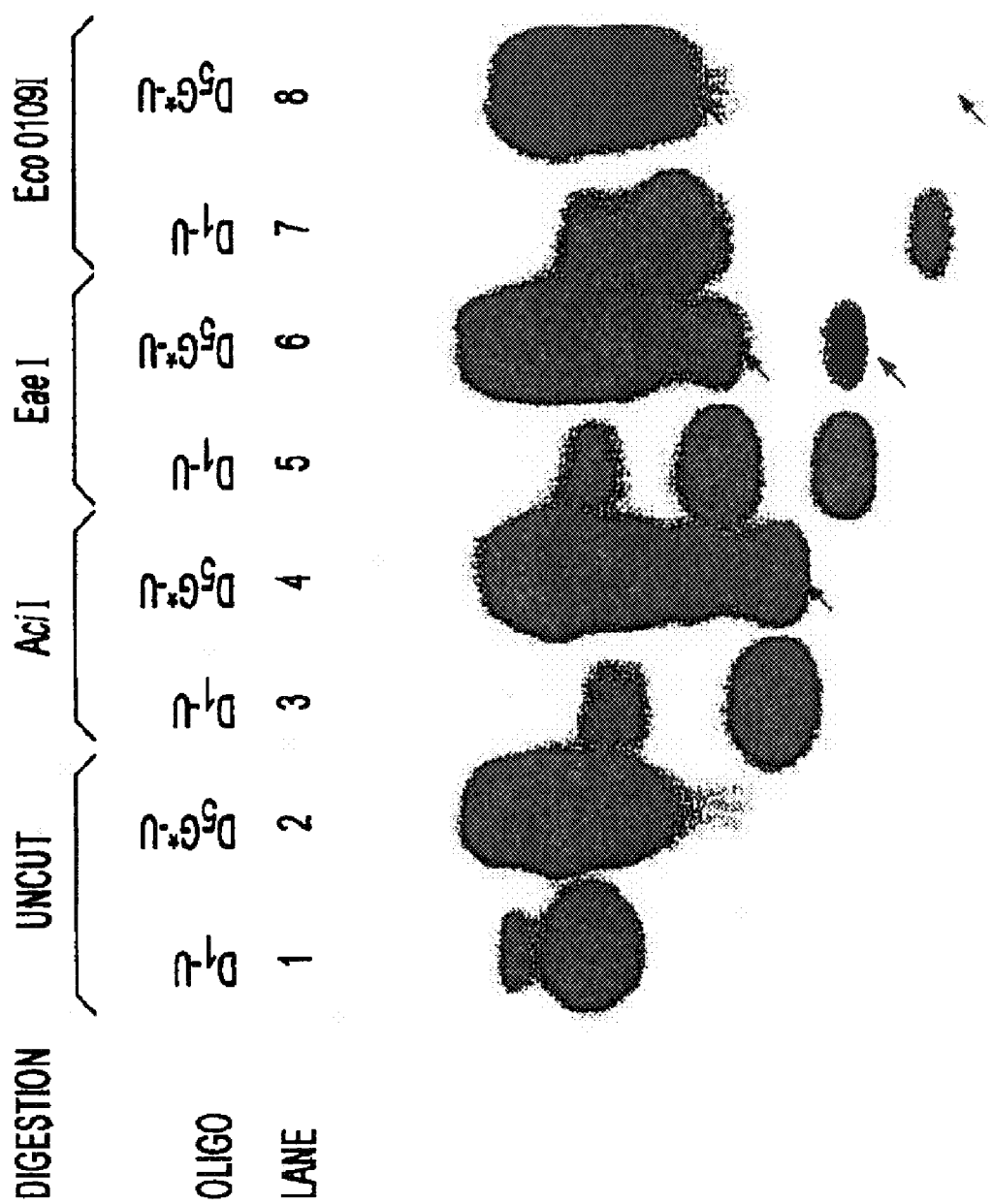
FIG. 9 is an autoradiogram showing the results of electrophoresis of samples obtained in Example 1 below.

In order to confirm the identity of the specific products, restriction endonuclease digestion was performed (FIG. 9). Each of the three restriction endonucleases of AciI, EaeI and Eco0109 has a restriction site with the PU:UP duplex. The expected restriction fragments were found. Similar results were observed with $D_3G^*$ and U.

The specific products of PAP with $D_5G^*$ and U revealed two specific bands on the agarose gel, i.e., PU:UP and UP; because U was more efficient than $D_5G^*$, under our amplification conditions. In order to confirm this, the G/G alleles were amplified by PAP using Tfl DNA polymerase with $D_5G^*$ and U as previously. The products were denatured and electrophoresed through a denaturing polyacrylamide gel. Only one specific band in single-stranded form was observed, indicating that the specific PAP products contain the duplexed and single stranded segments. The same result was observed with $D_3G^*$ and U.

Linear PAP

Figure 10:
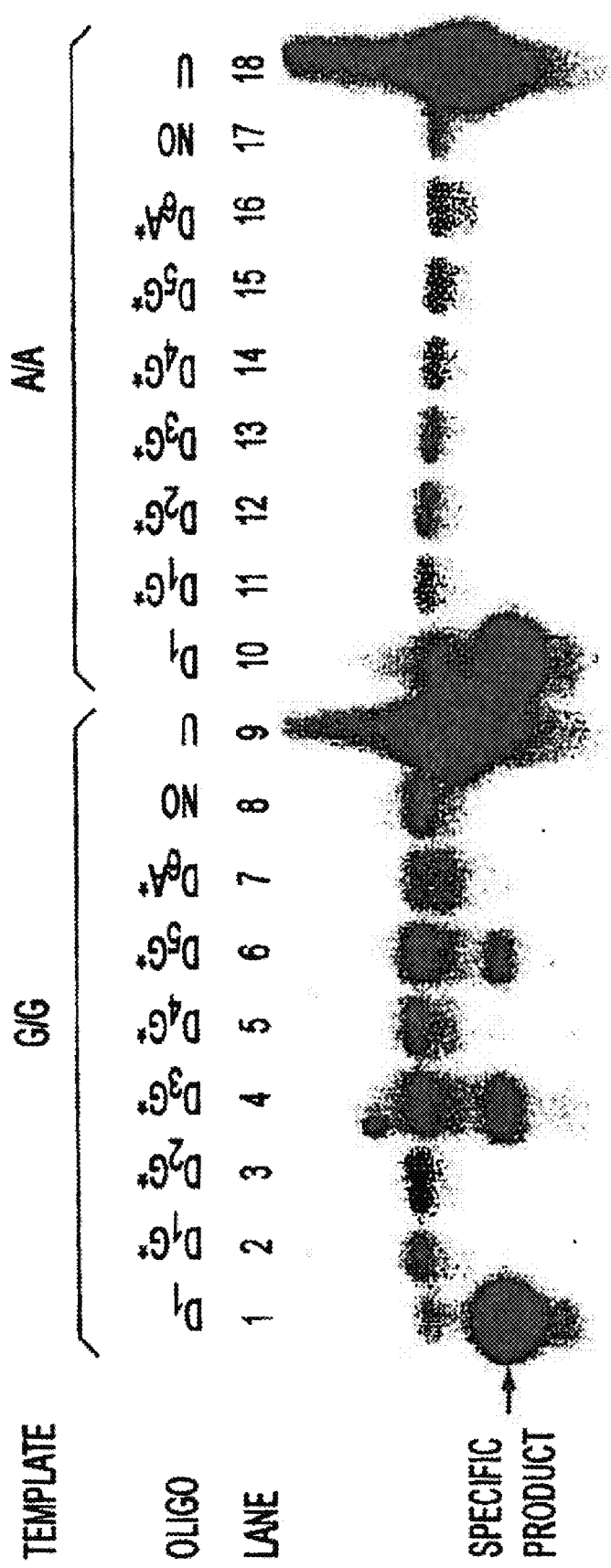
FIG. 10 is an autoradiogram showing the results of electrophoresis of samples obtained in Example 1 below.

PAP was performed for linear amplification with only one P* from the G/G and A/A alleles in the presence of $PP_i$. The specific products of PAP were obtained with $D_3G^*$ and with $D_5G^*$, but not with the other P* (FIG. 10, lanes 4 and 6). The efficiency of P* was affected by the oligonucleotide size, the 3'-terminal dideoxynucleotide and the position of the allele-specific nucleotide.

FIGS. 6A-6C show schematic of PAP. FIG. 6A. A duplexed DNA template TU:UT is amplified with two oligonucleotides P* and U, Tfl DNA polymerase, dNTPs, pyrophosphate and [α-$^{32}$P]-dCTP. P*=pyrophosphorolysis activatable oligonucleotide. In this example P* is $D_5G^*$ and TU:UT is a 640-bp segment of the dopamine $D_1$ receptor gene. FIG. 6B. $D_5G^*$ has a G dideoxynucleotide at the 3' terminus, and it is specific to the complementary strand of the G allele, but mismatches the A allele at the 3' terminus (Table 1). Removal of the dideoxy G by pyrophosphorolysis is followed by polymerization for each amplification. FIG. 6C. Autoradiogram of PAP from the G/G, A/A and G/A genotypes. When the G allele is present, the radioactively labeled specific products of 469 bases (duplex PU:UP and excess antisense strand UP) are produced, since the low rate of pyrophosphorolysis by Tfl polymerase implies that oligonucleotide U has a much higher efficiency than oligonucleotide P*. Electrophoresis for a longer period separates PU:UP from UP. Other products of UT and UT:TU are indicated. Note that TU:UT derives from annealing of excess radioactively labeled UT with non-radioactively labeled TU original template. PAP was also performed with $D_3G^*$ and U from the G/G, A/A and G/A genotypes, and similar results were obtained.

FIGS. 7A-7B show enhanced specificity of PAP with $D_5G^*$. The specificity of PAP is compared with that of PASA to exponentially amplify a template pool of G and A alleles. FIG. 7A. The specific amplification of PASA derives from the high efficiency of primer extension when the primer matches the G allele. The nonspecific amplification results from mismatch extension from the A allele. When this occurs, it results in an efficiency substrate for further amplification. The thickness and position of the arrow represent the amplification efficiency in each cycle. FIG. 7B. The specific amplification of PAP from the G allele occurs at high efficiency. Two types of nonspecific amplifications originate from the A allele: (i) nonspecific amplification can occur at low efficiency by mismatch pyrophosphorolysis resulting in a A:T homo-duplex PU:UP product, which is not an efficient template for subsequent amplification; (ii) nonspecific amplification can occur at extremely low efficiency by both mismatch pyrophosphorolysis and misincorporation to produce a G:T hetero-duplex PU:UP product, but once it occurs, it provides an efficiency template for subsequent amplification. A similar tendency of nonspecific amplifications is suggested for linear amplification by PAP with only $D_5G^*$. It should be noted that allele-specific nucleotide of P*, such as $D_3G^*$, may be near but not at the 3' terminus. In that case nonspecific amplification of PAP requires both mismatch pyrophosphorolysis and mismatch extension. While both variations of PAP should have higher specificity than PASA, the highest specificity is predicted when the 3' terminal dideoxy nucleotide is also the allele-specific nucleotide.

FIGS. 8A-8B show specific amplification with $D_5G^*$ and $D_3G^*$. PAP was performed in the presence (FIG. 8A) or absence (FIG. 8B) of added $PP_i$ with two oligonucleotides for exponential amplification. The oligonucleotides are listed in Table 1. Extension controls with only U identify the positions of TU:UT and UT. Extension controls with $D_1$ identify the position of PU. PCR controls of $D_1$ and U identify the positions of PU:UP and PU:UT. Only 20% of the extension reaction with $D_1$ and the PCR reaction were loaded relative to other lanes.

FIG. 9 shows restriction endonuclease digestion. To show specificity of PAP, samples from the experiment shown in FIG. 8 were digested with AciI, EaeI and Eco0109I restriction endonucleases. Each enzyme has a restriction site within PU:UP. PAP amplified the G/G alleles with $D_5G^*$ and U, and 5% of PCR reaction with $D_1$ and U were taken as control. AciI produces a 236 bp and a 233 bp fragments from PU:UP and a 407 bp and a 233 bp fragments from TU:UT. EaeI produces a 289 bp and a 180 bp fragments from PU:UP and a 460 bp and a 180 bp fragments from TU:UT. Eco0109I produces a 348 bp and a 121 bp fragments from PU:UP and a 107 bp, a 412 bp and a 121 bp fragments from TU:UT. The arrows indicate the digestion products expected from PU:UP.

FIG. 10 shows linear PAP. PAP was performed with only one P* in the presence of added $PP_i$. 20% of the reaction with $D_1$ was loaded relative to other lanes (lanes 1 and 10). No=no oligonucleotide added.

Enhanced Specificity of PAP with $D_5G^*$

Example 1 provides evidence that pyrophosphorolysis followed by polymerization may be used to increase the specificity of PASA. Significant nonspecific amplification requires the serial coupling of the two types of errors (FIG. 7). The mismatch pyrophosphorolysis rate to remove a mismatch deoxynucleotide at the 3' terminus, expressed as the removal rate of an incorrect versus a correct dNMP, was reported at less than $10^{-5}$ for T7 DNA polymerase (Kornberg and Baker, 1992; Wong et al., 1991). The misincorporation rate to create a substitution mutation by polymerization, expressed as the incorporation rate of an incorrect versus a correct dNMP, was reported as to be $10^{-5}$ for T7 DNA polymerase and to be $10^{-4}$ for E. coli DNA polymerase I (Kornberg and Baker, 1992; Wong et al., 1991; Bebenek et al., 1990). Similar results were reported for Taq DNA polymerase and for 3'-5' exonuclease-deficient mutants of T7 DNA polymerase and E. coli DNA polymerase I (Kornberg and Baker, 1992; Wong et al., 1991; Eckert and Kunkel, 1990). The specificity due to the (i) nonspecific amplification in PAP with $D_5G^*$ is estimated to be $10^{-5}$ per cycle, if the mismatch pyrophosphorolysis rate of a ddNMP is the same as dNMP. The specificity due to the (ii) nonspecific amplification is estimated to be $3.3 \times 10^{-11}$, if the mismatch pyrophosphorolysis and the misincorporation are serially coupled.

Essential Components of PAP

Each P* was tested by utilizing Tfl or Taq DNA polymerases to amplify the G/G and A/A alleles. The specific amplification requires the presence of $PP_i$ and allele-specific template. In addition, the amplification efficiency is affected by the oligonucleotide size, the 3' terminal dideoxynucleotide, the position of the allele-specific nucleotide relative to the 3' terminus of P*.

It is not clear why $D_1G^*$ and $D_2G^*$ did not generate the specific signals, but it may be related to a threshold stability of duplex between P* and the template. $D_6A^*$, which contains A dideoxynucleotide at the 3' terminus, did not generate the specific signal, which may be associated with different incorporation efficiencies of ddNTPs by polymerization. Klenow fragment of E. coli DNA polymerase I, Taq DNA polymerase and ΔTaq DNA polymerase incorporate ddGTP more efficiently than other ddNTPs (Sanger et al., 1977; Tabor and Richardson, 1995; Vander Horn et al., 1997). The rate of ddNTP incorporation also varies depending on the template sequence and can be 10-fold higher at some bases relative to others (Sanger et al., 1977). Another possibility is that $D_6A^*$ is shorter in size with a lower $T_m$.

In PAP without added $PP_i$, very faint false signals were generated with $D_3G^*$ and with $D_4G^*$ (FIG. 8B). One possibility is that oligonucleotide dimers can form and trigger nonspecific pyrophosphorolysis of P* in later cycles after "endo-" $PP_i$ is released from the by-polymerization to generate UT. 3' terminal degraded $D_3G^*$ and $D_4G^*$ can be hybridized and extended as false signal. Oligonucleotide dimers were observed with $D_3G^*$ and $D_4G^*$. Another possibility with $D_3G^*$ is that the specific pyrophosphorolysis can occur in later cycles after "endo-" $PP_i$ is released. A third possibility is that $D_3G^*$ and $D_4G^*$ were contaminated by minimal $D_3$ and $D_4$ which were not fully added by G dideoxynucleotide at 3' termini.

Comparison with Other Technologies

A number of methods for enzymatic nucleic acid amplification in vitro have been developed and can be adapted to detect known sequence variants. These include polymerase chain reaction (PCR) (Saiki et al., 1985; Saiki et al., 1988), ligase chain reaction (LCR) (Landegren et al., 1988; Barany, 1991) and rolling circle amplification (RCA) (Lizardi et al., 1998; Banér et al., 1998). PAP is different in many ways: i) pyrophosphorolysis and polymerization are serially coupled for each amplification, ii) there is at least one dideoxyoligonucleotide for PAP. Other chemically modified nucleotides lacking the 3'-hydroxyl group at the 3' terminus, such as acyclonucleotides can serve the same function (see Example 12 below), iii) one format is for linear amplification and the other is for exponential amplification, iv) $PP_i$ is necessary for the amplification, v) significant nonspecific amplification requires both mismatch pyrophosphorolysis and misincorporation, vi) PAP can detect known point mutations and greatly increase the specificity to detect an extremely rare mutant allele from the wild-type allele.

The mechanistic basis is that two or more reactions are serially coupled for amplification with increased specificity. The key component of PAP is a pyrophosphorolysis activatable oligonucleotide. The blocked 3' terminus in these experiments is a dideoxy nucleotide, but any non-extendible nucleotide susceptible to pyrophosphorolysis could in principle be substituted. Indeed, any enzyme that cleaves an oligonucleotide 5' to a mismatch could serve the same function as pyrophosphorolysis activation. For example, a blocked oligonucleotide including the methylated recognition sequence (such as $G^m ATC$) is annealed to its target with the unmethylated recognition sequence, then restriction endonuclease (such as DpnI) can only cleave the methylated site and so activate the oligonucleotide for extension. If a mismatch is located 5' to the cleavage site, significant nonspecific amplification requires the serial coupling of mismatch cleavage and a misincorporation, which is a rare event. Activatable oligonucleotides may also be combined with "minisequencing" primer extension. This may provide a more specific assay for detection of single base changes that might be particularly amenable to chip technology in which specificity can be a problem (Syvanen, 1999). Demonstration that PAP can occur in the linear format (FIG. 10) supports the feasibility of this approach.

Nucleoside triphosphates and 2'-deoxynucleoside triphosphates or their chemically modified versions may be used as substrates for multiple-nucleotide extension by PAP, i.e., when one nucleotide is incorporated the extending strand can be further extended. 2',3'-dideoxynucleoside triphosphates or their chemically modified versions that are terminators for further extension may be used for single-nucleotide extension. 2',3'-dideoxynucleoside triphosphates may be labeled with radioactivity or fluorescence dye for differentiation from the 3' terminal dideoxynucleotide of oligonucleotide P*. Mixtures of nucleoside triphosphates or 2'-deoxynucleotide triphosphates and 2',3'-dideoxynucleoside triphosphates may also be used.

In PAP, specific nucleic acid sequence is produced by using the nucleic acid containing that sequence as a template. If the nucleic acid contains two strands, it is necessary to separate the strands of the nucleic acid before it can be used as the template, either as a separate step or simultaneously. The strand separation can also be accomplished by any other suitable method including physical, chemical or enzymatic means.

When it is desired to produce more than one specific product from the original nucleic acid or mixture of nucleic acids, the appropriate number of different oligonucleotides are utilized. For example, if two different specific products are to be produced exponentially, four oligonucleotides are utilized. Two of the oligonucleotides (P*≧1) are specific for one of the specific nucleic acid sequences and the other two oligonucleotides (P*≧1) are specific for the second specific nucleic acid sequence. In this manner, each of the two different specific sequences can be produced exponentially by the present process.

The DNA or RNA may be single- or double-stranded, may be a relatively pure species or a component of a mixture of nucleic acids, and may be linear or circular. The nucleic acid or acids may be obtained from any source, for example, from plasmid, from cloned DNA or RNA, or from natural DNA or RNA from any source, including bacteria, yeast, viruses, and higher organisms such as plants or animals. DNA or RNA may be extracted from blood, tissue material such as chorionic villi or amniotic cells by a variety of techniques such as that described by Maniatis et al. (1982).

The P* oligonucleotides are selected to be "substantially complementary" to the different strands of each specific sequence to be amplified. Therefore, the P* oligonucleotide sequence need not reflect the exact sequence of the template. For example, a non-complementary nucleotide segment may be attached to the 5'-end of the P* oligonucleotide, with the remainder of the P* oligonucleotide sequence being complementary to the strand. Alternatively, non-complementary bases or longer sequences can be interspersed into the P* oligonucleotide, provided that the P* oligonucleotide sequence has sufficient complementarity with the sequence of the strand to be amplified to hybridize therewith and form a template for synthesis of the extension product of the other P* oligonucleotide. As used in the claims, the term "complementary" should be understood to mean "substantially complementary," as discussed herein.

Any specific nucleic acid sequence can be produced by the present process. It is only necessary that a sufficient number of bases at both ends of the sequence be known in sufficient detail so that two oligonucleotides can hybridize to different strands of the desired sequence at relative positions along the sequence. The greater the knowledge about the bases at both ends of the sequence, the greater can be the specificity of the oligonucleotides for the target nucleic acid sequence, and thus the greater the efficiency of the process. It will be understood that the word oligonucleotide as used hereinafter may refer to more than one oligonucleotide, particularly in the case where there is some ambiguity in the information regarding the terminal sequence(s) of the segment to be amplified.

The present invention can be performed in a step-wise fashion where after each step new reagents are added, or simultaneously, where all reagents are added at the initial step, or partially step-wise and partially simultaneous, where fresh reagent is added after a given number of steps. The simultaneous method may be utilized when an enzymatic means is used for the strand separation step. In the simultaneous procedure, the reaction mixture may contain the strand-separating enzyme (e.g., helicase), an appropriate energy source for the strand-separating enzyme, such as ATP. Additional materials may be added as necessary.

The nucleic acid polymerase may be any compound or system that will function to accomplish the amplification. Suitable enzymes for this purpose include, for example, Tfl DNA polymerase, Taq DNA polymerase, E. coli DNA polymerase I, Klenow fragment of E. coli DNA polymerase I, T4 DNA polymerase, T7 DNA polymerase, other available DNA polymerases, RNA polymerases or their variants, reverse transcriptase or its variants, and other genetic engineered versions. It is predicted on the basis of the relationship between reverse and forward reactions that a DNA polymerase will have high and even pyrophosphorolysis activity for the P* activatable oligonucleotide, if it incorporates ddNTPs efficiently (compared with dNTPs) and evenly (compared among the four ddNTPs). Of all the DNA polymerases, the genetic engineered version may be the best in the future, such as ThermoSequenase (Vander Horn et al., 1997). Generally, the synthesis will be initiated at the 3' end of each oligonucleotide and proceed in the 5' direction on the template strand. However, inducing agents which initiate synthesis at the 5' end and proceed in the other direction can also be used in the PAP method as described above.

Example 2

Preparation of Template by PCR

A 640-bp region of the human $D_1$ dopamine receptor gene was amplified by PCR with two primers (T=5' GAC CTG CAG CAA GGG AGT CAG AAG 3' (SEQ ID NO:1) and U=5' TCA TAC CGG AAA GGG CTG GAG ATA 3' (SEQ ID NO:2)). The TU:UT duplexed product spans nucleotides 33 to 672 in GenBank X55760 and the G+C content of the product is 55%. A common A to G polymorphism is located at nucleotide 229, resulting in three genotypes of G/G, A/A and G/A. The PCR volume is 50 μl: 50 mM KCl, 10 mM Tris/HCl, pH 8.3, 1.5 mM $MgCl_2$, 200 μM each of the four dNTPs, 0.1 μM of each primer, 2% DMSO, 1 U of Taq DNA polymerase (Boehringer Mannheim) and 250 ng of genomic DNA from G/G homozygote, A/A homozygote or G/A heterozygotes. Cycling conditions included: denaturation at 94° C. for 15 sec., annealing at 55° C. for 30 sec., and elongation at 72° C. for one min., for a total of 35 cycles with a GeneAmp PCR System 9600 (Perkin-Elmer Applied Biosystems). The PCR product was purified from primers and other small molecules by approximately 10,000-fold by three times of retention on a Centricons 100 microconcentrator (Amicon). The amount of recovered PCR product was determined by UV absorbance at 260 nm.

Synthesis of P* by Adding a 3' dideoxynucleotide

The deoxynucleotide oligonucleotide was synthesized by Perseptive Biosystems 8909 Synthesizer (Framinsham) and purified by oligopure cartridges (Hamilton) in the City of Hope DNA/RNA Chemistry Laboratory. The 3' terminal dideoxynucleotide was added by terminal transferase. The mixture contained a total volume of 30 μl: 100 mM potassium cacodylate (pH 7.2), 2.0 mM $CoCl_2$, 0.2 mM DTT, 2500 pM of the oligonucleotide, 2 mM 2',3'-ddNTP (the molar ratio of the 3'-OH terminus to ddNTP was 1:24) (Boehringer Mannheim), 100 U of terminal transferase (GIBCO BRL). The reaction was incubated at 37° C. for 4 hr and then stopped by adding EDTA at 5 mM final concentration. After desalting using a Centri-spin™ column (Princeton Separations), P* was purified by preparative 7 M urea/20% polyacrylamide gel electrophoresis in TBE buffer (90 mM Tris/borate, 1 mM EDTA, pH 8.3) (Maniatis et al., 1982). The amount of the recovered P* was determined by UV absorbance at 260 nm.

Since small amounts of unterminated oligonucleotide would result in nonspecificity of pyrophosphorolysis, each P* was $^{32}$P-labeled at the 5' terminus by T4 polynucleotide kinase and then was electrophoresed through a 7 M urea/20% polyacrylamide gel. Only P* products were visible even when the gel was overexposed. It is estimated that more than 99.99% of P* contained a dideoxynucleotide at the 3' terminus. The purity of P* was supported by the absence of PCR product or PAP product at pH 8.3.

Pyrophosphorolysis Activated Polymerization

Regions from 445 to 469 bp within the TU:UT duplexed template were amplified by PAP with oligonucleotides P* and U, or with only P*. The PU:UP duplexed product corresponds to nucleotides 204-228 to 672 in GenBank X55760 and its G+C content is 56%. The PAP reaction mixture contained a total volume of 25 μl: 50 mM KCl, 10 mM Tris/HCl (pH 7.6), 1.5 mM $MgCl_2$, 100 μM each of the four dNTPs (dATP, dTTP, dGTP and dCTP), 0.1 μM P*, 0.1 μM U oligonucleotide (TCATACCGGAAAGGGCTGGAGATA (SEQ ID NO:2)), 300 μM $Na_4PP_i$, 2% DMSO, 1 μCi of [$\alpha$-$^{32}$P] dCTP (3000 Ci/mmole, Amersham), 1 U of AmpliTaqFS DNA polymerase (PE Applied Biosystems) or 0.5 U of each of AmpliTaqFS and Taq DNA polymerases, and 10 ng of TU:UT. ThermoSequenase (Amersham Pharmacia) was also tested under the same conditions except for 8 U ThermoSequenase or 4 U ThermoSequenase plus 0.5 U Taq and 2.5 mM $MgCl_2$. The cycling conditions included: denaturation at 94° C. for 10 sec., annealing at 60° C. for 1 min. (at 55° C. for ThermoSequenase), and elongation at 72° C. for 2 min., for a total of 15 cycles.

The product was electrophoresed through a standard 2% agarose gel. The gel was stained with ethidium bromide for UV photography by a CCD camera (Bio-Rad Gel Doc 1000) and Multi-Analyst® software, dried and subjected to Kodak X-OMAT™ AR film for autoradiography. The PAP yield was quantitated with a PhosphorImager with ImageQuant software (Molecular Dynamics) as the total number of pixels in the PCR band minus the background, indicated as a random unit.

Enhanced PAP Efficiency

In Example 1, only the P* with ddG at the 3' terminus was amplified using native Tfl or Taq DNA polymerase. AmpliTaqFS and ThermoSequenase DNA polymerases were found to achieve much higher PAP efficiency with much less discrimination against any kind of dideoxynucleotide (ddAMP, ddTMP, ddGMP or ddCMP) at the 3' terminus of P*. For example, P*(212)18G$^0$ and P*(212)18A$^0$, which are 18-mers of the dopamine $D_1$ receptor gene but have ddGMP and ddAMP at the 3' termini (Table 3), specifically amplified the G and A alleles, respectively. Their yield ratio was 1.4 (compare lanes 9 with 11 in FIG. 11B), and so P*(212)18G$^0$ is estimated to be 4% more efficient per cycle than P*(212)18A$^0$. Another P*(228)26A$^{-24}$=5' TAGGAACTTGGGGGGTGTCAGAGCCC* 3' (SEQ ID NO:12), which is a 26-mer with ddCMP at the 3' terminus, was amplified as efficiently as a primer without ddCMP at the 3' terminus, and the yield was estimated to be increased 1,000 fold compared with that by using Tfl or Taq. Moreover, PAP amplified segments directly from human genomic DNA.

TABLE 3

PAP specificity affected by P* length and mismatch

| Name | SEQ (SEQ ID NO:) | Mismatch base Type | Distance[c] | $T_m$ (° C.)[d] | Noise ratio (%)[e] |
|---|---|---|---|---|---|
| Template Strand | 5' . . . AATCTGACTGACCCCTATTCCCTGCTT GGAAC . . . 3' (3) | G A | | | |
| P*(204)26G$^{0a}$ | 5'tctgactgACCCCTATTCCCTGCTTG*[b] (13) | G | 0 | 80 | 0.0 |

TABLE 3-continued

PAP specificity affected by P* length and mismatch

| Name | SEQ (SEQ ID NO:) | Mismatch base Type | Mismatch base Distance[c] | $T_m$ (° C.)[d] | Noise ratio (%)[e] |
|---|---|---|---|---|---|
| P*(208)22G[0] | 5'actgACCCCTATTCCCTGCTTG\* (14) | G | 0 | 68 | 0.5 |
| P*(210)20G[0] | 5'tgACCCCTATTCCCTGCTTG\* (15) | G | 0 | 62 | 0.1 |
| P*(212)18G[0] | 5'ACCCCTATTCCCTGCTTG\* (16) | G | 0 | 56 | 0.3 |
| P*(216)26G[-12] | 5'ctattcccTGCTT<u>G</u>GGAACTTGAGGG\* (17) | G | -12 | 80 | 107.1 |
| P*(220)22G[-12] | 5'tcccTGCTT<u>G</u>GGAACTTGAGGG\* (18) | G | -12 | 70 | 95.5 |
| P*(222)20G[-12] | 5'ccTGCTT<u>G</u>GGAACTTGAGGG\* (19) | G | -12 | 64 | 75.8 |
| P*(224)18G[-12] | 5'TGCTT<u>G</u>GGAACTTGAGGG\* (20) | G | -12 | 56 | 7.0 |
| P*(206)26A[-2] | 5'tgactgacCCCTATTCCCTGCTTAGG\* (21) | A | -2 | 80 | 30.4 |
| P*(210)22A[-2] | 5'tgacCCCTATTCCCTGCTTAGG\* (22) | A | -2 | 68 | 3.3 |
| P*(212)20A[-2] | 5'acCCCTATTCCCTGCTTAGG\* (23) | A | -2 | 62 | 2.0 |
| P*(214)18A[-2] | 5'CCCTATTCCCTGCTTAGG\* (24) | A | -2 | 56 | 0.0 |
| P*(206)26G[-9] | 5'tgactgacCCCTATTC<u>G</u>CTGCTTAGG\* (25) | C→G | -9 | 80 | 95.0 |
| P*(210)22G[-9] | 5'tgacCCCTATTC<u>G</u>CTGCTTAGG\* (26) | C→G | -9 | 68 | 88.1 |
| P*(212)20G[-9] | 5'acCCCTATTC<u>G</u>CTGCTTAGG\* (27) | C→G | -9 | 62 | 49.5 |
| P*(214)18G[-9] | 5'CCCTATTC<u>G</u>CTGCTTAGG\* (28) | C→G | -9 | 56 | 4.7 |
| P*(206)26T[-15] | 5'tgactgacCC<u>T</u>TATTCCCTGCTTAGG\* (29) | C→T | -15 | 78 | 89.0 |
| P*(210)22T[-15] | 5'tgacCC<u>T</u>TATTCCCTGCTTAGG\* (30) | C→T | -15 | 66 | 47.8 |
| P*(212)20T[-15] | 5'acCC<u>T</u>TATTCCCTGCTTAGG\* (31) | C→T | -15 | 60 | 3.4 |
| P*(214)18T[-15] | 5'CC<u>T</u>TATTCCCTGCTTAGG\* (32) | C→T | -15 | 54 | 0.0 |

[a] P*(204)26G[0] is a P* with a G dideoxynucleotide at the 3' terminus. "0" means the allele-specific base is at the 3' terminus. The first base at 5' terminus corresponds to nucleotide 204 in GenBank X55760. Its length is 26 bases.
[b] The bold G or A are the G or A allele specific base and the underlined base is designed mismatch.
[c] The distance from the 3' terminus to the allele-specific base: "0" = at the 3' terminus, -3 = three bases from the 3' terminus.
[d] The Tm for oligonucleotide was estimated to be 4° C. × (G + C) + 2° C. × (T + A) under condition of 1M NaCl. The length of each P* is 18 bases.
[e] The noise rate of PAP (%) is defined as the relative yield of non-specific allele product to specific allele product by the same P*, or as the relative yield of the designated mutated P* to its native form by using the same template. A specific signal is denoted as <10% noise rate.

AmpliTaqFS has two mutations compared with native Taq. One mutation in the 5' nuclease domain eliminates 5'-3' exonuclease activity and the second mutation F667Y in the active site (Innis and Gelfand, 1999). ThermoSequenase has the same mutation F667Y in the active site but a deletion of the 5'-3' exonuclease domain (Tabor and Richardson, 1995; Van der Horn et al., 1997). They do not distinguish between dNTP and ddNTP for incorporation. The pyrophosphorolysis of ddNMPs, which is the reverse reaction, is supposed to be much higher and less discriminated by these enzymes. Although either AmpliTaqFS or ThermoSequenase DNA polymerases used was formulated to contain a thermostable pyrophosphatase (manufacturers' instructions) that can hydrolyze $PP_i$ in the reaction so as to decrease PAP efficiency, PAP was still amplified under our conditions. AmpliTaqFS and ThermoSequenase DNA polymerases will work better in their pure form without the contaminated pyrophosphatase.

The 3' Specific Subsequence of P*

Various P*s were examined with different lengths and mismatches using AmpliTaqFS (Table 3). The effect of length and mismatch on PAP efficiency is expressed as the relative yield (%) between two P*s of different lengths from the same template (FIG. 12), which varied from 0.0% to 201.5% with each two to four less bases in length. The specificity of PAP is also affected by P* length and mismatch (Table 3). The noise rate (%) is defined as the relative yield of the mismatch product to the match product, and a specific signal is scored with <10% noise rate. If the allele-specific base of P* was at the 3' terminus, only the specific allele was amplified and the specificity was not associated with P* length (FIG. 12A). If the allele-specific base was not at the 3' terminus of P*, the specificity was associated with P* length. Any non-3'-terminal mismatch in the 18-mer P*, which was up to 15 bases from the 3' terminus, caused no amplification (FIGS. 12B-12E), but even two such mismatches in the 26-mer P* caused non-specific amplification.

Figure 13:
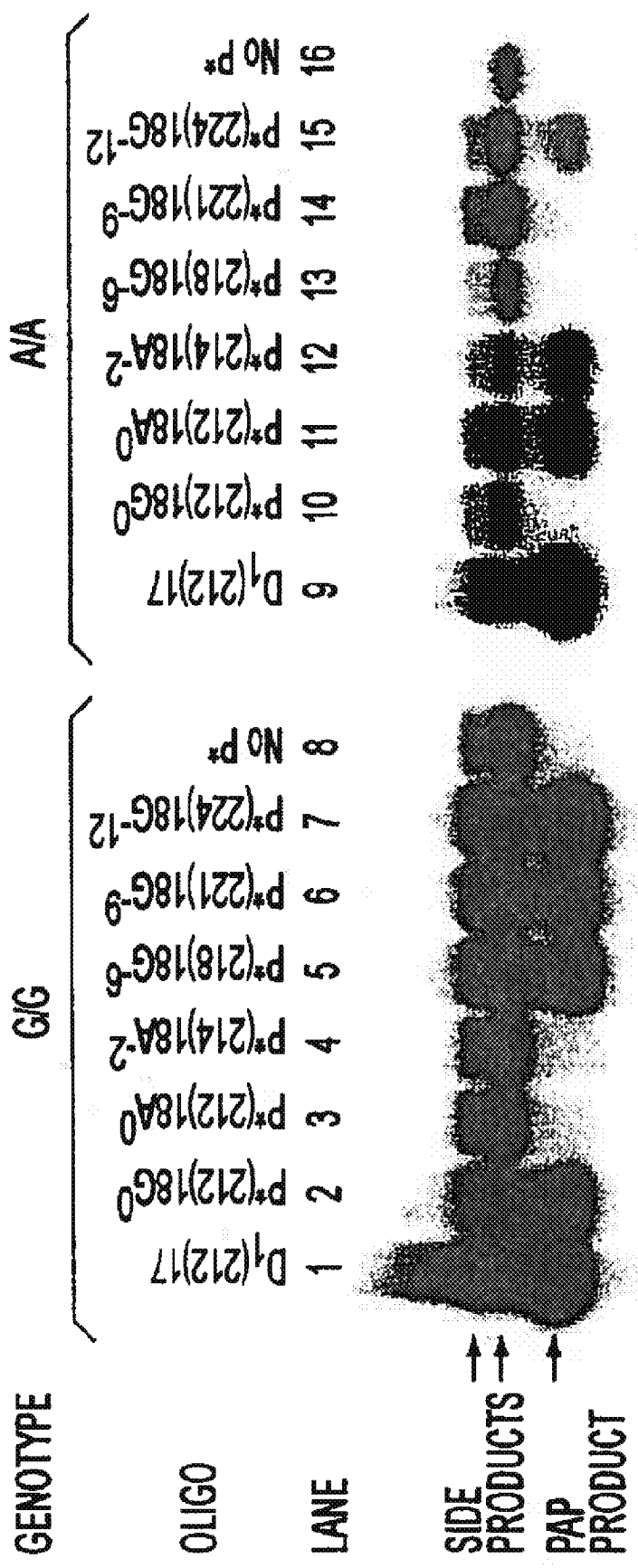
FIG. 13 is an autoradiogram showing the results of electrophoresis of samples obtained in Example 2 below.

The 18-mers were further examined using "stacked" P*s, which span the allele-specific base at different positions (FIG. 13 and Table 4). The noise rate (%) varied from 0.0% to 7.1%. The length of the 3' specific subsequence was ≧13 bases.

TABLE 4

PAP specificity with differently positioned P*s

| Name | Sequence (SEQ ID NO:) |
|---|---|
| Template | 5'GACTGACCCCTATTCCCTGCTT-G/A-GGAACTTGAGGGGTGTC . . . 3' (33) |
| P*(212)18G⁰ | 5'ACCCCTATTCCCTGCTTG* (16) |
| P*(212)18A⁰ | 5'ACCCCTATTCCCTGCTTA* (34) |
| P*(214)18A⁻² | 5'CCCTATTCCCTGCTTAGG* (24) |
| P*(218)18G⁻⁶ | 5'TTCCCTGCTTGGGAACT* (35) |
| P*(221)18G⁻⁹ | 5'CCCTGCTTGGGAACTTGA* (36) |
| P*(224)18G⁻¹² | 5'TGCTTGGGAACTTGAGGG* (37) |

| Name | 3' terminal dideoxxy | Allele-specific base Type | Allele-specific base Distance | Tm (° C.) | Noise rate (%)ᵃ Exponential PAP | Noise rate (%)ᵃ Linear PAP template |
|---|---|---|---|---|---|---|
| P*(212)18G⁰ | ddG | G | 0 | 56 | 2.7 | 0.0 |
| P*(212)18A⁰ | ddA | A | 0 | 54 | 3.8 | 1.1 |
| P*(214)18A⁻² | ddG | A | -2 | 56 | 4.7 | 0.0 |
| P*(218)18G⁻⁶ | ddT | G | -6 | 54 | 0.0 | 0.0 |
| P*(221)18G⁻⁹ | ddA | G | -9 | 56 | 1.7 | 1.7 |
| P*(224)18G⁻¹² | ddG | G | -12 | 56 | 7.1 | 0.6 |

ᵃThe amplification from the G and A templates by PAP with two oligonucleotides or linear PAP with one P*. The noise rate of PAP (%) is the relative yield of the non-specific allele product to the specific allele product.

Similar results were obtained by using P*s which match and mismatch the G allele at different positions (Table 5). The noise rate with one mismatch was various from 0.8% to 5.6%. The length of the 3' specific subsequence was ≧16 bases. The noise rate with two mismatches was 0% (compare lane 2 with lanes 10-15 in FIG. 14).

which every non-specific product is generated from the starting template which requires mismatched pyrophosphorolysis with the 3' terminal mismatched P*, or both mismatched pyrophosphorolysis and mismatched extension with the non-3' terminal mismatched P*.

TABLE 5

PAP specificity with differently mismatched P*s

| Name | Sequence (SEQ ID NO:) | The 3' terminal dideoxy | Mismatchᵃ Type | Mismatchᵃ Distance | $T_m$ (° C.) | Nose rate (%)ᵇ Exponential PAP | Nose rate (%)ᵇ Linear PAP |
|---|---|---|---|---|---|---|---|
| P*(212)18G⁰ | 5'ACCCCTATTCCCTGCTTG* (16) | DdG | | | 56 | 1.0 | 0.0 |
| P*(212)18A⁻³ | 5'ACCCCTATTCCCTGATTG* (38) | DdG | C→A | -3 | 54 | 1.3 | 0.0 |
| P*(212)18G⁻⁶ | 5'ACCCCTATTCCGTGCTTG* (39) | DdG | C→G | -6 | 56 | 0.8 | 0.6 |
| P*(212)18C⁻⁹ | 5'ACCCCTATCCCCTGCTTG* (40) | DdG | T→C | -9 | 58 | 1.8 | 0.4 |
| P*(212)18G⁻¹² | 5'ACCCGATTCCCTGCTTG* (41) | DdG | T→G | -12 | 58 | 5.6 | 1.7 |
| P*(212)18T⁻¹⁵ | 5'ACTCCTATTCCCTGCTTG* (42) | DdG | C→T | -15 | 54 | 3.3 | 1.2 |

ᵃmatch or mismatch with the G allele.
ᵇnoise rate (%) is the relative yield between a mismatched P* and P*(212)18G⁰ with the G allele-specific template.

Linear PAP was examined using only 18 mer P*s and higher specificity was observed with lower noise rate (Tables 4 and 5). Linear PAP takes a different mechanistic pathway in PASA was performed with 17-mer primers without adding a ddNMP at the 3' terminus (see Tables 4 and 5). A mismatched 17-mer primer strongly amplified a nonspecific product with 30% noise rate when the mismatch was as near as 6 bases to 3' terminus, showing a much shorter 3' specific subsequence. Similar results were reported elsewhere previously (Sarkar et al., 1990).

In summary, P* (l-length) has two subsequences: a 3' specific subsequence (n=the number of bases of the 3' specific subsequence≧1) determines the specificity, i.e., within this region any mismatch to its complementary strand of the template results in no substantial amplification; and a 5' enhancer subsequence (m=the number of bases of 5' enhancer subsequence≧0) enhances the amplification efficiency. PAP specificity is co-determined by the base pairing specificity of the 3' specific subsequence, the pyrophosphorolysis specificity and the polymerization specificity. Thus, the base pairing specificity of the 3' specific subsequence is a minimum requirement of the PAP specificity.

The length of the 3' specific subsequence of P* may be affected by the sequence context and size of the P*, the type of the 3' terminal dideoxynucleotide, the template sequence, the DNA polymerase, other components like ion, and cycling conditions. When the template contains repeated sequences>1 or homogeneous polymer runs>1, P* loses specificity for anchoring. The length of the 3' specific subsequence of P* may be affected by the sequence context and size of the P*, the type of the 3' terminal dideoxynucleotide, the template sequence, the DNA polymerase, other components like ion, and cycling conditions. When the template contains repeated sequences>1 or homogeneous polymer runs>1, P* loses specificity for anchoring.

Scanning or Resequencing for Unknown Sequence Variants

The property of the 3' specific subsequence of P* can be applied to scanning for unknown sequence variants or re-sequencing of predetermined sequences in a parallel way. Each nucleotide on the complementary strand of the predetermined sequence is queried by four downstream P*s, such as 18-mers (FIG. 11), which have identical sequence except that at the 3' terminus, either ddAMP, ddTMP, ddGMP or ddCMP corresponds to the wild-type sequence and the three possible single base substitutions. The number of P*s scanning the complementary strand of X bases is multiplication of 4 and X, which is suitable for either exponential or linear PAP. The four downstream P*s can even be immobilized on a single dot when ddAMP, ddTMP, ddGMP and ddCMP at the 3' termini are labeled differently for differentiation, such as by four fluorescence dyes. The amplification signal can thus be represented by intensity decrease of each dye when ddNMP is removed from P* by pyrophosphorolysis. One advantage of linear PAP is that the four ddNTPs can be used as substrates for single base extensions, which are labeled with different dyes for differentiation.

Briefly, if only all the P*s corresponding the wild-type sequence are specifically amplified, the wild-type sequence can be arranged in order by analyzing overlaps. A P* with a single base substitution at the 3' terminus is amplified at the position of hemi- or homo-point mutations. The mutation also creates a "gap" of no PAP signal, which spans a region of several successive nucleotides. For single base substitution, the gap size (bases)+1=the length of the 3' specific subsequence.

Furthermore, we can also scan the sense strand by designing a second set of upstream P*s. An unknown single base substitution can be determined by combination of the two sets of P*s, even in heterozygotes. An unknown small deletion and insertion can be detected and localized. In order to identify a specific type of deletion or insertion, it is possible to add corresponding P*s. For fingerprinting, which can provide information of mutation position, there is a simple stacking way that the stacked region of each two successive P*s<the 3' specific subsequence on the array to reduce the number of P*s by up to n fold.

Determination of De Novo DNA Sequence

The concept of de novo DNA sequencing by PAP makes use of all the possible 3' specific subsequences of P* to identify the presence of the 3' specific subsequence in de novo sequence. A complete set of the 3' specific subsequences of P* is $4^n$. Each of the 3' specific subsequence has a complete subset of the 5' enhancer subsequence of $4^m$. For example, a complete set of 16-mer as the 3' specific subsequence and 2-mer as the 5' enhancer subsequence can be indicated as (A, T, G, C)(A, T, G, C)$N_{16}$=$4^{18}$.

Briefly, the procedure first determines the list of all the specific PAP amplifications and then reconstructs the unknown DNA complementary sequence from this list by ordering the 3' specific subsequences with the given length by using the Watson-Crick pairing rules.

The assembly process is interrupted wherever a given 3' specific subsequence of P* is encountered two or more times. One of the factors influencing the maximum sequencing length is the length of the 3' specific subsequence. The length of a random sequence that can be reconstructed unambiguously by a complete set of the 3' specific subsequence with the given length is approximately the square root of the number of the 3' specific sequence in the complete set with ≧50% possibility that any given 3' specific subsequence is not encountered two or more times. Octamers of the 3' specific subsequence, of which there are 65,536, may be useful in the range up to 200 bases. Decanucleotides, of which there are more than a million, may analyze up to a kilobase de novo sequence. 18 mer P*s containing 16 mer as the 3' specific subsequence, which complete set is $4^{18}$ of P*s, may sequence maximum 77,332 bases.

When there is neighbored known sequence to design an opposite oligonucleotide for PAP with two oligonucleotides. The maximum sequencing length is mainly limited to the opposite oligonucleotide, but not to the length of the 3' specific subsequence of P*, termed Conditional de novo DNA sequencing.

Other Applications for PAP

For fingerprinting which compares two DNA sequences to see if they are the same or different, there is a simple way to reduce the number of P*s by using an incomplete set of the 3' specific subsequences. By arranging them in a particular order, it is possible to identify the chromosomal locations as well as sequences. Considering the $3 \times 10^9$ bp DNA in human genome, PAP with two oligonucleotides is preferred over PAP with only one P* to increase the specificity.

To monitor gene expression profiling, where up to $6 \times 10^4$ to $10^5$ transcripts are expressed and details of the precise sequence are unnecessary, PAP with only one P* can be applied and a set of P* which identify unique motifs in genes can be designed with a total length of up to 22-mer. Between each two P*s, there is at least a sequence difference at the 3' terminus or ≧2 sequence differences at the non-3' terminus.

Comparison with Sequence by Hybridization

In SBH by using oligonucleotide, the DNA sequence is determined by the hybridization and assembly of positively hybridizing probes through overlapping portions. It has been known for a long time that a single oligonucleotide hybridization on a immobilized sample can be very specific in optimal hybridization and washing conditions (Wallace et al., 1979), thus it is possible to discriminate perfect hybrids from ones containing a single internal mismatch. The oligonucleotides in array are 11-20 nucleotides in length and have 7-9 bases specific region in the middle, the non-specific signal is generated by mismatched hybridization. Under standard hybridization and washing conditions, the duplex stability between match and mismatch is also affected by the terminal mismatch and the flanking sequence (Drmanac et al., 1989; Khrapko et al., 1989; Ginot, 1997).

SHB can be modified with enzymes in several ways (Miyada and Wallace, 1987; Southern, 1996). Primer extension by DNA polymerase incorporates bases one at a time only if they match the complement strand. Ligase has similar requirements: two oligonucleotides can be joined enzymatically provided they both are complementary to the template at the position of joining.

FIGS. 11A-11B show the enhancement of PAP efficiency. FIG. 11A. PAP is amplified with two oligonucleotides P* and U from duplex TU:UT template. Each of the four P*s has a ddA, ddT, ddG and ddC at the 3' terminus. The 3' terminal base is either specific to the complementary strand of the G or A alleles, or not matched. FIG. 11B. Autoradiogram of PAP from the G/G, A/A and G/A genotypes of the human dopamine receptor gene. The radioactively labeled specific products of 461 bases (duplex PU:UP and excess antisense strand UP) are produced. Other side products UT and UT:TU are indicated. Note that TU:UT derives from annealing of excess radioactively labeled UT with non-radioactively labeled TU original template.

Figure 12B:
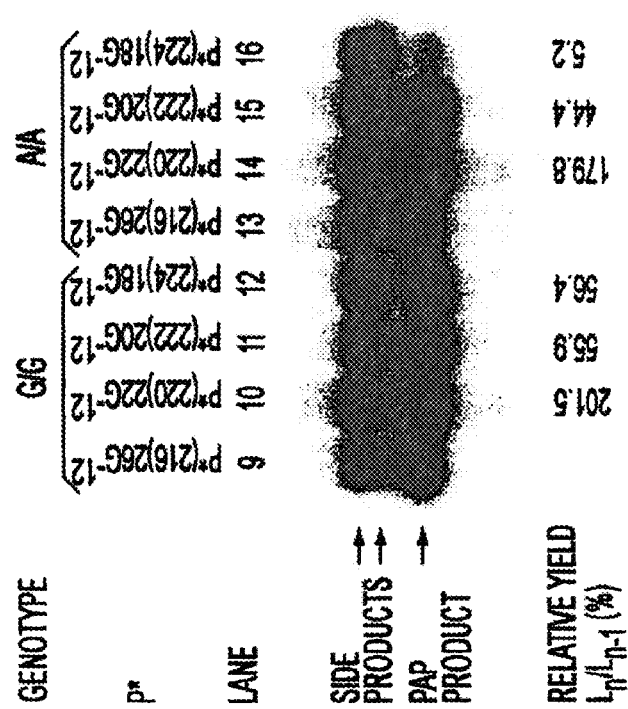
Figure 12A:
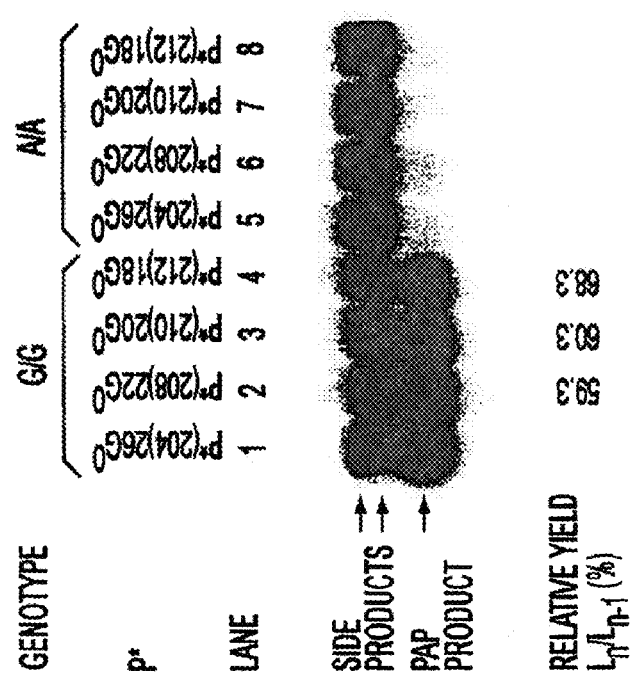

FIGS. 12A-12E show the effect of P* length and mismatch on PAP efficiency. PAP was amplified with P* and U oligonucleotide (see Table 3). In each of FIGS. 12A-12E, P*s have the sample 3' termini but are different in length. FIG. 12A. In lanes 1-4, the P*s matched and amplified the G allele. In lanes 5-8, the P*s mismatched at the 3' termini but amplified the A allele. FIG. 12B. In lanes 9-12, the P*s matched and amplified the G allele. In lanes 13-16, the P*s mismatched at –12 bases to the 3' termini but amplified the A allele. FIG. 12C. In lanes 17-20, the P*s matched and amplified the A allele. In lanes 21-24, the P*s mismatched at –2 bases to the 3' termini but amplified the G allele. FIG. 12D. In lanes 25-28, the P*s mismatched at –9 bases to the 3' termini but amplified the A allele. FIG. 12E. In lanes 29-32, the P*s mismatched at –15 bases to the 3' termini but amplified the A allele. The length effect is indicated as the yield ratio in one lane ($L_n$) to the previous lane ($L_{n-1}$). The length effect was not shown in lanes 5-8 because the signals are at or close to the background.

FIG. 13 shows PAP specificity with differently positioned P*s. PAP was amplified with a P* and U oligonucleotide (see Table 4). The P* matched to and amplified the G allele in lanes 2-7, but mismatched to and amplified the A allele in lanes 9-15. Lanes 1 and 9 were PCR control with $D_1$(212)17 mer and U. Lanes 8 and 16 were extension control with only U.

Figure 14:
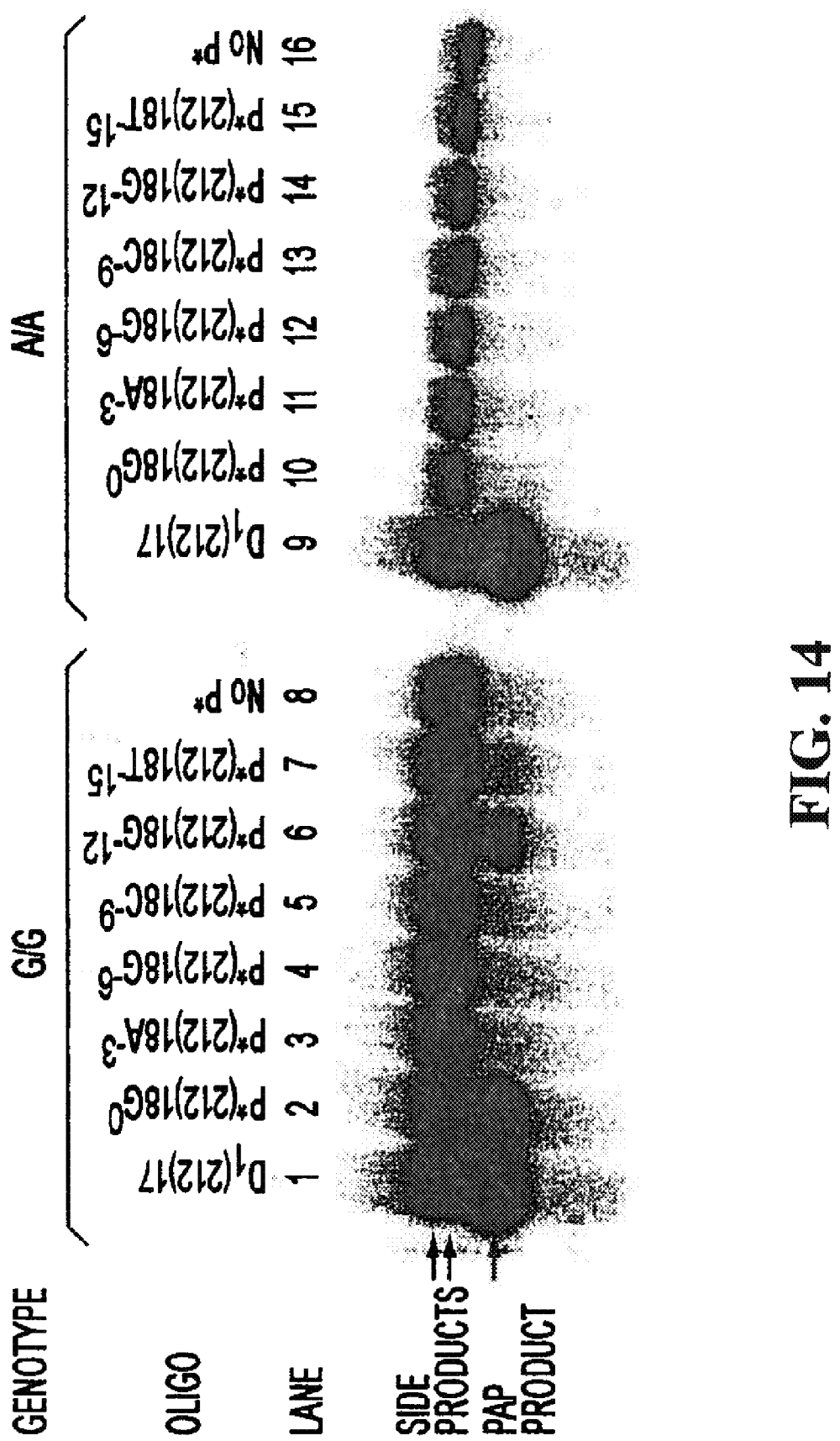
FIG. 14 is an autoradiogram showing the results of electrophoresis of samples obtained in Example 2 below.

FIG. 14 shows PAP specificity with differently mismatched P*s. PAP was amplified with a P* and U oligonucleotide (see Table 5). In lanes 2-7, the P* amplified the G allele with match or one mismatch. In lanes 9-15, the P* amplified the A with one or two mismatches. Lanes 1 and 9 were PCR control with $D_1$(212)17 mer and U. Lanes 8 and 16 were extension control with only U.

Example 3

PAP Amplification from Genomic DNA

Figure 15:
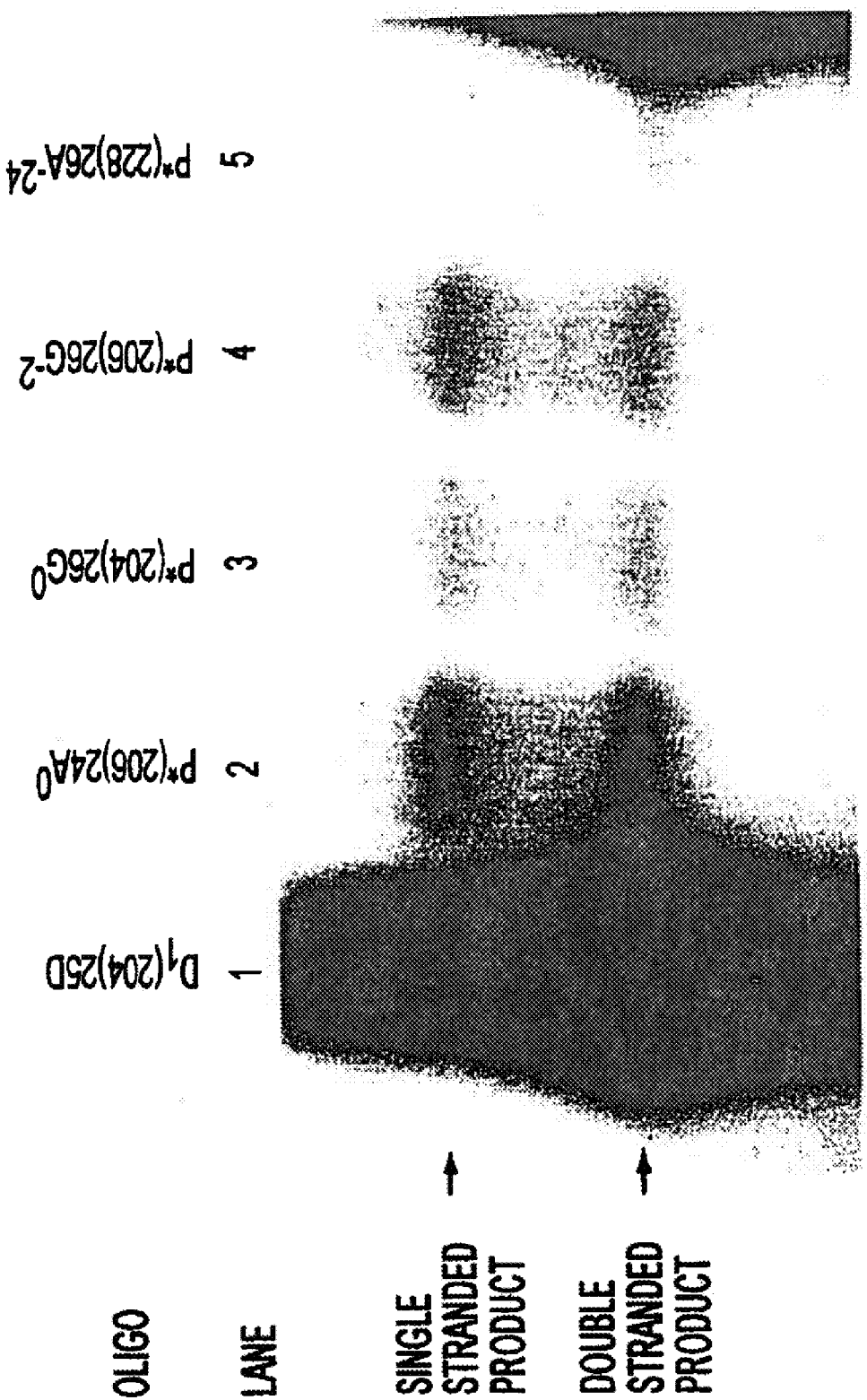
FIG. 15 is an autoradiogram showing the results of electrophoresis of samples obtained in Example 3 below.

This example illustrates PAP amplification directly from genomic DNA. The oligonucleotides used in this example are listed below. Lane numbers refer to lanes in FIG. 15.

The downstream oligonucleotides in 0.1 µM concentration are:

```
Lane 1:
                                    (SEQ ID NO: 43)
D₁(204)25D    5' TCTGACTGACCCCTATTCCCTGCTT 3'

Lane 2:
              (A allele specific; SEQ ID NO: 44)
P*(206)24A⁰   5' TGACTGACCCCTATTCCCTGCTTA* 3'

Lane 3:
              (G allele specific; SEQ ID NO: 45)
P*(204)26G⁰   5' TCTGACTGACCCCTATTCCCTGCTTG* 3'

Lane 4:
              (G allele specific; SEQ ID NO: 46)
P*(206)24G⁻²  5' ACTGACCCCTATTCCCTGCTTGGG* 3'

Lane 5:
              (A allele specific; SEQ ID NO: 47)
P*(228)26A⁻²⁴ 5' TAGGAACTTGGGGGGTGTCAGAGCCC* 3'
```

The opposite upstream oligonucleotide in 0.1 µM concentration is: $D_1$(420)24U 5' ACGGCAGCACAGACCAGCGT-GTTC 3' (SEQ ID NO:48), which was paired with each downstream oligonucleotide. See Footnotes of Table 3 for details.

The other components were the same as in Example 2, except for the following: 0.5 U of each of AmpliTaqFS and Taq DNA polymerases, and 100 ng of heterozygous G/A allelic genomic DNA were used per 25 µl reaction by using 30 cycles.

The PAP product size range from 193 bp to 218 bp. One double stranded and one single stranded product was observed on the gel, indicating the exhaust of $PP_i$ hydrolyzed by the contaminated thermostable pyrophosphatase.

Example 4

Comparison of Specificity of LM-PCR and LM-PAP

The LM-PCR protocol includes primer extension, linker ligation, PCR amplification, and directed labeling in the human dopamine $D_1$ receptor gene model system (FIG. 16). LM-PCR was performed with the addition by terminal deoxynucleotidyl transferase (TdT) (this protocol is known as TD-PCR) on UV-treated genomic DNA samples essentially as described (Pfeifer et al., 1999), except that $Vent_R$ (exo-) DNA polymerase was used in the first 10 cycles of primer extension (P1 primer=5' TTGCCACTCAAGCG-GTCCTCTCAT 3' (SEQ ID NO:49)). Temperature cycles were 1 min at 95° C., 3 min. at 63° C., and 3 min at 72° C. To enhance the signal, terminal transferase was added to the protocol, and this variation of LM-PCR is called TD-PCR. Dynabeads were used to enrich target DNA molecules before terminal deoxynucleotidyl transferase (TdT) tailing. PCR was performed using Expand Long Template PCR System 3 (BMB) as described by the manufacturer (P2 primer=5' GAAGCAATCTGGCT GTGCAAAGTC 3' (SEQ ID NO:50)). The PCR products were purified using QIAquick PCR Purification Kit (QIAGEN) before performing the direct labeling. A portion of the cleaned PCR product was used for direct labeling with AmpliTaq DNA Polymerase (Perkin-Elmer) with $^{32}$P labeled primers:

```
P3A:
(5' TCTGACTGACCCCTATTCCCTGCTTA 3'
(SEQ ID NO: 51; the 3' terminal deoxynucleotide
is A allele specific)
and
```

-continued

P3G:
(5' TCTGACTGACCCCTATTCCCTGCTTG 3'
(SEQ ID NO: 52; the 3' terminal deoxynucleotide
is G allele specific).

Figure 16B:
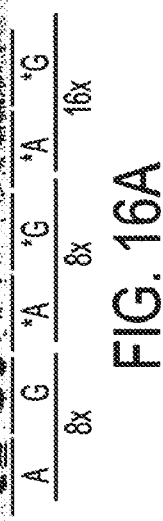
FIGS. 16A-16B show UV footprinting by LM-PAP.
Figure 16A:
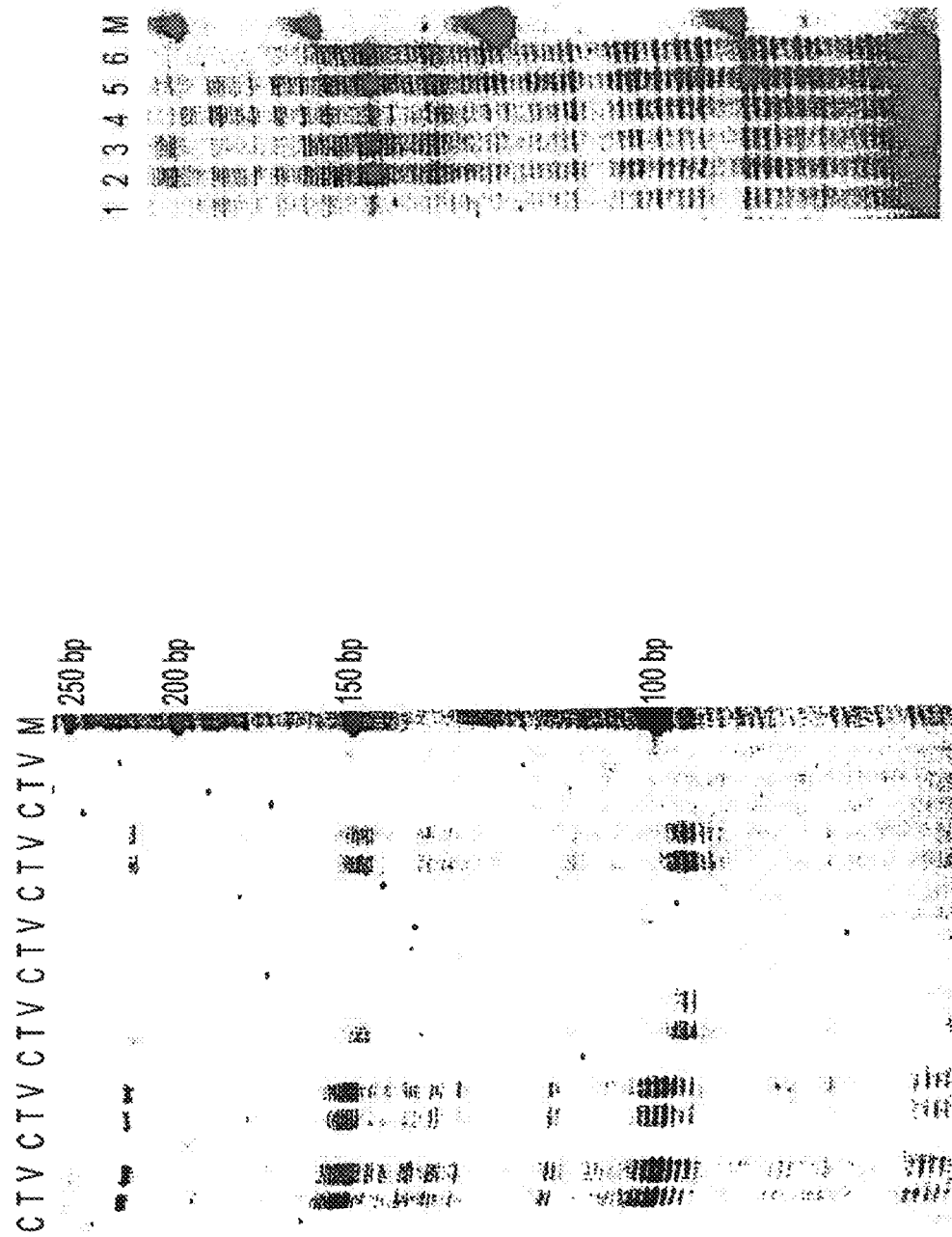

LM-PAP was performed as allele-specific PCR except for the direct labeling step by PAP (FIG. 16A). The purified PCR product was used for direct labeling with $^{32}$P labeled primers:

P3A:
5' TCTGACTGACCCCTATTCCCTGCTTA* 3'
(SEQ ID NO: 53; the 3' terminal deoxynucleotide
is A allele specific)
and P3G:
5' TCTGACTGACCCCTATTCCCTGCTTG* 3'
(SEQ ID NO: 54; the 3' terminal deoxynucleotide
is G allele specific)

using PAP reaction conditions in a 10 µl volume (50 mM KCl, 10 mM Tris/HCl (pH 7.6), 1.5 mM MgCl$_2$, 100 µM of each dNTP, 0.1 µM P*, 300 µM Na$_4$PP$_i$, 2% DMSO, 0.25 U each of AmpliTaqFS and AmpliTaq DNA Polymerases (Perkin-Elmer). The cycling conditions were 94° C., 10 sec.; 60° C., 1 min. and 72° C., 2 min. for a total of 8 or 16 cycles. LM-PAP was dramatically more specific than LM-PCR. The initial data with the dopamine D1 gene shows a lower background with LM-PAP than with the identical unblocked oligonucleotide with LM-PCR. Also, LM-PAP can be performed with the PGK gene, a gene with a very high GC rich region (70%) (FIG. 16B).

FIG. 16A shows a UV footprinting of the dopamine D1 receptor gene with a comparison of allele-specific LM-PAP and allele-specific LM-PCR. A direct comparison of LM-PAP with a P* and LM-PCR with an unblocked primer of identical sequence shows that two alleles can be distinguished with LM-PAP, but not with LM-PCR. Both methods were performed on HF-16 DNA that was untreated (C), in vitro treated (T) or in vivo treated (V) with UV. The direct labeling reaction using PAP conditions (lanes 7-18) with $^{32}$P labeled primers P3A* (lanes 7-9 and 13-15) and P3G* (lanes 10-12 and 16-18) was done with AmpliTaqFS and AmpliTaq for 8 and 16 cycles. For LM-PCR the direct labeling reaction was done with AmpliTaq (lanes 1-6) and $^{32}$P-labeled primers P3A (lanes 1-3) and P3G (lanes 4-6) for 8 cycles. Allelic primers P*s, P3A* and P3G* for LM-PAP clearly distinguish the two alleles, while unblocked allelic primers of identical sequence, P3A and P3G, were unable to distinguish the alleles by LM-PCR.

FIG. 16B shows a UV footprinting of the pgK gene. The LM-PAP procedure for PGK was essentially the same as for the dopamine D1 receptor except that Pfu Turbo DNA polymerase was used in the primer extension, as well as 7-deaza-dGTP/dGTP in a 3:1 ratio. Temperature cycles were 95° 1 min., 60° 2 min., and 76° 3 min. The PCR step was performed using Vent (exo-) DNA Polymerase at 97° 1 min., 60° 2 min., 76° 3 min. also with deaza dGTP. The purified PCR products were used for direct labeling with the $^{32}$P P3G* and P3C* primers using PAP reaction conditions in a 25 µl volume (50 mM KCL, 20 mM Hepes, pH 6.95, 10 mM (NH$_4$)$_2$SO$_4$, 1.5 mM MgCl$_2$, 40 µM dNTP, 150 µM Na$_4$PPi, 4% DMSO, and 1 unit of AmpliTaq FS DNA Polymerase. The conditions for cycling were 94° 15 sec., 60° 30 sec., and 72° 1 min. for 10 cycles.

Example 5

Optimization of PAP-A to Detect a Mutation in 1 of $10^4$-$10^5$ Templates

One µg of lambda phage DNA contains 2×$10^{10}$ copies of template. The specificity of PAP is determined by mixing one part mutant lacI templates with $10^4$ to $10^5$ parts control DNA templates, e.g., wild-type lacI. The specificity of PAP-A is a function of the error rate of the polymerase, the purity of P* (<2×$10^{-4}$ by current purification protocol) and the potential for damage of the DNA template in the extraction process. The yield and specificity of PAP is optimized by testing enzyme type and concentration and the concentrations of other components, such as dNTP, PP$_i$, Mg$^{++}$ or Mn$^{++}$. Hot-start PAP using antibody-activated enzyme, such as DNA polymerase, at room temperature can be used to eliminate spurious amplifications.

Wild-type and mutant lambda phage DNA, which are used in the laboratory as a model system to study spontaneous mutation in mammals, are prepared from infected E. coli SCS-8 cells (Nishino et al., 1996). The lambda phage is grown under high fidelity conditions and DNA is isolated with care under conditions with low rates of DNA damage (Stratagene manual) (Nishino et al., 1996; Hill et al., 1999).

The mutants include one example of each of the two types of transitions, the four types of transversions and a one-base nucleotide deletion. P*s specific for each of the mutations is synthesized. These DNA templates are used for reconstruction experiments in which mutated DNA is serially diluted into wild-type DNA. The spiked samples are used to optimize PAP-A. The most robust polymerases are chosen based on yield and specificity using TaqFS, ThermoSequenase, and SequiTherm Excel II (Epicentre). Other components of the reaction are optimized systematically, including thermocycling parameters, oligonucleotide length, and reagent concentrations of PP$_i$, dNTP and Mg$^{++}$ or Mn$^{++}$. Quantitative detection of the yield of PAP product is achieved with autoradiography or fluorescence on a SSCP gel. These data aids in the optimization of PAP-R and LM-PAP (below). The optimization of these various parameters result in a specificity of 1 part in $10^4$-$10^5$.

The optimized conditions are also tested for detecting mutations in the human factor IX gene by mixing human mutant genomic DNA templates with up to $10^4$ wild-type templates. As with the lambda experiment, exponential PAP is performed with appropriately designed oligonucleotides (using Oligo5 software) for 40 cycles and strong signal is achieved by autoradiography or by fluorescence detection.

Example 6

Optimization of PAP-R

In a model system, mismatches along the length of P* inhibited activation, even when the mismatch is two nucleotides from the 5' end (FIG. 14). An additional set of 18 mers of P*s, whose 5' termini were displaced 2, 6, 9, and 12 nucleotides downstream, also showed inhibition of activation (FIG. 13). In addition, 20 and 22 mers also show inhibition with single nucleotide mismatches (FIG. 12). To extend these findings and to lay the foundation for a robust method of resequencing, the relationship between the location of single base mismatches and activation of P*s is analyzed further.

The factor IX gene is used as a model system because more than 1,000 DNA samples from hemophilia patients and family members have been ascertained from previous work on the molecular epidemiology of germline mutations in humans (Sommer, 1995; Ketterling et al., 1999). Two 20-nucleotide regions of exon B and exon H in the human factor IX gene are used as model systems. The region of exon B is designed from nucleotides 6460 to 6479 (5' CGAGAAGTTTTTGAAAA-CAC 3' (SEQ ID NO:55; Yoshitake et al., 1985), within which eight different single base mutations are available. The region of exon H is from nucleotides 30845 to 30864 (5' GAACATA-CAGAGCAAAAGCG 3' (SEQ ID NO:56), within which seven mutations at different positions are available. P*s identical to wild-type regions B and H will be synthesized. Identical P*s are synthesized, with the exception of a single nucleotide mismatch.

The wild-type factor IX sequence is used in the initial studies. A few P*s that match the wild-type sequence or that mismatch at selected sites within the 5' third of the oligonucleotide sequence are helpful in performing pilot experiments to assess the optimal length of the oligonucleotide. The effects of polymerases and reaction conditions can be assessed.

From preliminary data, it appears that 18 mers or larger may be an optimal size. It is also possible that 25 mers or even 30 mers may be optimal. For the present example, it is assumed that 20 mers are an optimal size. Wild type P* and twenty P*s with one of the possible single base mismatches at each nucleotide of the position region of exon B are synthesized. Eight of these P* are a perfect match to a mutation in a patient with hemophilia B. As positive controls, it is shown that these P*s activate efficiently when the appropriate mutated DNA sample is used. Exponential PAP and linear PAP are performed and the noise rate is determined. The noise rate for linear PAP is generally lower and is used.

To confirm preliminary data in another sequence context, a similar experiment is performed in exon H. The seven mutations in that region of exon H are analyzed in a blinded manner to determine if the precise match is detected. The effects of the position of the mismatch or the type of mismatch on P* activation is determined. The effects of different polymerases, reaction temperature, and other reaction conditions can also be determined. Another set of 20 P*s provides additional data from mismatches 12-20 nucleotides from the 3' terminus.

Example 7

Optimization of LM-PAP

The human dopamine $D_1$ receptor gene and the mouse Pgk1 gene are used as model systems to compare the analysis of chromatin structure when LM-PAP or LM-PCR is utilized. The dopamine $D_1$ receptor gene has been described above. X chromosome inactivation occurs at an early embryonic stage. Since the two alleles in female cells maintain a different expression status, this is an advantageous system for studies of gene regulation. Pgk1 is an X-linked housekeeping gene encoding phosphoglycerate kinase (PGK). PGK is an important enzyme in glycolysis and the gene is expected to be active all the time except in the inactive X chromosome (Xi) of female somatic cells and in male germ cells.

The preliminary data shows a dramatic enhancement of specificity with LM-PAP relative to LM-PCR in the dopamine $D_1$ receptor gene, a gene not previously analyzed for chromatin structure (FIG. 16A). In this example, LM-PAP and LM-PCR are performed. Three sets of oligonucleotides that generated LM-PCR profiles and seven sets of primers that generated LM-PCR profiles with unacceptable background in the Pgk1 (and other X-chromosomal genes) are used to compare LM-PAP with LM-PCR. Deoxy-terminating and dideoxy-terminating oligonucleotides of identical sequence are utilized to perform LM-PAP and LM-PCR, respectively. The level of signal relative to background is also quantitated by a PhosphoImager. The average signal-to-noise ratio is determined. Optimization data derived from analyses with PAP-A and PAP-R are also useful in the LM-PAP protocol. LM-PAP is optimized for the two regions to determine if the signal-to-noise ratio can be reduced further.

Example 8

Optimization of Allele-Specific LM-PAP

Polymorphic sites of pgk1a and 1b gene in both coding and non-coding regions have been reported (Boer et al., 1990). These are used to design the allele-specific P*. One allele-specific oligonucleotide is chosen prospectively from the Pgk1 gene and one is chosen prospectively from the dopamine $D_1$ receptor gene. Blocked and unblocked oligonucleotides of identical sequence are synthesized and allele-specific LM-PAP and LM-PCR are performed, respectively. The signal to noise ratio is quantitated and compared.

Example 9

PAP-R on a Microarray

The initial experiment will focus on the two 20 nucleotide regions of exons B and H as described above. The experimental design of PAP-R is similar to the experiments described above, except for digital light-direct synthesis of P* oligonucleotides on a microarray, e.g., with the Geniom® instrument. A total of 160 oligonucleotides are synthesized complementary to wild-type and to all the single base mismatches for 20 bp regions of exons B and H of the factor IX gene. As a positive control, 160 oligonucleotides, each out of registered by one nucleotide, are synthesized to match exactly an adjacent 160 bp region of the factor IX gene. Genomic DNA from wild-type and mutant samples is amplified, annealed to the oligonucleotides and primer extension will be performed with a fluorescent dideoxy terminator. The protocol is optimized for the solid support. Adjustment of primer length, enzyme utilized and reaction conditions is performed such that most, if not all, of the oligonucleotides that mismatch the two 20 bp nucleotide regions of factor IX generate little if any signal, while most of the 160 control oligonucleotides generate a strong signal.

One strategy for resequencing is shown in FIGS. 3 and 4. Each nucleotide in the complementary strand of the predetermined sequence is queried by four downstream P*s, such as 20 mers, which have identical sequence except for the 3' terminus, which is either ddA, ddT, ddG or ddC. For a 1 kb segment, 4,000 P*s are needed in the downstream direction. In the second set of experiments, exons B and H of the factor IX gene are resequenced. Samples from more than 200 patients with different mutations in these regions are available for analysis. False positives and false negatives are assessed by blinded analysis. Heterozygous female samples are available for many of the mutations. For the remaining male patient samples one to one mixing experiments with wild-type or a second mutated sample generates the equivalent of heterozygotes or compound heterozygotes, respectively. Subsequently, all the regions of likely functional significance (the putative promoter region, the coding regions, and the splice junctions) are resequenced (2.2 kb). Since more than 600 independent mutations are available, it is possible to determine whether more than 99% of all sequence changes are identified (the sequence changes in these samples have been determined by direct sequencing over the course of a decade).

A P* with a single base substitution at the 3' terminus generates a signal at the position of hemizygous or homozygous point mutations. The mutation also creates a "gap" of no PAP signal, which spans a region of several successive nucleotides. When a single base substitution occurs, the gap size (nucleotides)+1=the length of the 3' specific subsequence (FIGS. 3 and 4).

To analyze samples with higher G+C content (55%), mutations in the lacI gene are utilized. These mutations from the Big Blue® Transgenic Mouse Mutation Detection System, have the potential to facilitate the definition of a strategy that detects more than 99.9% of mutations, since more than 6,000 mutations are available in this system. The relevant regions are analyzed with the help of robotic devices. In addition, hundreds of mutations or polymorphisms are available for analysis in other genes with G+C contents of 30-75%. The dystrophin gene is particularly amenable to testing performance under conditions in which megabases of sequence require scanning. In this gene in which 90 segments are amplified by a robotic device, virtually all sequence variants have been defined by DOVAM-S followed by DNA sequencing. This is advantageous because many molecular epidemiological and molecular diagnostic applications benefit from resequencing that detects virtually 100% of the mutations.

Example 10

PAP Amplification Directly from Human and Mouse Genomic DNAs

PAP was performed with each of two P*s, P1* (SEQ ID NO:45, G allele specific) or P2* (SEQ ID NO:47, A allele specific) and an upstream unblocked primer (U; (SEQ ID NO:48)) to amplify 180-bp segments of the $D_1$ dopamine gene. The P* are 26-mers with ddC and ddG at the 3' termini. 100 ng of human genomic DNA was amplified for 35 cycles followed by 2% gel electrophoresis. The PAP reaction mixture contained a total volume of 25 µl: 50 mM KCl, 20 mM HEPES/NaOH (pH 6.9 at 25° C.), 10 mM $(NH_4)_2SO_4$, 1.5 mM $MgCl_2$, 40 µM each of the four dNTPs (dATP, dTTP, dGTP, dCTP), 0.1 µM U, 150 µM $Na_4PP_i$, 2% DMSO, 0.5 U of AmpliTaqFS polymerase (PE Applied Biosystems), 0.5 U Taq polymerase and 100 ng of human genomic DNA. The cycling conditions were 94° C. for 15 sec, 65° C. for 30 sec and 72° C. for 1 min. FIG. 17A shows the results for PAP amplification of the $D_1$ dopamine gene. In lanes 2 and 5, P1* is specific for the A allele template at 24 nucleotides from the 3' terminus, so there is little or no discrimination between the G/G and A/A genotypes. In lanes 3 and 6, P2* is specific for the A allele template at 2 nucleotides from the 3' terminus, so there is specific amplification of the A/A genotype. Lanes 1 and 5 are PCR controls. Lanes 4 and 8 are negative controls without P*. Lane M is 120 ng cpx DNA/HAEIV marker.

Three Bi-PAP assays were tested directly from mouse genomic DNA. Bi-PAP was performed with two P*s containing a dideoxynucleotide blocker at the 3' terminus to amplify an 80-bp segment of the lacI gene. The P*s are specific to the wild-type template and are 40-42 nucleotides long. In each of the three Bi-PAP assays, two opposite P* with one nucleotide overlap at their 3' termini were used to amplify 400 copies of the lacI gene using 35 cycles. The sequences of the P*s are as follows:

```
                                          (SEQ ID NO: 67)
5' GAAGCGGCGTCGAAGCCTGTAAAGCGGCGGTGCACAATCT* 3'
and (SEQ ID NO: 68)
5' GCGGATAGTTAATGATCAGCCCACTGACGCGTTGCGCGAGAA* 3'
in lanes 1 and 2;

(SEQ ID NO: 69)
5' GATGGCGGAGCTGAATTACATTCCCAACCGCGTGGCACAA* 3'
and (SEQ ID NO: 70)
5' GGCAACGCCAATCAGCAACGACTGTTTGCCCGCCAGTTGT* 3'
in lanes 3 and 4;
and (SEQ ID NO: 71)
5' TACATTCCCAACCGCGTGGCACAACAACTGGCGGGCAAAC* 3'
and (SEQ ID NO: 72)
5' GGGCCAGACTGGAGGTGGCAACGCCAATCAGCAACGACTG* 3'
in lanes 5 and 6.
```

The PAP reaction mixture contained a total volume of 25 µl: 50 mM KCl, 20 mM HEPES/NaOH (pH 6.9 at 25° C.), 10 mM $(NH_4)_2SO_4$, 1.5 mM $MgCl_2$, 40 µM each of the four dNTPs (dATP, dTTP, dGTP, dCTP), 0.1 µM U, 150 µM $Na_4PP_i$, 4% DMSO, 1.0 U of AmpliTaqFS polymerase (PE Applied Biosystems) and 400 copies of mouse genomic DNA. The cycling conditions were 94° C. for 15 sec, 65° C. for 30 sec and 72° C. for 1 min. The unincorporated P*s were separated well from the Bi-PAP product on 2% agarose gel. No dimer was seen. FIG. 17B shows the results for these Bi-PAP assays. In lanes 1, 3 and 5, the wild-type templates are amplified. Lanes 2, 4 and 6 are negative controls without mouse genomic DNA.

Three PAP assays directly amplified 180-bp segments of the D1 receptor gene from human genomic DNA with strong signals of PAP products. The allele-specificity of 26-mer P* remains when the mismatch is at 2 nucleotides from the 3' terminus, but the allele-specificity is lost when the mismatch is at 24 nucleotides from the 3' terminus. Three Bi-PAP assays directly amplified as low as four hundred copies of the lacI gene from mouse genomic DNA. The P* oligonucleotides have different deoxynucleotides blocked at the 3' terminus and all can be efficiently activated. Addition of extra human DNA did not affect the amplification of the lacI gene in mouse genomic DNA. The product of Bi-PAP was easily distinguished from unincorporated P*s. P* does not form dimmers because P* needs long and perfectly matched regions at the 3' terminus for activation.

Example 11

PAP with Acyclonucleotides and Various Polymerases

λ Phage DNA Template

The wild-type λ phage DNA template that contains an inserted wild-type lacI gene of E. coli (Kohler et al., 1991) was purchased from Stratagene. The mutant λ phage DNA template was prepared from λ phage plaques transformed into SCS-8 E. coli cells according to Maniatis, et al. (1982). It contained a T to G mutation at nucleotide 369 in the lacI gene. The amount of λ phage DNA was determined by UV absorbance at 260 nm.

Synthesis of P* by Adding Acyclonucleotide or a Dideoxynucleotide at the 3' Terminus The 3' terminal acyclonucleotide or 3' terminal dideoxynucleotide was added to a deoxynucleotide oligonucleotide by terminal transferase. The mixture contained a total volume of 25 μl: 100 mM potassium cacodylate (pH 7.2), 2.0 mM $CoCl_2$, 0.2 mM DTT, 2 nM of the oligonucleotide, 2.4 mM acycloNTP (the molar ratio of the 3'-OH terminus to acycloNTP was 1:30) (New England BioLabs), or 2.4 mM 2',3'-ddNTP (the molar ratio of the 3'-OH terminus to ddNTP was 1:30) (Roche), 100 U of terminal transferase (Invitrogen). The reaction was incubated at 37° C. for 6 hr and then stopped by adding EDTA to a 5 mM final concentration. After desalting using a Centri-spin$^{-20}$ column (Princeton Separations), P* was purified by preparative 7 M urea/18% polyacrylamide gel electrophoresis with 30 mM triethanolamine/tricine buffer (pH 7.9 at 25° C.) (Maniatis, et al., 1982; Liu, et al., 1999b). The amount of recovered P* was determined by UV absorbance at 260 nm.

Since small amounts of unterminated oligonucleotide would result in unexpected PCR amplification, the purity of P* was tested by the absence of PCR product at pH 8.3 in which pyrophosphorolysis is inhibited. It is estimated that more than 99.99% of P* contained an acyclonucleotide or a dideoxynucleotide at the 3' terminus.

PAP Amplification

Figure 18A:
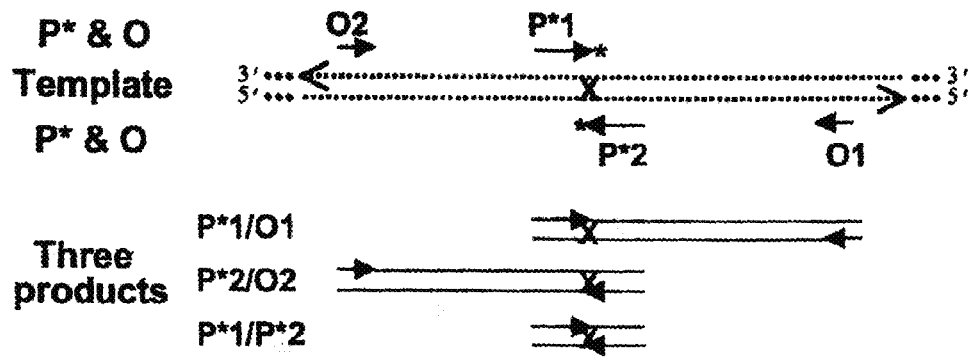
FIGS. 18A-18E show PAP amplification using 3' terminal acyclonucleotide blocked P*.

PAP was examined with P*1 and O1, with P*2 and O2, and with P*1 and P*2 respectively (FIG. 18A and Table 6). The P*s were 30 or 35 nucleotide long and contained an acyclonucleotide or a dideoxynucleotide at the 3' terminus.

The PAP reaction mixture with AmpliTaqFS DNA polymerase contained a total volume of 25 μl: 50 mM KCl, 20 mM HEPES/NaOH (pH 6.9 at 25° C.), 10 mM $(NH_4)_2SO_4$, 1.5 mM $MgCl_2$, 50 μM each of the four dNTPs (dATP, dTTP, dGTP and dCTP), 0.1 μM of each oligonucleotide, 150 μM $Na_4PP_i$, 4% DMSO, 1 U of AmpliTaqFS DNA polymerase (PE Applied Biosystems), 0.1 ng of the λ phage DNA template. The cycling conditions were 92° C. for 10 sec, 65° C. for 30 sec, and 72° C. for 1 min for a total of 30 cycles. A denaturing step of 92° C. for 1 min was added before the first cycle.

The PAP reaction mixture with Vent (exo-) or Pfu (exo-) contained a total volume of 10 mM KCl, 20 mM HEPES/NaOH (pH 7.19 at 25° C.), 10 mM $(NH_4)_2SO_3$, 1.2 mM $MgCl_2$, 50 μM each of the four dNTPs (dATP, dTTP, dGTP and dCTP), 0.1 μM of each oligonucleotide, 150 μM $Na_4PP_i$, 4% DMSO, 1 U of Vent (exo-) DNA polymerase (New England BioLabs) or Pfu (exo-) DNA polymerase (Stratagene), 0.1 ng of the λ phage DNA template. The cycling conditions were 94° C. for 15 sec, 60° C. for 30 sec, and 72° C. for 1 min for a total of 30 cycles. A denaturing step of 94° C. for 1 min was added before the first cycle.

The product was electrophoresed through a standard 2% agarose gel. The gel was stained with ethidium bromide for UV photography by a CCD camera (Bio-Rad Gel Doc 1000).

As shown above, TaqFS, a genetically engineered DNA polymerase (Innis and Gelfand, 1999), greatly improved the efficiency of PAP. 3' terminal dideoxynucleotide blocked P*s can be activated by pyrophosphorolysis to remove the 3' terminal dideoxynucleotide in the presence of pyrophosphate ($PP_i$) and the complementary strand of the allelic template. Then the activated P* can be extended by DNA polymerization.

PAP was performed with 3' acyclonucleotide blocked P*s by using λ phage DNA containing the lacI gene as model system. P*1 and P*2 are downstream and upstream blocked oligonucleotides, respectively, for the same mutation (FIG. 18A and Table 6). The P*1 and P*2 have an acycloGMP and acycloCMP at their 3' termini, respectively. Amplification products were absent without pyrophosphate added at pH 8.3 where pyrophosphorolysis is inhibited, showing that P*1 and P*2 were not directly extendible.

Figure 18B:
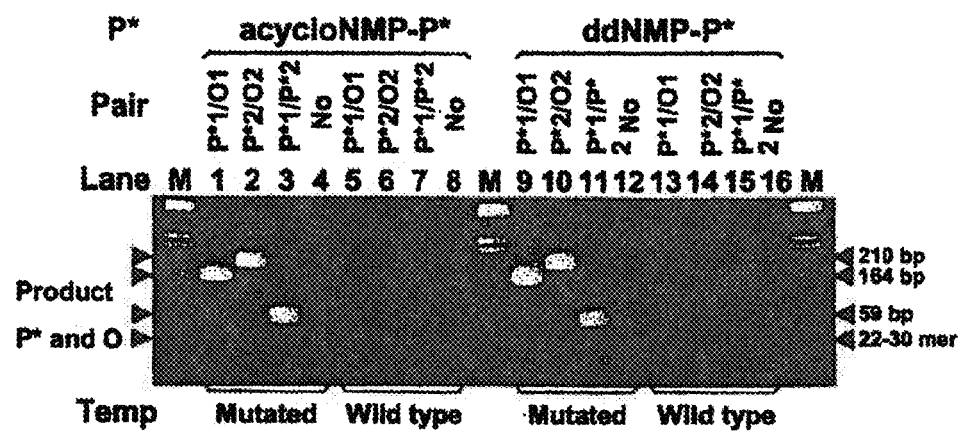

P*1 and P*2 are specific to the mutated template but mismatch to the wild-type template at their 3' termini. The mutated template was amplified efficiently by PAP with one acyclonucleotide blocked P* and one opposing unblocked oligonucleotide and by PAP with two opposing 3' terminal acyclonucleotide blocked P*s (lanes 1 and 2 in FIG. 18B), with two opposing acyclonucleotide blocked P*s (a special form of PAP where the two opposing P*s are overlapped at their 3' termini by one nucleotide) (lane 3 in FIG. 18B). However, no product was generated from the wild-type template because of the mismatch at the 3' terminus, showing the specificity (lanes 5-7 in FIG. 18B). PAP with the 3' dideoxynucleotide blocked P* showed similar results (lanes 9-16 in FIG. 18B). Direct sequencing analysis confirmed the correct sequence of the amplified product. The effect of P* length was also tested. Similar results were obtained with 35-mer

TABLE 6

List of Oligonucleotides

| Desig. | Name[a] | Sequence (ID NO:) | 3' Terminal | PAP Amplification (allele) G:C | T:A |
|---|---|---|---|---|---|
| P*1 | P*(340)30D | CGAAGCCTGTAAAGCGGCGGTGCACAATCG* (57) | acycloGMP or ddGMP | Yes | No |
| O1 | O(502)25U | ACTGTTGATGGGTGTCTGGTCAGAG (58) | dGMP | | |
| P*2 | P*(398)30U | TGATCAGCCCACTGACGCGTTGCGCGAGAC* (59) | acycloCMP or ddCMP | Yes | No |
| O2 | O(190)21D | ACAACTGGCGGGCAAACAGTC (60) | dCMP | | |

[a]The position of the first nucleotide of the transcript in the lacI gene of E. coli is assigned the nucleotide position 1 (Farabaugh, 1978). As an example for P*1, P* = pyrophosphorolysis activatable oligonucleotide, it may be a 3' terminal acyclonucleotide blocked P* or a 3' terminal dideoxynucleotide blocked P*. (340)30D = 5'end of the P* begins at 340, the length is 30 nucleotides and the direction is downstream (i.e., in the direction of transcription). The precise sizes and Locations of the amplified fragment can be obtained from the informative names. The 30-mer P*s are indicated above. The 35-mer P*s are 3' co-terminal with the 30-mer P*s and 5 nucleotides longer at their 5' termini.

Figure 18C:
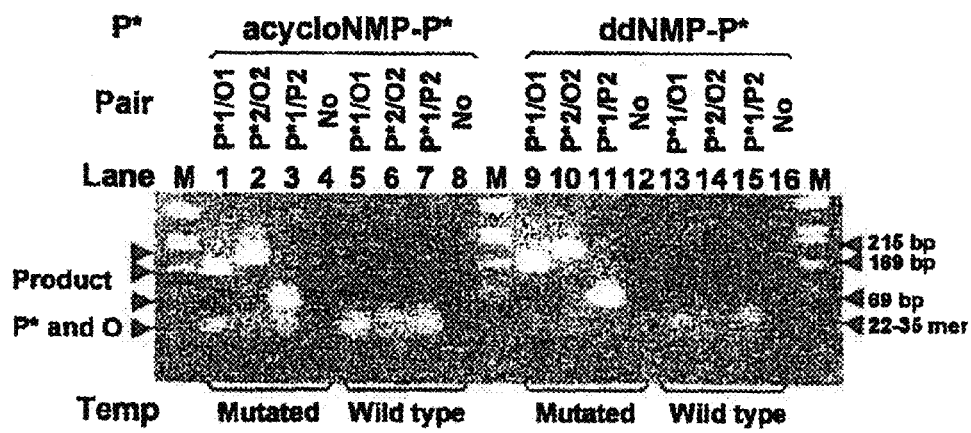

P*s that are co-terminal with the 30-mer P*s and five nucleotides longer at their 5' termini (FIG. 18C). Other P*s specific for the wild-type sequence at the 3' terminus (with acycloTMP and ddTMP) were also tested with similar results.

Figure 18D:
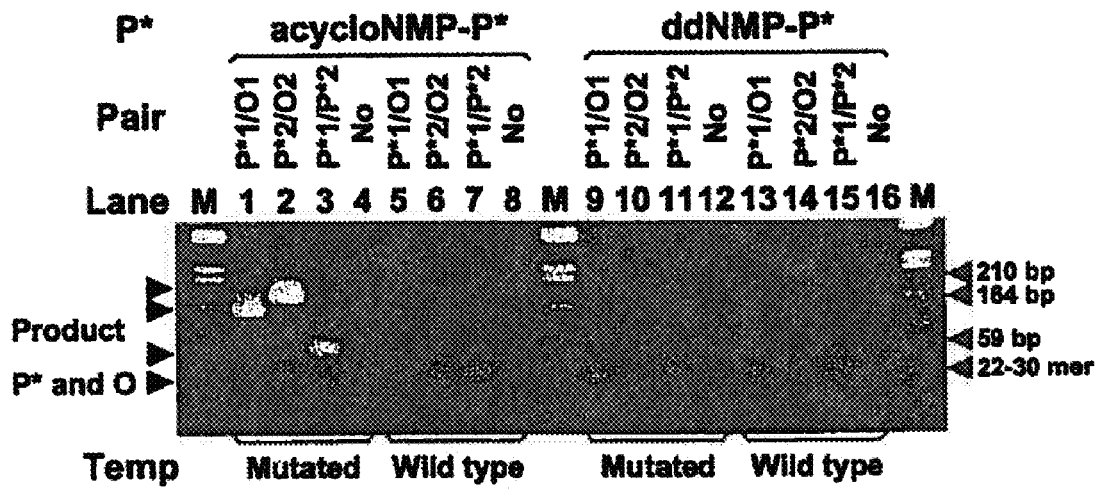
Figure 18E:
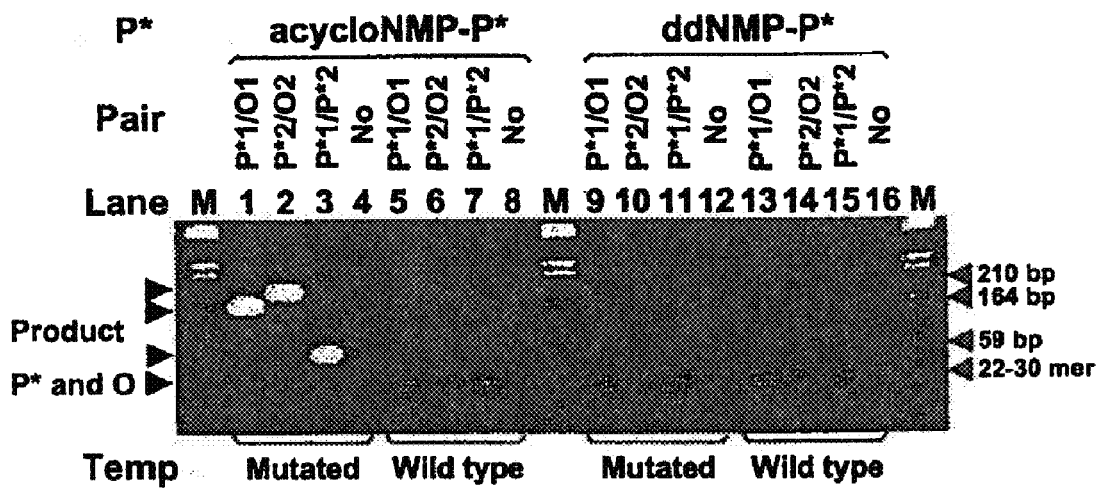

Family II DNA polymerases Vent (exo-) and Pfu (exo-) were tested using the above model system. With the acyclonucleotide blocker and perfect match at the 3' terminus, the mutated template was amplified efficiently by PAP with one P* (lanes 1 and 2 in FIGS. 18D and 18E) and one opposing unblocked oligonucleotide and by PAP with two opposing P*s of P*1 and P*2 (a special form of PAP where the two opposing P*s are overlapped at their 3' termini by one nucleotide) (lane 3 in FIGS. 18D and 18E). However, no product was generated from the wild-type template because P*1 and P*2 mismatch the wild-type template at their 3' termini, showing the specificity (lanes 5-7 in FIGS. 18D and 18E). Vent (exo-) and Pfu (exo-) polymerases could not amplify with the 3' dideoxynucleotide blocked P* (lanes 9-16 in FIGS. 18D and 18E). Direct sequencing analysis confirmed the correct sequence of the P* 1/O1 and P*2/O 2 products. Similar results were obtained with AcycloPol (Perkin-Elmer), a genetically engineered Family II archeon DNA polymerase. It is not clear why PAP with Vent (exo-) and Pfu (exo-) DNA polymerases discriminates against 3' dideoxyribonucleotide blockers.

Other Blockers

These results demonstrate that two terminators used in Sanger sequencing can be used as blockers in PAP. Terminators have also been described as therapies of viral illnesses, such as AIDS, and for cancer therapy, such as, 3'-deoxyadenosine (cordycepin), 3'-azido-3'-deoxythymidine (AZT), 2',3'-dideoxyinosine (ddI), 2',3'-dideoxy-3'-thiacytidine (3TC) and 2',3'-didehydro-2',3'-dideoxythymidine (d4T). DNA polymerase can incorporate their triphosphate form into the synthesizing strand, and the incorporation cause termination of the extension (Gardner and Jack, 1999; Cheng et al., 1987; St. Clair et al., 1987; Ueno and Mitsuya, 1997). The monophosphate nucleotides of 3'-azido-3'-deoxythymidine (AZT), 2',3'-dideoxy-3'-thiacytidine (3TC) and 2',3'-didehydro-2',3'-dideoxythymidine (d4T), when located at the 3' termini of oligonucleotides, can be removed by pyrophosphorolysis by HIV reverse transcriptase or its variants (Anion et al., 1998; Gotte et al., 2000; Meyer et al., 2000; Urban et al., 2001). These results indicate the application of PAP for various types of blockers and for RNA templates.

In summary, PAP amplification occurred efficiently and specifically with 3' acyclonucleotide and 3' dideoxynucleotide blockers using TaqFS DNA polymerase, and only with acyclonucleotide blockers using Vent (exo-) and Pfu (exo-) DNA polymerases. Other 3' terminal nonextendible oligonucleotides and other DNA polymerases can be used, if the 3' terminal nucleotide can be removed by pyrophosphorolysis, and the activated oligonucleotide can be extended.

Example 12

Detection of Extremely Rare Alleles by Bi-PAP

λ Phage DNA Template

The wild-type λ phage DNA template that contains an inserted wild-type lacI gene of *E. coli* (Kohler et al., 1991) was purchased from Stratagene. Three mutated λ phage DNA templates were prepared from λ phage plaques transformed into SCS-8 *E. coli* cells according to Maniatis et al (1982). They contain an A to T mutation at nucleotide position 190, a T to G mutation at nucleotide 369 and a T to C mutation at nucleotide 369 in the lacI gene, respectively. The amount of λ phage DNA was determined by UV absorbance at 260 nm.

Synthesis of P* by Adding a 3' Dideoxynucleotide

The 3' terminal dideoxynucleotide was added to an oligodeoxynucleotide by terminal transferase. The mixture contained a total volume of 25 µl: 100 mM potassium cacodylate (pH 7.2), 2.0 mM $CoCl_2$, 0.2 mM DTT, 2 nM of the oligonucleotide, 2.4 mM 2',3'-ddNTP (the molar ratio of the 3'-OH terminus to ddNTP was 1:30) (Roche), 100 U of terminal transferase (Invitrogen). The reaction was incubated at 37° C. for 6 hr and then stopped by adding EDTA to a 5 mM final concentration. After desalting using a Centri-spin$^{-20}$ column (Princeton Separations), P* was purified by preparative 7 M urea/16% polyacrylamide gel electrophoresis with 30 mM Triethanolamine/Tricine buffer (pH 7.9 at 25° C.) (Maniatis et al., 1982, Liu et al., 1999b). The amount of recovered P* was determined by UV absorbance at 260 nm.

Since small amounts of unterminated oligonucleotide would result in unexpected PCR amplification, P* was $^{32}$P-labeled at the 5' terminus by T4 polynucleotide kinase and then was electrophoresed through a 7 M urea/20% polyacrylamide gel. Only P* products were visible even when the gel was overexposed. It is estimated that more than 99.99% of P* contained a dideoxynucleotide at the 3' terminus. The purity of P* was supported by the absence of PCR product at pH 8.3 in which pyrophosphorolysis is inhibited.

PAP Amplification

Bi-PAP assays for nucleotide 190 and nucleotide 369 of the lacI gene were examined. The P*s were 40 nucleotides long except that the upstream P*s for position 369 are 42 nucleotides. Each P* contained the sequence-specific nucleotide at the 3' terminus. The PAP reaction mixture contained a total volume of 25 µl: 50 mM KCl, 20 mM HEPES/NaOH (pH 6.9 at 25° C.), 10 mM $(NH_4)_2SO_4$, 1.5 mM $MgCl_2$, 40 µM each of the four dNTPs (dATP, dTTP, dGTP and dCTP), 0.1 µM each P*, 150 µM $Na_4PP_i$, 4% DMSO, 1 µCi of [α-$^{32}$P]-dCTP (3000 Ci/mmole, Amersham), 1 U of AmpliTaqFS DNA polymerase (PE Applied Biosystems), 2,000 copies of the λ phage DNA template or stated elsewhere. The cycling conditions were 92° C. for 6 sec, 68° C. for 20 sec, and 72° C. for 20 sec for a total of 35 cycles. A denaturing step of 92° C. for 1 min was added before the first cycle.

The product was electrophoresed through a standard 2.5% agarose gel, and the gel was stained with ethidium bromide for UV photography by a CCD camera (Bio-Rad Gel Doc 1000).

In order to differentiate the mutated product from the wild-type product of the same size, non-denaturing SSCP gel electrophoresis was performed (Orita et al., 1989). The reaction was mixed with two-fold volume of loading buffer (7M urea and 50% formamide), boiled and rapidly cooled on ice. The product in 10 µl of the mixed reaction was electrophoresed through an 8% non-denaturing PAGE-PLUS (Amresco) gel with 30 mM Ethanolamine/Capsco buffer (pH 9.6) (Liu et al., 1999b) at 4° C. The gel was dried and exposed to Kodak X-OMAT™ AR film for autoradiography. Three or four bands from each amplified product were seen on a gel. The upper one or two bands were double strained DNA due to hybridization of de-natured single-stranded segments during the electrophoresis as a result of the substantial amounts of amplified product present. Increasing the concentration of the amplified product further increase the intensity of the upper bands.

Highly Efficient PAP Amplification

TaqFS, a genetically engineered DNA polymerase greatly improved the efficiency of PAP. The conditions of PAP were further optimized for dramatically higher efficiencies allowing PAP to amplify directly from a few copies of λ phage DNA or human genomic DNA template. The reaction components and the thermocycling regime were optimized, including: i) decreased concentrations of PPi in that keeping the PPi to dNTP ratio essentially constant, ii) use of low pH HEPES buffer (pH 6.9 at 25° C.), iii) addition of $(NH_4)_2SO_3$, iv) increased amount of TaqFS, and v) higher annealing temperature.

Bi-PAP

Figure 19:
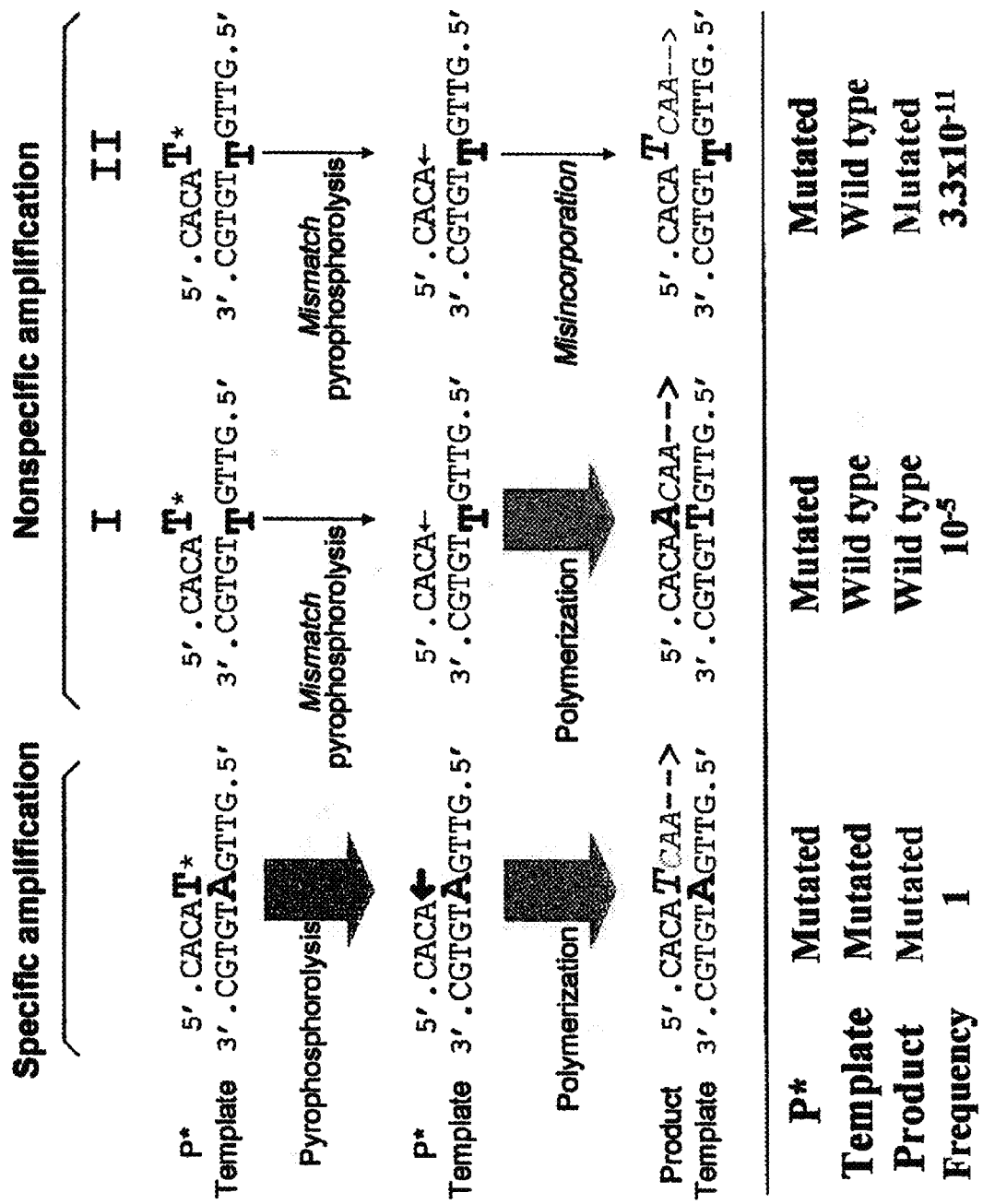
FIG. 19 shows that PAP has high selectivity to detect rare mutations in the abundance of the wild-type template. In the example of nucleotide position 190, the mutation-specific P* matches the mutated A template but mismatches the wild-type T template at the 3' terminus. Specific and efficient amplification is indicated by thick arrows. When hybridized to the mutated A template, the P* cannot extend directly from the 3' terminal dideoxynucleotide, the 3' terminal ddTMP must be removed by pyrophosphorolysis and the activated oligonucleotide is then extended efficiently. Two types of nonspecific amplification from the T template are indicated as Types I and II. The nonspecific amplification occurs rarely when mismatch pyrophosphorolysis occurs to generate a wild-type product that will not support efficient amplification as template for subsequent cycles (Type I) (the error is indicated by thin arrow and estimated frequency of as low as $10^{-5}$). When both mismatch pyrophosphorolysis and misincorporation occur extremely rarely to generate a mutated product (Type II) (the errors are indicated by thin arrows and estimated coupled frequency of $3.3\times10^{-11}$). Once the errors occur, the mutated product can be amplified exponentially in subsequent cycles and so it determines the selectivity.

PAP has a potential selectivity of $3.3 \times 10^{11}:1$ (FIG. 19). Approaching this potential requires a design that eliminates confounding sources of error. The A190T mutation of the lacI gene of λ DNA is used as a model system. In PAP with one downstream P* and one upstream unblocked oligonucleotide, extension errors from the non-blocked upstream oligonucleotide can produce the rare mutation of interest, thus reducing the selectivity. If the misincorporation rate of TaqFS is $10^{-4}$ per incorporated nucleotide and one of the three possible misincorporations generates the A→T mutation on the newly synthesized upstream strand, the selectivity decreases to $3.3 \times 10^{-5}$ due to the side effect. In order to remove this limitation, Bi-PAP was developed (FIG. 20A). In Bi-PAP, both the downstream and upstream oligonucleotides are P*s that are specific for the nucleotide of interest at their 3' termini. The P*s overlap at their 3' termini by one nucleotide.

Figure 20B:
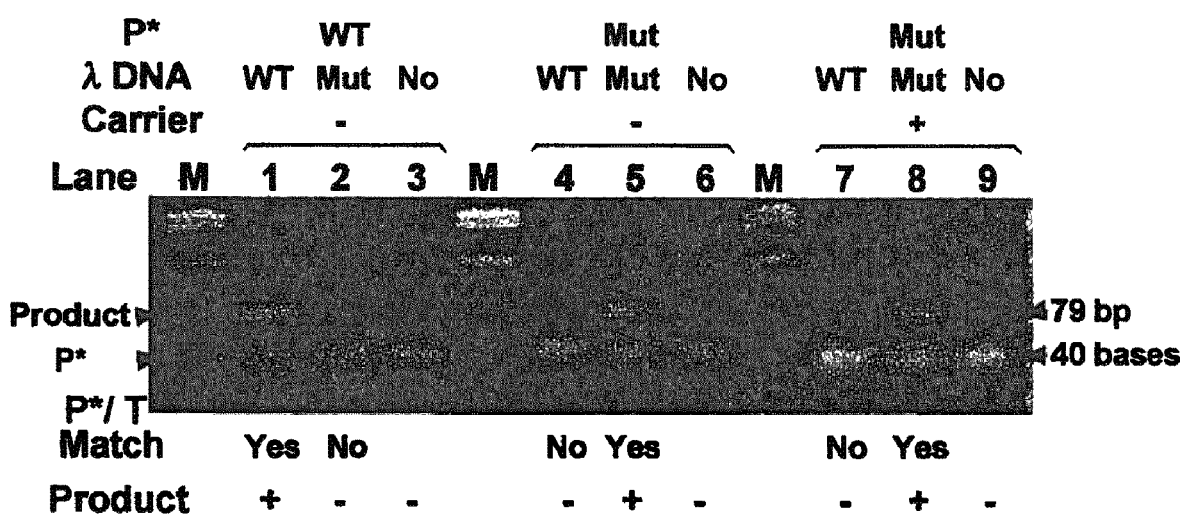

Bi-PAP amplified efficiently and specifically at nucleotide position 190 using λ phage DNA containing the lacI gene as template (FIG. 20B). Addition of human genomic DNA did not affect the amplification. The 79-bp product of Bi-PAP was easily distinguished from unincorporated P*s. P* did not form dimers because P* needs a perfectly matched region at the 3' terminus for activation. Similar results were observed at nucleotide position 369. Direct sequencing analysis confirmed the correct sequence of the amplified product.

Sensitivity and Selectivity of Bi-PAP

In order to demonstrate the extremely high selectivity of Bi-PAP, more than $10^{10}$ copies of DNA template was used for a Bi-PAP reaction. λ DNA containing the lacI gene of E. coli was chosen as the model system because 1 μg of λ DNA contains $2 \times 10^{10}$ vector genomes, while 1 μg of human genomic DNA only contains $3.3 \times 10^5$ genomes. In order to avoid potential contamination of the wild-type λ DNA in this laboratory, mutation-specific Bi-PAP assays with mutated P*s were chosen to amplify the wild-type λ DNA. The relative frequency of a spontaneous mutation of the lacI gene in the wild-type λ DNA is estimated to be less than $10^{-9}$ by examining λ phage plaques infecting E. coli.

Figure 21A:
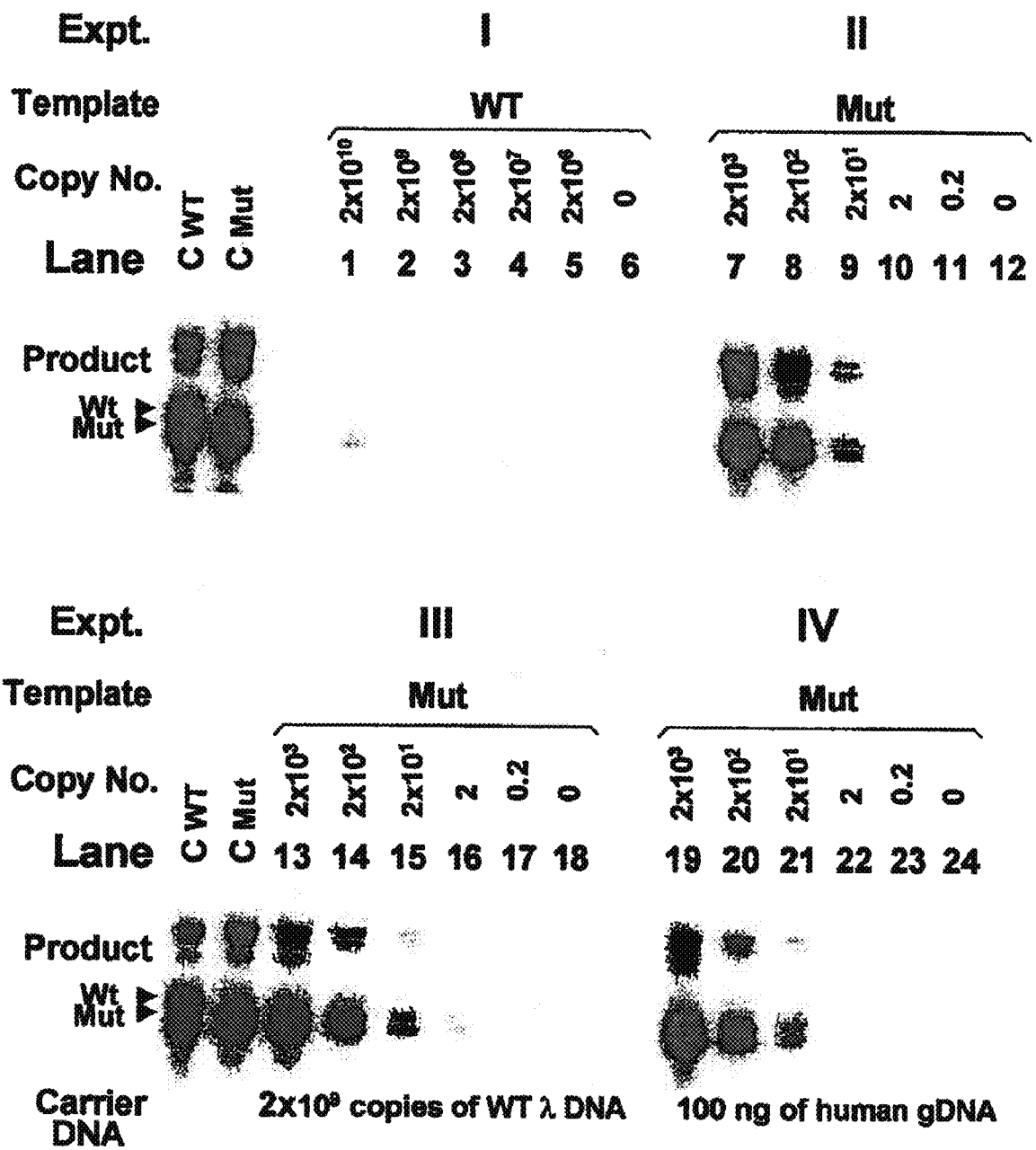
FIGS. 21A-21C show titration of template for sensitivity and selectivity of Bi-PAP. With the mutated P*s, the wild-type template was amplified to generate the mutated product in Experiment I. The mutated template was amplified to generate the mutated product in Experiments II, III and IV.
Figure 21B:
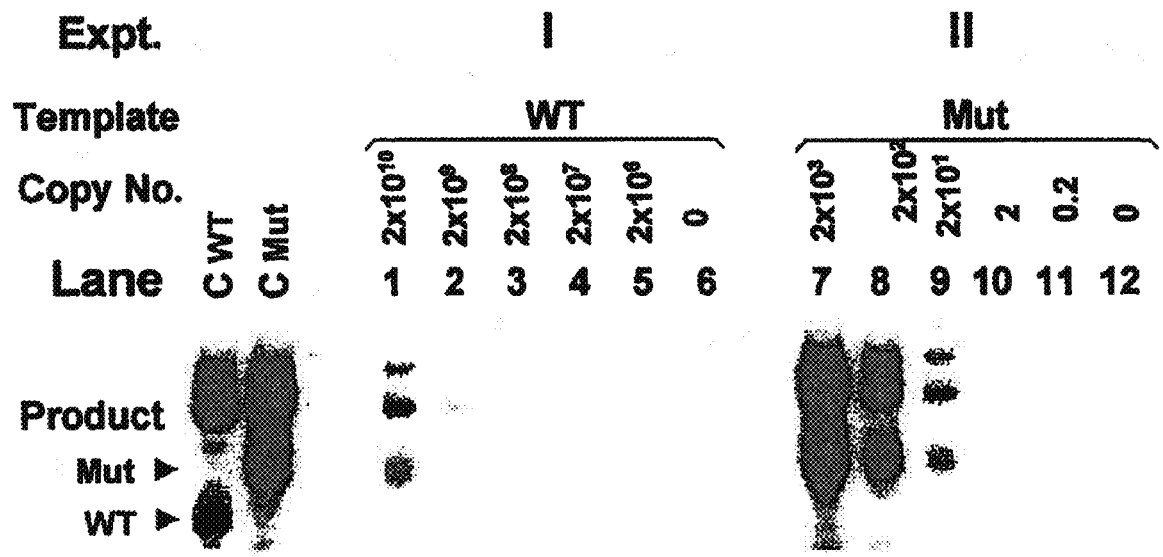
Figure 21C:
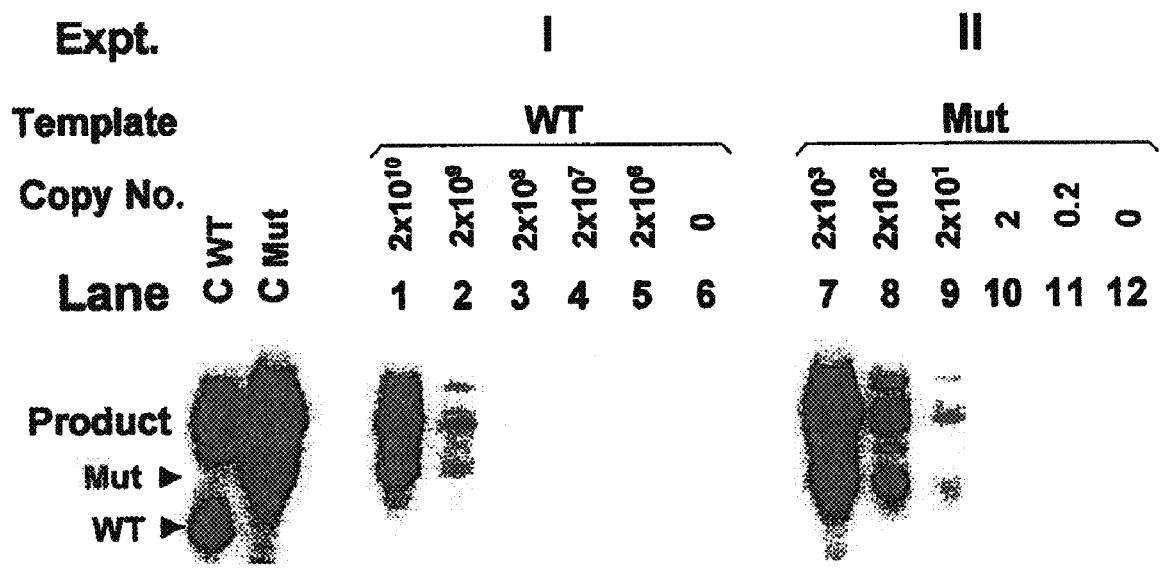
Figure 22:
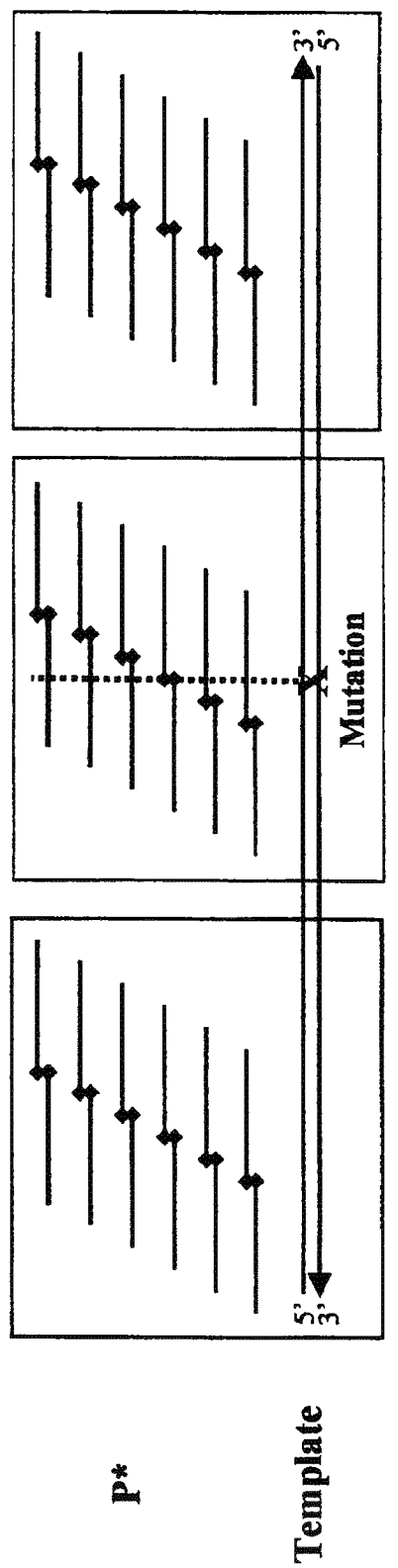
FIG. 22 shows a design of P* microarray for Bi-PAP resequencing. Bi-PAP can be used for resequencing to detect unknown mutations in a known region on a microarray. The P*s are designed according to the wild-type template. The two opposing P*s for each Bi-PAP are anchored in a microarray spot. Each pair of arrows represents four Bi-PAPs for one nucleotide position. A mutation is indicated on the template, and it spans six overlapped P*s. On the microarray, many Bi-PAPs can be processed in a parallel way.
Figure 23B:
Figure 24A:
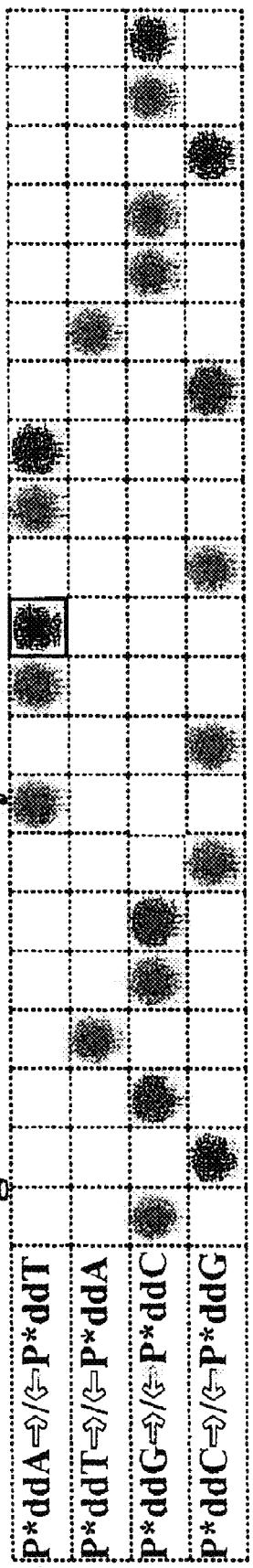

The sensitivity and selectivity of Bi-PAP were examined using three mutation-specific Bi-PAP assays with their corresponding mutated λ DNA (see Table 7 footnotes for definitions). Four titration experiments were performed for each mutation-specific Bi-PAP assay (FIGS. 21A-21C). Experiment I tested how much the mutated P* can "tolerate" the wild-type DNA template (i.e., the maximum copies of the wild-type template without a detectable mutated product). The wild-type λ DNA was titrated from $2 \times 10^{10}$ copies to $2 \times 10^6$ copies. The maximum tolerances were $2 \times 10^9$ to $2 \times 10^{10}$, $2 \times 10^7$ to $2 \times 10^8$, and $2 \times 10^7$ to $2 \times 10^8$, respectively, for the three mutation specific Bi-PAP assays, respectively (FIGS. 21A-21C). Experiment II tested the sensitivity of Bi-PAP. The mutated λ DNA was titrated from $2 \times 10^3$ to 0 copies. The ratio of the maximum tolerance (Experiment I) to the sensitivity is the selectivity. Experiment II was repeated in the presence of large amount of wild-type template (Experiment III) or large amounts of human genomic DNA (Experiment IV) without effects (FIG. 21A; data not shown for T369G and T369C). A dose response with template copy number was observed.

TABLE 7

Summary of the three mutation-specific Bi-PAP assays[a]

| Assay | Position[b] | Type[b] | Sensitivity[c] | Selectivitity[d] |
|-------|-------------|---------|----------------|------------------|
| A | 190 | A:T→T:A | 2 | $10^9:1$ to $10^{10}:1$ |
| B | 369 | T:A→G:C | 2 | $10^7:1$ to $10^8:1$ |
| C | 369 | T:A→C:G | 2 | $10^7:1$ to $10^8:1$ |

[a]In each of the three mutation-specific Bi-PAP assays, two opposite P*s with one nucleotide overlap at their 3' termini were used. The P*s are 40-42 nucleotides long. They are 5' GATGGCGGAGCTGAATTACATTCCCAACCGCGTGGCACAT* (SEQ ID NO: 61) and 5' GGCAACGCCAATCAGCAACGACTGTTTGCCCGCCAGTTGA* (SEQ ID NO: 62) in Assay A; 5' GAAGCGGCGTCGAAGCCTGTAAAGCGGCGGTGCACAATCG* (SEQ ID NO: 63) and 5' GCGGATAGTTAATGATCAGCCCAC TGACGCGTTGCGCGAGAC* (SEQ ID NO: 64) in Assay B; 5' GAAGCGGCGTCGAAGCCTGTAAAGCG-GCGGTGCACAATCC* (SEQ ID NO: 65) and 5' GCGGATAGTTAATGATCAGC-CCACTGACGCGTTGCGCGAG AG* (SEQ ID NO:66) in Assay C.
[b]The position of the first nucleotide of transcript in the lacI gene is assigned the nucleotide position 1 (Farabaugh, 1978). The 3' nucleotide of the P* is located at the indicated position and is complementary to the corresponding mutation.
[c]The sensitivity is defined as the minimum copies of the mutated template from which a detectable mutated product is generated when a mutation-specific Bi-PAP assay is used. It was determined by Experiment II (FIGS. 21A-21C).
[d]The selectivity is the ratio of the maximum copies of the wild-type template with undetectable product the minimum copies of the mutated template with detectable product to, when a mutation-specific Bi-PAP assay is used.

The approximately 100-fold difference in selectivity between the nucleotide positions 190 and 369 may derive from: i) the presence of spontaneous mutations at the position 360 at a frequency of $10^{-7}$ to $10^{-8}$ in the wild-type λ DNA, ii) impurity of P* oligonucleotides, iii) specificity of pyrophosphorolysis for a perfect match at the 3' terminus and fidelity of DNA polymerase to incorporate a correct nucleotide may be associated with sequence context such that the Type II non-specific amplification occurs at a frequency of $10^{-7}$ to $10^{-8}$. In the latter case, a 100-fold difference in selectivity could arise from a 10-fold difference in pyrophosphorolysis specificity and a 10-fold difference in DNA polymerase fidelity with sequence context.

The rate of a spontaneous mutation of λ phage in E. coli varies from locus to locus, on the average from $10^{-9}$ to $10^{-11}$ per incorporated nucleotide. The amplified signal seen in Experiment I might be caused by rare spontaneous mutations.

There is a possible side reaction due to the impurity of P* contamination of unblocked oligonucleotide where the dideoxy terminus has not been added, although no unblocked oligonucleotide was detected in the P*. However, this selectivity may not be limited severely by small amounts of unblocked oligonucleotide because the product generated would be much more likely to be the wild-type rather than the specific mutation ($3.3 \times 10^5:1$).

In summary, Bi-PAP has extremely high sensitivity and selectivity. Bi-PAP can selectively detect two copies of rare mutated allele with a single base substitution from up to $2 \times 10^9$ copies of the wild-type allele. Bi-PAP is a simple, rapid, automatable method for detecting any rare allele of interest.

Example 13

Measurement of Mutation Load in Mouse Tissues by Bi-PAP

Materials and Methods

Liver, heart, adipose tissue, cerebrum and cerebellum from 10-day to 25-month old mice were snap frozen and stored under liquid nitrogen until used. DNA was extracted according to the Big Blue protocol (Stratagene instruction manual). In brief, tissues were homogenized and digested with proteinase K. The genomic DNA was extracted with phenol/chloroform and precipitated with ethanol. The DNA was dissolved in TE buffer (10 mM Tris/HCl, 1 mM EDTA, pH 8.0) and stored at 4° C. The amount of the mouse genomic DNA was determined by UV absorbance at 260 nm.

The mutation-specific Bi-PAP assay for T369G (Assay B: the two opposite P*s are dideoxynucleotide blocked with one nucleotide overlap at their 3' termini are:

```
                                           (SEQ ID NO: 63)
5' GAAGCGGCGTCGAAGCCTGTAAAGCGGCGGTGCACAATCG*3'
and
                                           (SEQ ID NO: 64)
5' GCGGATAGTTAATGATCAGCCCACTGACGCGTTGCGCGAGAC*3'
``` of the lacI gene was performed as above except that i) the reaction contained 2 µg of the mouse genomic DNA (~20 kb in size), unless otherwise stated; ii) mouse DNA in 20 µl (1.25×HEPES buffer, 5% DMSO without $MgCl_2$) was heated at 100° C. for 2 min and quickly cooled on ice, before the other components added; iii) a denaturing step at 95° C. for 1 min was added before the first cycle; iv) the denaturing step was 95° C. for 10 sec.

10 µl of the 25 µl reaction was mixed with 10 µl of the denaturing loading buffer, boiled and rapidly cooled on ice. The product was electrophoresed through a 8% 7M urea/PAGE gel with 90 mM TBE buffer at room temperature. The gel was dried and exposed to Kodak X-OMAT™ AR film for autoradiography.

Results and Discussion

Transgenic mouse mutation detection systems permit determination of the frequency and pattern of spontaneous or induced mutations in vivo. The Big Blue® system uses transgenic mice harboring chromosomally-integrated λ phage DNA containing the E. coli lacI gene as the mutational target (Grossen and Vijg, 1993; Gossen et al., 1989; Kohler et al., 1990. The lacI gene is integrated within each mouse diploid genome in 40 tandemly repeated λ DNAs.

The Big Blue® mutation detection system assay is performed by isolating genomic DNA from transgenic mouse tissues and mixing it with λ packaging extracts. The packaged λ phage can infect E. coli. In the presence of X-gal substrate, lacI mutants give rise to blue plaques on a background of colorless wild-type plaques. Observed mutants derive overwhelmingly from the mouse (Hill et al., 1999). The mutant frequency is determined by dividing the number of circular blue plaques by the total number of plaques. Of 5000 sequenced mutant plaques, 31 T369G mutants have been found in a total of $149 \times 10^6$ plaques screened from various ages, genders and treatments in this laboratory (frequency=$2.1 \times 10^{-7}$).

Figure 26A:
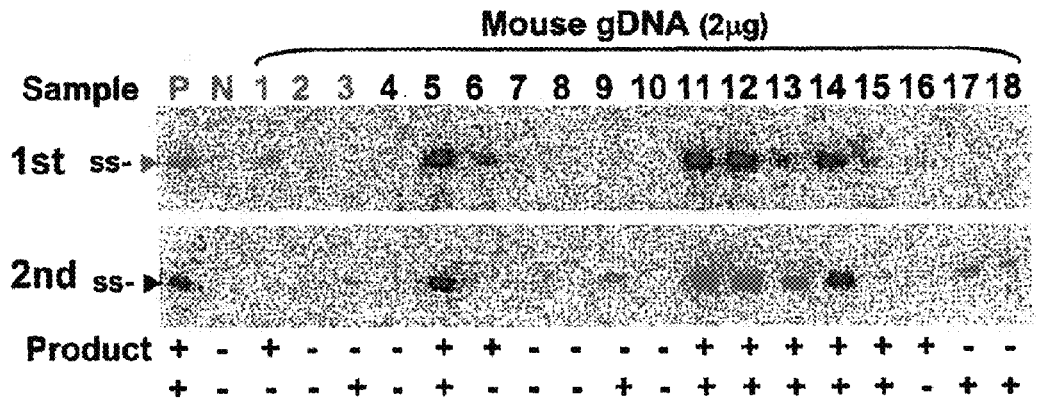
FIGS. 26A-26C show the detection of somatic mutations.

To assess the utility of Bi-PAP for measuring ultra-rare mutations in mammalian cells, the T369G mutation was analyzed in genomic DNA from the Big Blue mice. Two µg of mouse genomic DNA was amplified in 25 µl reaction containing a total of $1.2 \times 10^7$ copies of the lacI gene. The mutation-specific Bi-PAP assay for T369G (Assay B) was performed for 18 samples in duplicate (FIG. 26A). Three categories of results were defined, each with similar number of samples: 1) six samples were positive two times (5, 11-15), 2) seven samples were positive one time (1, 3, 6, 9, 16-18), and 3) five samples were negative two times (2, 4, 7, 8, 10).

Figure 26B:
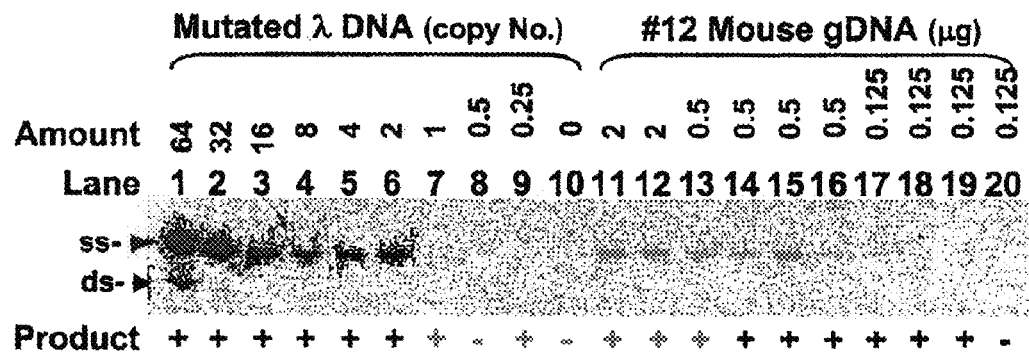
Figure 26C:
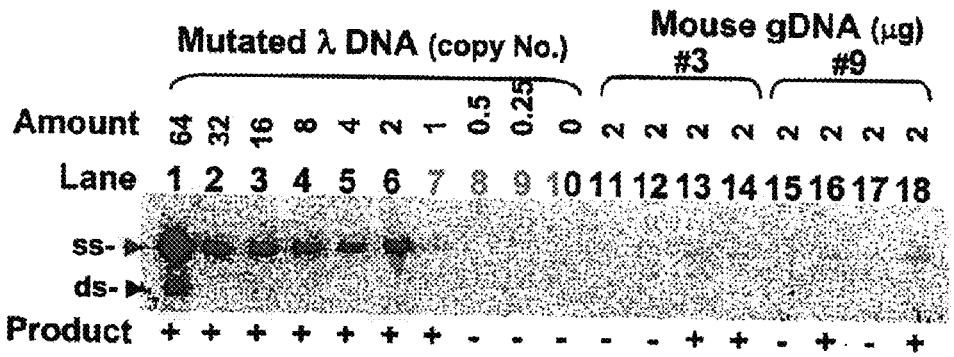

Two samples in each category were studied further (FIGS. 26B-26C, Table 8). In category 1, for the two samples 5 and 12 with the strongest amplified signals (FIG. 26A), a four-fold dilution to 0.5 µg and 16-fold dilution to 0.125 µg of mouse genomic DNA were performed for further quantitation (FIG. 26B). The T369G mutant frequency for each sample was estimated and varies 370-fold among the six samples (Table 8). The average T369G mutant frequency of $2.9 \times 10^{-7}$ was within 50% of the average T369G mutant frequency of $2.1 \times 10^{-7}$ measured from $4 \times 10^7$ plaques using the Big Blue® mutation detection system and confirmed by direct sequencing.

TABLE 8

Somatic mutant frequency measured by Bi-PAP

| | | | Frequency of positive amplification[b] | | | Estimated |
|---|---|---|---|---|---|---|
| | | Mouse genomic DNA | 2 µg of | 0.5 µg of | 0.125 µg of | mutant |
| Sample[a] | Tissue | Age | DNA | DNA | DNA | frequency[d] |
| 1 | 12 | Adipose | 6 months | 8/8 | 8/8 | 4/8 (0.69)[c] | $9.25 \times 10^{-7}$ |
| 2 | 5 | Liver | 25 months | 8/8 | 7/8 | 5/8 (0.98) | $1.31 \times 10^{-6}$ |
| 3 | 3 | Liver | 25 months | 8/24 (0.41) | | | $3.38 \times 10^{-8}$ |
| 4 | 9 | Liver | 25 months | 13/24 (0.78) | | | $6.50 \times 10^{-8}$ |
| 5 | 7 | Liver | 25 months | 2/24 (0.09) | | | $7.25 \times 10^{-9}$ |
| 6 | 10 | Liver | 25 months | 1/24 (0.04) | | | $3.52 \times 10^{-9}$ |
| Average | | | | | | | $2.91 \times 10^{-7}$ |

[a]see FIG. 26A.
[b]the ratio of the number of positive signals for the T369G mutation relative to the total number of reactions.
[c]the average number of T369G mutants per reaction is estimated using a formula (the frequency of zero mutants per reaction = $e^{-x}$, x is the average number of mutants per reaction) suppose that the mutant distributes in the reaction according to a Poisson distribution and that if one or more mutants are in the reaction, the amplification is positive, and if zero mutant is in the reaction, it is negative.
[d]the frequency of the T369G mutant of the lacI gene in mouse genome per reaction is estimated assuming that the mutant distributes in mouse genomic DNA according to a Poisson distribution and that one or more mutants are positive in the detection. For each of samples 12 and 5, a total of $\sim 6.0 \times 10^6$, copies of the lacI gene are used for the estimate, and for each of samples 3, 9, 7 and 10, $\sim 2.9 \times 10^6$ copies are used assuming that 2 µg of the lacI[+] mouse genomic DNA contains $\sim 1.2 \times 10^7$ copies of the lacI gene.

The 370-fold variation in mutant frequency was observed in livers of five mice at 25 months of age. This large variation could be due to difficulties in amplifying one copy of the template. To address this issue, each of the analyses was repeated at least two times with similar results. For example, in sample 9, seven of 14 reactions with 2 µg of DNA were positive in one experiment, three of four such reactions were positive in another experiment, and two of four such reactions were positive in a third experiment. For sample 7, there was one positive in eight and one positive in 14 reactions. The product was sequenced to confirm the T369G mutation after re-amplification from the positive reaction. In addition, positive controls (2 μg of the lacI$^+$ mouse DNA with ~10 copies of T369G) and negative controls (mouse genomic DNA without the lacI target, i.e., the lacI$^-$ mouse DNA) were performed. As additional positive controls, reconstruction experiments were performed in that the copy number of the mutated λ DNA per reaction was serially diluted by two-fold in the presence of the lacI$^-$ genomic DNA carrier. Reproducible amplifications from as low as one copy of template were demonstrated (FIGS. 26B, 26C).

In retrospect, the 370-fold variation in the frequency of T369G mutant observed among the six mice may not be surprising because the T369G mutant frequency among mice is over dispersed, implying a hyper-Poisson distribution (Nishino et al., 1996; Piegorsch et al., 1994). Among six mice the inter-animal variation in the overall mutant frequency assayed by the Big Blue® mutation detection system might be 3 to 4 fold, with significant founder effects in one or a few of the mice. The variation might be in the range of $2 \times 10^{-5}$ to $8 \times 10^{-5}$ which is the sum of more than 1,000 different mutations. Here, only the T369G mutation is assayed. It is anticipated that the great majority of the signal derives from duplex mutated templates (Hill et al., 1999), but it should be noted that unresolved mismatch intermediates derived primarily from DNA replication or DNA repair would also generate a signal. Thus, the physical limit of sensitivity is actually one half of a duplex DNA molecule per reaction.

In conclusion, we demonstrate that Bi-PAP can analyze ultra-rare mutations at frequencies as low as $10^{-7}$ to $10^{-9}$, depending on the assay. It is shown that Bi-PAP can detect single copies of the somatic mutation directly from mammalian genomic DNA. The inter-assay variation may reflect locus-specific variability in the assay sensitivity or in the frequency of the assayed mutants among the samples. More work is necessary to distinguish between these possibilities. In mammalian DNA, the number of copies of template is limited by the enormous genome size. Two μg of genomic DNA contains only 600,000 mouse haploid genomes, yet the reaction is viscous. Our analysis of the Big Blue mouse genomic DNA was facilitated by the 20 copies of the lacI gene per haploid genome. To measure mutation load in humans, genomic DNA in one reaction could be increased at least three fold by reducing the viscosity (e.g., shearing the DNA into small segments by ultrasonic treatment) and another four fold by expanding the reaction volume to 100 μl. Mutation load in human genomic DNA might be facilitated by analyzing segments of virtually identical sequence, e.g., there are three 9.6 kb segments with 99$^+$% sequence identity on human X chromosome involved in a common inversion mutation in hemophilia A (Lakich et al., 1993). Less complex genomes including C-elegans, Drosophila, and human mitochondria genome or chronic viral infections (e.g., hepatitis B) also should be analyzable with this protocol.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

BIBLIOGRAPHY

Anion, D. et al., *Biochemistry* 37, 15908-15917 (1998).
Bains W. and Smith G. C., *J Theor Biol* 135, 303-307 (1988).
Banér, J. et al., *Nucleic Acids Res* 26, 5073-5078 (1998).
Barany, F., *Proc Natl Acad Sci USA* 88, 189-193 (1991).
Bebenek, K. et al., *J Biol Chem* 265, 13878-13887 (1990).
Becker, M. M. and Grossmann, G., in *Footprinting of nucleic acid-protein complexes* (ed. Revzin, A.), pp. 129-159 (Academic Press, New York, 1993).
Boer, P. H. et al., *Biochem Genet* 28, 299-308 (1990).
Buzin, C. H. et al., *Bio Techniques* 28, 746-753 (2000).
Cheng, Y. C. et al., *J Biol Chem* 262, 2187-2189 (1987).
Chien, A. et al., *Bacteriol* 127, 1550-1557 (1976).
Chou, Q. et al., *Nucl Acids Res.* 20, 1717-1723 (1992).
Cotton, R. G. et al., *Proc Natl Acad Sci USA* 85, 4397-4401 (1988).
Dai, S.-M. et al., *Nature Biotechnology* 18:1108-1111 (2000).
D'Aquila, R. J. et al., *Nucl Acids Res* 19, 3749 (1991).
Drmanac, R. et al., *Genomics* 4, 114-128 (1989).
Duetcher, M. P. and Kornberg, A., *J Biol Chem* 244, 3019-3028 (1969).
Eckert, K. A. and Kunkel, T. A., *Nucleic Acids Res.* 18, 3739-3744 (1990).
Gardner, A. F. and Jack, W. E., *Nucleic Acids Res* 30:605-613 (2002).
Gardner, A. F. and Jack, W. E., *Nucleic Acids Res* 27:2545-2553 (1999).
Ginot, F., *Hum Mutat* 10, 1-10 (1997).
Gossen, J. and Vijg, J., *Trends Genet* 9, 27-31 (1993).
Gossen, J. A. et al., *Proc Natl Acad Sci USA* 86, 7971-7975 (1989).
Gotte, M. et al., *J Virol* 74, 3579-3585 (2000).
Hacia, J. et al., *Nat Genet* 21, 42-47 (1999).
Hill, K. A. et al., *Mutat Res Mini Reviews* 436, 11-19 (1999).
Innis, M. A. and Gelfand, D. H., in *PCR APPLICATIONS Protocols for Functional Genomics* (eds. Innis, M. A., Gelfand, D. H. & Sninsky, J. J.), pp. 3-22 (Academic Press, 1999).
Jones, P. A. and Laird, P. W., *Nat Genet* 21, 163-167 (1999).
Kaledin, A. S. et al., *Biokhimiia* 46, 1576-1584 (1981).
Kellogg, D. E. et al., *Biotechniques* 16, 1134-1137 (1994).
Ketterling, R. P. et al., *Hum Genet* 105, 629-640 (1999).
Khrapko, K. R. et al., *FEBS Letts* 256. 118-122 (1989).
Knoll, A. et al., *Hum Genet* 98, 539-545 (1996).
Kohler, S. W. et al., *Strategies in Mol Biol* 3, 19-21 (1990).
Kohler, S. W. et al., *Proc Natl Acad Sci USA* 88, 7958-7962 (1991).
Komura, J. and Riggs, A. D., *Nucleic Acids Res* 26, 1807-1811 (1998).
Kornberg, A. and Baker, T. A., *DNA Replication*, (eds., Second Edition), pp. 113-226 (W.H. Freeman and Co., New York 1992).
Lakich, D. et al., *Nature Genet* 5, 236-241 (1993).
Landegren, U. et al., *Science* 241, 1077-1080 (1988).
LeProust, E. et al., *J Comb Chem* 2, 349-354 (2000).
Liu, Q. and Sommer, S., *BioTechniques* 29, 1072-1083 (2000).
Liu, Q. and Sommer, S., *BioTechniques* 18, 470-477 (1995).
Liu, Q. et al., *Am J Med Genet (Neuropsych Genet)* 60, 165-171 (1995).
Liu, Q. et al., *BioTechniques* 26, 932-942 (1999).
Liu, Q. et al., *BioTechniques* 33, 129-138 (2002).
Liu, Q. et al., *Anal Biochem* 270, 112-122 (1999b).
Lizardi, P. M. et al., *Nature Genetics* 19, 225-232 (1998).
Longley, M. J. et al., *Nucleic Acids Res* 18, 7317-7322 (1990).
Lysov, I. et al., *Dokl Akad Nauk SSSR* 303, 1508-1511 (1988).
Maniatis, T. et al., *Molecular Cloning: a Laboratory Manual*, Cold Spring Harbor, N.Y.: Cold Spring Harbor Laboratory, 1982.

Marshall, A. and Hodgson, I., *Nat Biotechnol* 16, 27-31 (1998)
Maxam, A. M. and Gilbert, W., *Proc Natl Acad Sci USA* 74, 560-564 (1977).
Meyer, P et al., *EMBO J* 19, 3520-3529 (2000).
Miyada, C. G. and Wallace, R. B., *Methods in Enzymology* 154, 94-107 (1987).
Mueller, P. R. and Wold, B., *Science* 246, 780-786 (1989). [published erratum, appears in *Science* 248, 802 (1990).]
Mullis, K. B., *PCR Methods Appl* 1, 11-4 (1991).
Myers, R. M. et al., *Science* 230, 1242-1246 1985).
Nishino, H. et al., *Environ Mol Mutagen* 28, 299-312 (1996).
Nishino, H. et al., *Environ Mol Mutagen* 28, 414-417 (1996).
O'Donovan, M. C. et al., *Genomics* 52, 44-49 (1998).
Oefner, P. and Underhill, P., *Current Protocols in Human Genetics* Supplement 19:7.10.1-7.10.12 (1998).
Orita, M. et al., *Proc Natl Acad Sci USA* 86:2766-2770 (1989).
Parsons, B. L. and Heflich, R. H., *Mutat Res* 387, 97-121 (1997).
Pevzner P. A., *J Biomol Struct Dyn* 7, 63-73 (1989).
Pfeifer, G. F. et al., *Science* 246, 810-813 (1989).
Pfeifer, G. P. et al., *Methods Enzymol* 304, 548-571 (1999).
Piegorsch, W. W. et al., *Environ Mol Mutagen* 23, 17-31 (1994).
Pourzand, C. and Cerutti, P., *Mutat Res* 288, 113-121 (1993).
Ramsay, G., *Nat Biotechnol* 16, 40-44 (1998).
Ronaghi, M. et al., *Science* 281, 363, 365 (1998).
Ronai, Z. and Minamoto, T., *Hum Mutat* 10, 322-325 (1997).
Russo, E. and Riggs, A. D., Epigenetics mechanics of gene regulation. In: Anonymous 1996
Saiki, R. K. et al., *Science* 230, 1350-1354 (1985).
Saiki, R. K. et al., *Science* 239, 487-491 (1988).
Sanger, F. et al., *Proc Natl Acad Sci USA* 74, 5463-5467 (1977).
Sarkar, G. et al., *Anal Biochem* 186, 64-68 (1990).
Sarkar, G. et al., *Nucleic Acids Res* 20, 871-878 (1992).
Singh-Gasson, S. et al., *Nat Biotechnol* 17, 974-978 (1999).
Sommer, S. S., *Trends Genet* 11, 141-147 (1995).
Sommer, S. S. et al., *Mayo Clinic Prac.* 64, 1361-1372 (1989).
Southern, E. M. et al., *Genomics* 13, 1008-1017 (1992).
Southern, E. M., *Trends Genet* 12, 110-115 (1996).
Spiegelman, J. I. et al., *BioTechniques* 29, 1084-1092 (2000).
St. Clair, M. H., *Antimicrob Agents Chemother* 31, 1972-1977 (1987).
Syvanen, A. C., *Hum Mutat* 13, 1-10 (1999).
Tabor, S. and Richardson, C. C., *J Biol Chem* 265, 8322-8328 (1990).
Tabor, S. and Richardson, C. C., *Proc Natl Acad Sci USA* 92, 6339-6343 (1995).
Trainor, G. L., U.S. Pat. No. 5,558,991 (1996).
Ueno, T. and Mitsuya, H., *Biochemistry* 36, 1092-1099 (1997).
Urban, S. et al., *Proc Natl Acad Scie USA* 98, 4984-4989 (2001).
Vander Horn, P. B. et al., *BioTechniques* 22, 758-762 (1997).
Wallace, R. B. et al., *Nucleic Acids Res* 6, 3543-3557 (1979).
Wong, I. et al., *Biochemistry* 30, 526-537 (1991).
Yoshitake, S. et al., *Biochemistry* 24, 3736-3750 (1985).

What is claimed is:

1. A process which comprises serial coupling of two reactions, the first reaction being activation of an inactive oligonucleotide which, if not activated, would prevent the oligonucleotide from being extended on a nucleic acid template and the second reaction being an extension of the activated oligonucleotide on the nucleic acid template, wherein the inactive oligonucleotide has a match at the 3' end nucleotide with the nucleic acid template and wherein the inactive oligonucleotide is activated by a nucleic acid metabolizing enzyme, wherein the nucleic acid metabolizing enzyme is RNase H.

2. The process of claim 1, wherein the inactive oligonucleotide has a 3' end block.

3. The process of claim 1, wherein the extension is performed in the presence of four nucleoside triphosphates and a nucleic acid polymerase.

4. The process of claim 1, wherein the oligonucleotide is at least partially hybridized to the template before and during the first reaction.

5. The process of claim 1, wherein the extension is part of an amplification of the nucleic acid template.

* * * * *

UNITED STATES PATENT AND TRADEMARK OFFICE
CERTIFICATE OF CORRECTION

PATENT NO. : 8,173,371 B2  
APPLICATION NO. : 12/956656  
DATED : May 8, 2012  
INVENTOR(S) : Qiang Liu et al.

Page 1 of 1

It is certified that error appears in the above-identified patent and that said Letters Patent is hereby corrected as shown below:

*In the Specification*

Col. 1, line 23: "application" should be -- Application --

Col. 49, line 66: "volume of" should be -- volume of 25 µl: --

Col. 57, line 66: "Anion" should be -- Arion --

Signed and Sealed this  
Twenty-ninth Day of January, 2013

David J. Kappos  
*Director of the United States Patent and Trademark Office*